US008076326B2

United States Patent
Haupt et al.

(10) Patent No.: US 8,076,326 B2
(45) Date of Patent: Dec. 13, 2011

(54) N-PHENYL- (PIPERAZINYL OR HOMOPIPERAZINYL)-BENZENESULFONAMIDE OR BENZENESULFONYL-PHENL-(PIPERAZINE OR HOMOPIPERAZINE) COMPOUNDS SUITABLE FOR TREATING DISORDERS THAT RESPOND TO MODULATION OF THE SEROTONIN 5-HT$_6$ RECEPTOR

(75) Inventors: Andreas Haupt, Ludwigshafen (DE);
Frauke Pohlki, Ludwigshafen (DE);
Karla Drescher, Ludwigshafen (DE);
Karsten Wicke, Ludwigshafen (DE);
Liliane Unger, Ludwigshafen (DE);
Ana-Lucia Relo, Ludwigshafen (DE);
Anton Bespalov, Ludwigshafen (DE);
Barbara Vogg, Ludwigshafen (DE);
Gisela Backfisch, Ludwigshafen (DE);
Juergen Delzer, Ludwigshafen (DE);
Min Zhang, Abbott Park, IL (US);
Yanbin Lao, Abbott Park, IL (US)

(73) Assignees: Abbott GmbH & Co. KG, Wiesbaden (DE); Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/770,837

(22) Filed: Apr. 30, 2010

(65) Prior Publication Data
US 2010/0280014 A1 Nov. 4, 2010

Related U.S. Application Data

(60) Provisional application No. 61/174,054, filed on Apr. 30, 2009.

(51) Int. Cl.
A61K 31/495 (2006.01)
A61K 31/496 (2006.01)
A61K 31/551 (2006.01)
C07D 295/112 (2006.01)
C07D 317/64 (2006.01)
C07D 317/66 (2006.01)

(52) U.S. Cl. ............. 514/218; 514/254.11; 514/255.03; 540/575; 544/377; 544/395

(58) Field of Classification Search .................. None
See application file for complete search history.

(56) References Cited

U.S. PATENT DOCUMENTS
6,316,450 B1 * 11/2001 Bromidge et al. ...... 514/253.05
2003/0069233 A1     4/2003 Bromidge et al.

FOREIGN PATENT DOCUMENTS
| WO | 98/27081 | 6/1998 |
| WO | 99/02502 | 1/1999 |
| WO | 00/12073 | 3/2000 |
| WO | 00/12623 | 3/2000 |
| WO | 02/08179 | 1/2002 |
| WO | 02/92585 | 11/2002 |
| WO | 03/014097 | 2/2003 |
| WO | 2004/080986 | 9/2004 |
| WO | 2006/010629 | 2/2006 |
| WO | 2008/087123 | 7/2008 |

OTHER PUBLICATIONS

Robichaud et al. in Annual Reports in Medicinal Chemistry, vol. 36, p. 11-20 (2000).*
Rogers et al. Psychopharmacology, vol. 158, p. 114-119 (2001).*
Holenz et al. Drug Discovery Today, vol. 11,p. 494 (2006) (Abstract provided).*
A. Meneses, Drug News Perspect 14(7) (2001) pp. 396-400.
J. Pharmacol. Sci. vol. 101, (Suppl. 1), 2006, p. 124. Gannon et al.

* cited by examiner

Primary Examiner — Emily Bernhardt
(74) Attorney, Agent, or Firm — Lisa V. Mueller; Michael Best & Friedrich LLP

(57) ABSTRACT

The present invention relates to N-phenyl-(piperazinyl or homopiperazinyl)-benzenesulfonamide or benzenesulfonyl-phenyl-(piperazine or homopiperazine) compounds, pharmaceutical compositions containing them, and their use in therapy. The compounds possess valuable therapeutic properties and are particularly suitable for treating diseases that respond to modulation of the serotonin 5-HT$_6$ receptor.

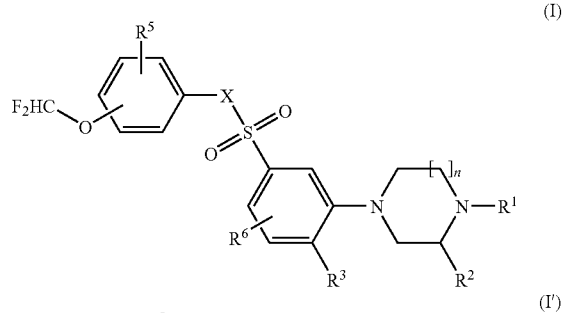

(I)

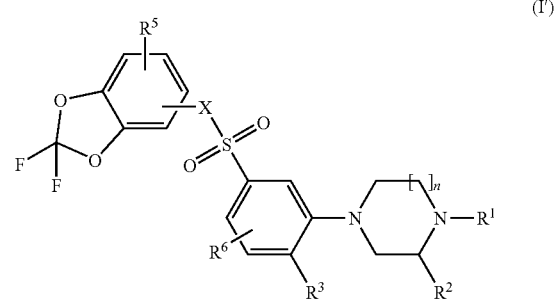

(I')

wherein
X is a bond or a group N—R$^4$;
R$^1$ is hydrogen or methyl;
R$^2$ is hydrogen or methyl;
R$^3$ is hydrogen, C$_1$-C$_3$ alkyl, fluorine, C$_1$-C$_2$ alkoxy or fluorinated C$_1$-C$_2$ alkoxy;
R$^4$ is hydrogen, C$_1$-C$_4$ alkyl, C$_3$-C$_4$ cycloalkyl, or C$_3$-C$_4$ cycloalkyl-CH$_2$—; R$^5$ is hydrogen, fluorine, chlorine, C$_1$-C$_2$ alkyl, fluorinated C$_1$-C$_2$ alkyl, C$_1$-C$_2$ alkoxy or fluorinated C$_1$-C$_2$ alkoxy;
R$^6$ is hydrogen, fluorine or chlorine; and
n is 1 or 2.

28 Claims, No Drawings

N-PHENYL- (PIPERAZINYL OR HOMOPIPERAZINYL)-BENZENESULFONAMIDE OR BENZENESULFONYL-PHENL-(PIPERAZINE OR HOMOPIPERAZINE) COMPOUNDS SUITABLE FOR TREATING DISORDERS THAT RESPOND TO MODULATION OF THE SEROTONIN 5-HT$_6$ RECEPTOR

CROSS-REFERENCE TO RELATED APPLICATIONS

This claims priority to U.S. Provisional Patent Application Ser. No. 61/174,054, filed Apr. 30, 2009, the contents of which are hereby incorporated by reference.

BACKGROUND OF THE INVENTION

The present invention relates to N-phenyl-(piperazinyl or homopiperazinyl)-benzenesulfonamide or benzenesulfonyl-phenyl-(piperazine or homopiperazine) compounds, pharmaceutical compositions containing them, and their use in therapy. The compounds possess valuable therapeutic properties and are particularly suitable for treating diseases that respond to modulation of the serotonin 5-HT$_6$ receptor.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Until now, seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of either adenylate cyclase or phospholipase Cγ.

The human 5-HT$_6$ receptors are positively coupled to adenylyl cyclase. They are distributed throughout the limbic, striatal and cortical regions of the brain and show a high affinity to antipsychotics.

The modulation of the 5-HT$_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases and obesity (see e.g. A. Meneses, Drug News Perspect 14(7) (2001) pp. 396-400 and literature cited therein; J. Pharmacol. Sci. Vol. 101 (Suppl. 1), 2006, p. 124. Modulators of the 5HT$_6$-receptor such as PRX-07034 (Epix Pharmaceuticals) have been found in preclinical and clinical studies to be particular useful in the treatment of cognitive dysfunctions, in particular associated with Alzheimer's disease or schizophrenia or in the treatment of obesity (see e.g. http://www.epixpharma.com/products/prx-07034.asp).

WO 98/027081, WO 99/02502, WO 00/12623, WO 00/12073, US 2003/0069233, WO 02/08179, WO 02/92585, WO 2006/010629 describe certain benzenesulfonanilide compounds having 5HT$_6$ receptor antagonist activity and suggest the use of these compounds for the treatment of medical disorders which are susceptible to the treatment with 5HT$_6$ receptor antagonists such as certain CNS disorders, drug abuse, ADHD, obesity and type II diabetes. WO 2004/080986 and WO 03/014097 describe certain diarylsulfone compounds, suggesting the use of these compounds for the treatment of medical disorders which are susceptible to the treatment with 5HT$_6$ receptor antagonists such as certain CNS disorders, drug abuse, ADHD, obesity and type II diabetes. WO 2008087123 suggests compounds having 5HT$_6$ receptor antagonist activity for preventing relapse into addiction.

However, there is still an ongoing need for providing compounds having high affinity for the 5-HT$_6$ receptor and which show high selectivity to this receptor. In particular the compounds should have low affinity to adrenergic receptors, such as α$_1$-adrenergic receptor, histamine receptors, such as H$_1$-receptor, and dopaminergic receptors, such as D$_2$-receptor, in order to avoid or reduce considerable side effects associated with modulation of these receptors, such as postural hypotension, reflex tachycardia, potentiation of the antihypertensive effect of prazosin, terazosin, doxazosin and labetalol or dizziness associated to the blockade of the α$_1$-adrenergic receptor, weight gain, sedation, drowsiness or potentiation of central depressant drugs associated to the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the D$_2$-receptor.

It is one object of the present invention to provide compounds which have a high affinity for the 5-HT$_6$ receptor. It is a further object of the present invention to provide compounds which selectively bind to the 5-HT$_6$ receptor.

The compounds should also have good pharmacological profile, e.g. a good bioavailability and/or a good metabolic stability.

SUMMARY OF THE INVENTION

The present invention relates to N-phenyl-(piperazinyl or homopiperazinyl)-benzenesulfonamides or benzenesulfonyl-phenyl-(piperazines or homopiperazines) of formula (I) or (I')

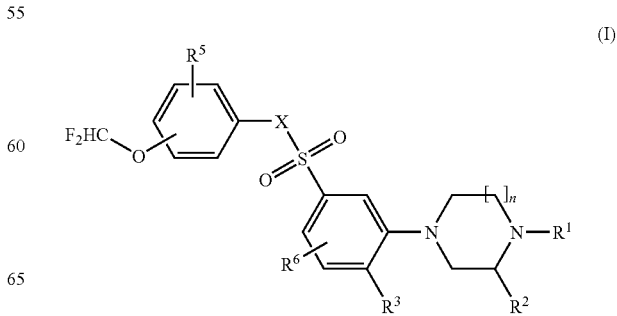

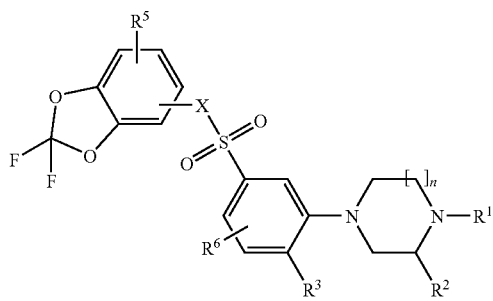

(I')

wherein
X is a bond or a group N—R⁴;
R¹ is hydrogen or methyl;
R² is hydrogen or methyl;
R³ is hydrogen, $C_1$-$C_3$ alkyl (e.g. methyl), fluorine, $C_1$-$C_2$ alkoxy (e.g. methoxy) or fluorinated $C_1$-$C_2$ alkoxy;
R⁴ is hydrogen $C_1$-$C_4$ alkyl (e.g. methyl, ethyl, n-propyl, isopropyl), $C_3$-$C_4$ cycloalkyl, or —$CH_2$—$C_3$—$C_4$ cycloalkyl (e.g. cyclopropylmethyl);
R⁵ is hydrogen, fluorine, chlorine, $C_1$-$C_2$ alkyl (e.g. methyl), fluorinated $C_1$-$C_2$ alkyl, $C_1$-$C_2$ alkoxy (e.g. methoxy) or fluorinated $C_1$-$C_2$ alkoxy;
R⁶ is hydrogen, fluorine or chlorine; and
n is 1 or 2,
and physiologically tolerated acid addition salts and the N-oxides thereof.

Said compounds, i.e., the N-phenyl-(piperazinyl or homopiperazinyl)-benzenesulfonamides or benzenesulfonyl-phenyl-piperazines or -homopiperazines and their physiologically tolerated acid addition salts and the N-oxides thereof, exhibit to a surprising and unexpected degree, a high binding affinity to the 5-$HT_6$ receptor and are thus useful as pharmaceuticals.

The present invention thus further relates to the compounds of formula (I) or (I') for use in therapy.

The present invention also relates to pharmaceutical compositions which comprise a compound of formula (I) or (I') and, optionally, a physiologically acceptable carrier and/or an auxiliary substance.

In particular, said compounds, i.e., the N-phenyl-(piperazinyl or homopiperazinyl)-benzenesulfonamides or benzenesulfonyl-phenyl-(piperazines or homopiperazines) and their physiologically tolerated acid addition salts and the N-oxides thereof, are modulators of the 5-$HT_6$ receptor.

The present invention thus further relates to the compounds of formula (I) or (I') for use in modulating the 5-$HT_6$ receptor.

The present invention also relates to the use of the compounds of formula (I) or (I') in the manufacture of a medicament for modulating the 5-$HT_6$ receptor and corresponding methods of modulating the 5-$HT_6$ receptor.

Modulators of the 5-$HT_6$ receptor and in particular antagonists of the 5-$HT_6$ receptor are known to be useful in treating a variety of disorders.

The present invention thus further relates to the compounds of formula (I) or (I') for use in treating said disorders.

The present invention also relates to the use of the compounds of formula (I) or (I') in the manufacture of a medicament for treating said disorders and corresponding methods of treating said disorders.

DETAILED DESCRIPTION OF THE INVENTION

The disorders diseases which are susceptible to treatment with a compound of the formula (I) or (I') include, e.g., disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, including hydrocephalus, drug addiction and obesity.

Provided the compounds of the formula (I) or (I') of a given constitution may exist in different spatial arrangements, for example if they possess one or more centers of asymmetry, polysubstituted rings or double bonds, or as different tautomers, the invention also relates to enantiomeric mixtures, in particular racemates, diastereomeric mixtures and tautomeric mixtures, preferably, however, the respective essentially pure enantiomers (ennatiomerically pure), diastereomers and tautomers of the compounds of formula (I) or (I') and/or of their salts and/or their N-oxides.

The invention also relates to physiologically tolerated salts of the compounds of the formula (I) or (I'), especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The invention also relates to N-oxides of the compounds of the formula (I) or (I'), provided that those compounds contain a basic nitrogen atom, such as the nitrogen atom of the piperazine moiety.

The organic moieties mentioned in the above definitions of the variables are—like the term halogen—collective terms for individual listings of the individual group members. The prefix $C_n$-$C_m$ indicates in each case the possible number of carbon atoms in the group.

As used herein, $C_1$-$C_4$ alkyl is a straight-chain or branched alkyl group having 1, 2, 3 or 4 carbon atoms. Examples of such a group include methyl, ethyl, n-propyl, 1-methylethyl (isopropyl), n-butyl, 1-methylpropyl (=2-butyl), 2-methylpropyl (=isobutyl) and 1,1-dimethylethyl (=tert.-butyl).

As used herein, fluorinated $C_1$-$C_2$ alkyl is a straight-chain alkyl group having 1 or 2 carbon atoms, wherein at least one hydrogen atom, e.g. 1, 2, 3, 4 or 5 hydrogen atoms, are replaced by fluorine. Examples of such a group include fluoromethyl, difluoromethyl, trifluoromethyl, 2-fluoroethyl, 2,2-difluoroethyl, 2,2,2-trifluoroethyl, 1,1,2,2-tetrafluoroethyl and 1,1,2,2,2-pentafluoroethyl.

As used herein, $C_1$-$C_2$ alkoxy is a straight-chain alkyl group having 1 or 2 carbon atoms which is bound to the remainder of the molecule via an oxygen atom, i.e., methoxy and ethoxy.

As used herein, fluorinated $C_1$-$C_2$ alkoxy is an alkoxy group as defined above, wherein at least one, e.g. 1, 2, 3, 4 or 5 hydrogen atoms are replaced by fluorine atoms. Examples of such a group are fluoromethoxy, difluoromethoxy, trifluoromethoxy, 2-fluoroethoxy, 2,2-difluoroethoxy, 2,2,2-trifluoroethoxy and 1,1,2,2-tetrafluoroethoxy.

As used herein, $C_3$-$C_4$-cycloalkyl is a cycloaliphatic radical having from 3 to 4 carbon atoms, i.e. cyclopropyl and cyclobutyl.

With respect to the compounds' capability of modulating the 5-HT$_6$ receptor, the variables X, $R^1$, $R^2$, $R^3$, $R^4$, $R^5$, $R^6$ and n preferably have the following meanings which, when taken alone or in combination, represent particular embodiments of the compounds of the formula (I) or (I').

X is a bond or a group N—$R^4$. A first preferred embodiment of the invention relates to compounds of the formula I or I', to their pharmacologically tolerated salts and to the N-oxides thereof, wherein X is a group N—$R^4$.

$R^1$ is hydrogen or methyl. A second preferred embodiment of the invention relates to compounds of the formula I or I', to their pharmacologically tolerated salts and to the N-oxides thereof, wherein $R^1$ is hydrogen. Another embodiment of the invention relates to compounds of the formula I or I', to their pharmacologically tolerated salts and to the N-oxides thereof, wherein $R^1$ is methyl.

$R^2$ is hydrogen or methyl. A third preferred embodiment of the invention relates to compounds of the formula I or I', to their pharmacologically tolerated salts and to the N-oxides thereof, wherein $R^2$ is hydrogen.

Another embodiment of the invention relates to compounds of the formula I or I', wherein $R^2$ is methyl. If $R^2$ is methyl, the carbon atom that carries $R^2$ creates a center of chirality. Thus, a specific embodiment of the invention relates to compounds of the formula I or I', to their pharmacologically tolerated salts and to the N-oxides thereof, wherein $R^2$ is methyl and wherein the carbon atom that carries $R^2$ has S-configuration. Another specific embodiment of the invention relates to compounds of the formula I or I', to their pharmacologically tolerated salts and to the N-oxides thereof, wherein $R^2$ is methyl and wherein the carbon atom that carries $R^2$ has R-configuration.

Likewise preferred are mixtures of compounds of the present invention, wherein the carbon atom that carries $R^2$ has S-configuration or R-configuration, respectively. These mixtures may contain equal amounts or non-equal amounts of the compound I, or equal amounts or non-equal amounts of the compound I', respectively, that have R-configuration with regard to the moiety CH—$R^2$ and of the compound I or I' that have S-configuration with regard to CH—$R^2$.

The term "enantiomerically pure" means that the mixture contains the respective compound in an entaniomeric excess of at least 80%, in particular at least 90% (ee).

$R^3$ is hydrogen, $C_1$-$C_3$ alkyl (e.g. methyl), fluorine, $C_1$-$C_2$ alkoxy (e.g. methoxy) or fluorinated $C_1$-$C_2$ alkoxy.

Preference is given to compounds of the formula I or I', to their pharmacologically tolerated salts and to the N-oxides thereof, wherein $R^3$ is methyl or methoxy, difluoromethoxy or trifluoromethoxy, in particular methyl or methoxy, and most preferably methyl. The invention also relates to compounds of the formula I or I', to their pharmacologically tolerated salts and to the N-oxides thereof, wherein $R^3$ is hydrogen or fluorine, in particular hydrogen.

$R^4$ is hydrogen, $C_1$-$C_4$ alkyl (e.g. methyl, ethyl, n-propyl, isopropyl), $C_3$-$C_4$ cycloalkyl, or $C_3$-$C_4$ cycloalkyl-$CH_2$— (e.g. cyclopropylmethyl).

Preference is given to compounds of the formula I or I', to their pharmacologically tolerated salts and to the N-oxides thereof, wherein $R^4$ is hydrogen, methyl, ethyl, n-propyl, isopropyl or cyclopropylmethyl. More preference is given to the compounds of the present invention, wherein $R^4$ is hydrogen.

$R^5$ is hydrogen, fluorine, $C_1$-$C_2$ alkyl (e.g. methyl), fluorinated $C_1$-$C_2$ alkyl, $C_1$-$C_2$ alkoxy (e.g. methoxy) or fluorinated $C_1$-$C_2$ alkoxy.

$R^5$ is preferably selected from the group consisting of hydrogen, fluorine, methyl, trifluoromethyl, methoxy, difluoromethoxy and trifluoromethoxy and more preferably from hydrogen, methoxy and difluoromethoxy. Likewise, preference is given to the compounds of the formula I or I', wherein $R^5$ is chlorine. In a particular preferred embodiment of the invention, $R^5$ is hydrogen. In another particular preferred embodiment of the invention, $R^5$ is selected from fluorine, methyl, trifluoromethyl, methoxy, difluoromethoxy and trifluoromethoxy and more preferably from methyl, methoxy and difluoromethoxy. Likewise, more preference is given to the compounds of the formula I or I', wherein $R^5$ is fluorine. Likewise, more preference is given to the compounds of the formula I or I', wherein $R^5$ is chlorine.

$R^6$ is hydrogen, fluorine or chlorine, preferably hydrogen or fluorine. In a particular preferred embodiment of the invention, $R^6$ is hydrogen. In another particular embodiment of the invention $R^6$ is different from hydrogen, in particular fluorine. If $R^6$ is different from hydrogen it is preferably located in the 5- or 6-postion of the benzene ring.

Preference is given to those compounds of the formula I or I', to their pharmacologically tolerated salts and to the N-oxides thereof, wherein $R^3$ is methyl or methoxy and $R^6$ is hydrogen, or $R^3$ is methyl or methoxy and $R^6$ is fluorine being located in the 5- or 6-position of the benzene ring, or both $R^3$ and $R^6$ are hydrogen or $R^3$ is hydrogen and $R^6$ is fluorine being located in the 5- or 6-position of the benzene ring.

According to a further particular embodiment, $R^5$ and $R^6$ are hydrogen, $R^3$ is selected from the group consisting of $C_1$-$C_2$ alkyl (e.g. methyl) and $C_1$-$C_2$ alkoxy (e.g. methoxy), and $R^4$ is selected from the group consisting of hydrogen, $C_1$-$C_4$ alkyl (e.g. methyl, ethyl, n-propyl, isopropyl), or cyclopropylmethyl.

n is 1 or 2, thus forming a piperazine or a homopiperazine moiety. Preference is give to n being 1, i.e. compounds having a piperazine moiety.

A particular preferred embodiment Ia of the invention relates to compounds of the formula I, to their pharmacologically tolerated salts and to the N-oxides thereof, wherein $R^1$ is hydrogen;
$R^2$ is hydrogen;
$R^3$ is methyl, methoxy, difluoromethoxy or trifluoromethoxy, in particular methyl or methoxy; and
$R^4$ is hydrogen.

A further particular preferred embodiment Ib of the invention relates to compounds of the formula I, to their pharmacologically tolerated salts and to the N-oxides thereof, wherein $R^1$ is hydrogen;
$R^2$ is hydrogen;
$R^3$ is methyl, methoxy, difluoromethoxy or trifluoromethoxy, in particular methyl or methoxy; and
$R^4$ is methyl.

A further particular preferred embodiment Ic of the invention relates to compounds of the formula I, to their pharmacologically tolerated salts and to the N-oxides thereof, wherein $R^1$ is methyl;
$R^2$ is hydrogen;
$R^3$ is methyl, methoxy, difluoromethoxy or trifluoromethoxy, in particular methyl or methoxy; and
$R^4$ is hydrogen.

A further particular preferred embodiment Id of the invention relates to compounds of the formula I, to their pharmacologically tolerated salts and to the N-oxides thereof, wherein
$R^1$ is methyl;
$R^2$ is hydrogen;
$R^3$ is methyl, methoxy, difluoromethoxy or trifluoromethoxy, in particular methyl or methoxy; and
$R^4$ is methyl.

A particular preferred embodiment Ie of the invention relates to compounds of the formula I, to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is hydrogen.

A further particular preferred embodiment If of the invention relates to compounds of the formula I, to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is methyl.

A further particular preferred embodiment Ig of the invention relates to compounds of the formula I, to their pharmacologically tolerated salts and to the N-oxides thereof, wherein
$R^1$ is methyl;
$R^2$ is hydrogen;
$R^3$ is hydrogen or fluorine, in particular hydrogen; and
$R^4$ is hydrogen.

A further particular preferred embodiment Ih of the invention relates to compounds of the formula I, to their pharmacologically tolerated salts and to the N-oxides thereof, wherein
$R^1$ is methyl;
$R^2$ is hydrogen;
$R^3$ is hydrogen or fluorine, in particular hydrogen; and
$R^4$ is methyl.

Amongst the compounds of embodiments Ia, Ib, Ic, Id, Ie, If, Ig and Ih, preference is given to those, where the radicals $R^5$ and $R^6$ in formula I are both hydrogen.

Amongst the compounds of embodiments Ia, Ib, Ic, Id, Ie, If, Ig and Ih, likewise preference is given to those, where the radical $R^5$ in formula I is hydrogen and where the radical $R^6$ in formula I is fluorine, which is located in the 5-position or in the 6-position of the benzene ring.

Amongst the compounds of embodiments Ia, Ib, Ic, Id, Ie, If, Ig and Ih, likewise preference is given to those, where the radical $R^5$ in formula I is methoxy and where the radical $R^6$ in formula I is hydrogen.

Amongst the compounds of embodiments Ia, Ib, Ic, Id, Ie, If, Ig and Ih, likewise preference is given to those, where the radical $R^5$ in formula I is methoxy and where the radical $R^6$ in formula I is fluorine, which is located in the 5-position or in the 6-position of the benzene ring.

Amongst the compounds of embodiments Ia, Ib, Ic, Id, Ie, If, Ig and Ih, likewise preference is given to those, where the radical $R^5$ in formula I is difluoromethoxy and where the radical $R^6$ in formula I is hydrogen.

Amongst the compounds of embodiments Ia, Ib, Ic, Id, Ie, If, Ig and Ih, likewise preference is given to those, where the radical $R^5$ in formula I is difluoromethoxy and where the radical $R^6$ in formula I is fluorine, which is located in the 5-position or in the 6-position of the benzene ring.

Amongst the compounds of embodiments Ia, Ib, Ic, Id, Ie, If, Ig and Ih, likewise preference is given to those, where the radical $R^5$ in formula I is chlorine and where the radical $R^6$ in formula I is hydrogen.

Amongst the compounds of embodiments Ia, Ib, Ic, Id, Ie, If, Ig and Ih, likewise preference is given to those, where the radical $R^5$ in formula I is fluorine and where the radical $R^6$ in formula I is hydrogen.

Amongst the compounds of embodiments Ia, Ib, Ic, Id, Ie, If, Ig and Ih, likewise preference is given to those, where the radical $R^5$ in formula I is difluoromethoxy and where the radical $R^6$ in formula I is hydrogen.

A particular preferred embodiment I'a of the invention relates to compounds of the formula I', to their pharmacologically tolerated salts and to the N-oxides thereof, wherein
$R^1$ is hydrogen;
$R^2$ is hydrogen;
$R^3$ is methyl, methoxy, difluoromethoxy or trifluoromethoxy, in particular methyl or methoxy; and
$R^4$ is hydrogen.

A further particular preferred embodiment I'b of the invention relates to compounds of the formula I', to their pharmacologically tolerated salts and to the N-oxides thereof, wherein
$R^1$ is hydrogen;
$R^2$ is methyl;
$R^3$ is methyl, methoxy, difluoromethoxy or trifluoromethoxy, in particular methyl or methoxy; and
$R^4$ is hydrogen.

A further particular preferred embodiment I'c of the invention relates to compounds of the formula I', to their pharmacologically tolerated salts and to the N-oxides thereof, wherein
$R^1$ is hydrogen;
$R^2$ is hydrogen;
$R^3$ is methyl, methoxy, difluoromethoxy or trifluoromethoxy, in particular methyl or methoxy; and
$R^4$ is methyl.

A further particular preferred embodiment I'd of the invention relates to compounds of the formula I', to their pharmacologically tolerated salts and to the N-oxides thereof, wherein
$R^1$ is hydrogen;
$R^2$ is methyl;
$R^3$ is methyl, methoxy, difluoromethoxy or trifluoromethoxy, in particular methyl or methoxy; and
$R^4$ is methyl.

A particular preferred embodiment I'e of the invention relates to compounds of the formula I', to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is hydrogen.

A further particular preferred embodiment I'f of the invention relates to compounds of the formula I', to their pharmacologically tolerated salts and to the N-oxides thereof, wherein
$R^1$ is hydrogen;
$R^2$ is methyl;
$R^3$ is hydrogen or fluorine, in particular hydrogen; and
$R^4$ is hydrogen.

A further particular preferred embodiment I'g of the invention relates to compounds of the formula I', to their pharmacologically tolerated salts and to the N-oxides thereof, wherein
$R^1$ is hydrogen;
$R^2$ is hydrogen;
$R^3$ is hydrogen or fluorine, in particular hydrogen; and
$R^4$ is methyl.

A further particular preferred embodiment I'h of the invention relates to compounds of the formula I', to their pharmacologically tolerated salts and to the N-oxides thereof, wherein
$R^1$ is hydrogen;
$R^2$ is methyl;
$R^3$ is hydrogen or fluorine, in particular hydrogen; and
$R^4$ is methyl.

Amongst the compounds of embodiments I'a, I'b, I'c, I'd, I'e, I'f, I'g and I'h, preference is given to those, where the radicals $R^5$ and $R^6$ in formula I' are both hydrogen.

Amongst the compounds of embodiments I'a, I'b, I'c, I'd, I'e, I'f, I'g and I'h, likewise preference is given to those, where the radical $R^5$ in formula I is hydrogen and where the radical $R^6$ in formula I' is fluorine, which is located in the 5-position or in the 6-position of the benzene ring.

Amongst the compounds of the formula I, in particular amongst the compounds of embodiments Ia, Ib, Ic, Id, Ie, If, Ig and Ih, particular preference is given to those, wherein the $OCHF_2$-radical is located on the benzene ring in the meta-position with respect to X. Amongst these compounds, particular preference is given to those compounds of the formula I, wherein $R^5$ is hydrogen. Amongst these compounds, likewise preference is given to those compounds of the formula I, wherein $R^5$ is different from hydrogen and in particular selected from fluorine, chlorine, methyl, trifluoromethyl, methoxy, difluoromethoxy and trifluoromethoxy and more preferably from methyl, methoxy and difluoromethoxy, and located in the para-position, with respect to X, or in the para-position, with respect to the $OCHF_2$-radical.

Amongst the compounds of the formula I, in particular amongst the compounds of embodiments Ia, Ib, Ic, Id, Ie, If, Ig and Ih, likewise preference is given to those, wherein the $OCHF_2$-radical is located on the benzene ring in the ortho-position with respect to X. Amongst these compounds, particular preference is given to those compounds of the formula I, wherein $R^5$ is hydrogen. Amongst these compounds, likewise preference is given to those compounds of the formula I, wherein $R^5$ is different from hydrogen and in particular selected from fluorine, chlorine, methyl, trifluoromethyl, methoxy, difluoromethoxy and trifluoromethoxy and more preferably from methyl, methoxy and difluoromethoxy, and located in the para-position, with respect to X, or in the para-position, with respect to the $OCHF_2$-radical.

Amongst the compounds of the formula I, in particular amongst the compounds of embodiments Ia, Ib, Ic, Id, Ie, If, Ig and Ih, likewise preference is given to those, wherein the $OCHF_2$-radical is located on the benzene ring in the para-position with respect to X. Amongst these compounds, particular preference is given to those compounds of the formula I, wherein $R^5$ is hydrogen. Amongst these compounds, likewise preference is given to those compounds of the formula I, wherein $R^5$ is different from hydrogen and in particular selected from fluorine, chlorine, methyl, trifluoromethyl, methoxy, difluoromethoxy and trifluoromethoxy and more preferably from methyl, methoxy and difluoromethoxy, and located in the meta-position, with respect to X.

Amongst the compounds of the formula I', in particular amongst the compounds of embodiments I'a, I'b, I'c, I'd, I'e, I'f and I'g, particular preference is given to those, wherein X is attached to the benzene ring in the α-position with respect to the 1,3-dioxole ring. Amongst these compounds, particular preference is given to those compounds of the formula I', wherein $R^5$ is hydrogen.

Amongst the compounds of the formula I', in particular amongst the compounds of embodiments I'a, I'b, I'c, I'd, I'e, I'f and I'g, particular preference is given to those, wherein X is attached to the benzene ring in the β-position with respect to the 1,3-dioxole ring. Amongst these compounds, particular preference is given to those compounds of the formula I', wherein $R^5$ is hydrogen.

A particular preferred embodiment of the invention relates to compounds of the formula I or I', to their pharmacologically tolerated salts and to the N-oxides thereof, wherein
X is a bond or a group N—$R^4$;
$R^1$ is hydrogen or methyl;
$R^2$ is hydrogen or methyl, in particular hydrogen;
$R^3$ is hydrogen, $C_1$-$C_2$ alkyl, fluorine, $C_1$-$C_2$ alkoxy or fluorinated $C_1$-$C_2$ alkoxy, preferably hydrogen, methyl, methoxy, difluoromethoxy or trifluoromethoxy, in particular hydrogen, methyl or methoxy;
$R^4$ is hydrogen, methyl, ethyl, n-propyl, isopropyl or cyclopropylmethyl;
$R^5$ is hydrogen, fluorine, chlorine, methyl, trifluoromethyl, methoxy, difluoromethoxy and trifluoromethoxy and more preferably hydrogen, methyl or methoxy;
$R^6$ is hydrogen or fluorine, which is located in the 5- or 6-position of the benzene ring; and
n is 1 or 2.

A further particular preferred embodiment of the invention relates to compounds of the formula I or I', to their pharmacologically tolerated salts and to the N-oxides thereof, wherein
X is a bond or a group N—$R^4$;
$R^1$ is hydrogen or methyl, preferably hydrogen;
$R^2$ is hydrogen;
$R^3$ is hydrogen, $C_1$-$C_2$ alkyl or $C_1$-$C_2$ alkoxy, preferably hydrogen, methyl or methoxy, in particular methyl or methoxy;
$R^4$ is hydrogen, methyl, ethyl, n-propyl, isopropyl or cyclopropylmethyl, preferably hydrogen;
$R^5$ is hydrogen, chlorine, fluorine, difluoromethoxy, methyl or methoxy, preferably hydrogen, methyl or methoxy, in particular hydrogen;
$R^6$ is hydrogen; and
n is 1 or 2, preferably 1.

A further particular preferred embodiment of the invention relates to compounds of the formula I or I', to their pharmacologically tolerated salts and to the N-oxides thereof, wherein
X is a group N—$R^4$;
$R^1$ is hydrogen;
$R^2$ is hydrogen;
$R^3$ is $C_1$-$C_2$ alkyl or $C_1$-$C_2$ alkoxy, preferably methyl or methoxy;
$R^4$ is hydrogen;
$R^5$ is hydrogen;
$R^6$ is hydrogen; and
n is 1.

A further particular preferred embodiment of the invention relates to compounds of the formula I or I', to their pharmacologically tolerated salts and to the N-oxides thereof, wherein
X is a group N—$R^4$;
$R^1$ is hydrogen;
$R^2$ is hydrogen;
$R^3$ is $C_1$-$C_2$ alkyl or $C_1$-$C_2$ alkoxy, preferably methyl or methoxy;
$R^4$ is hydrogen;
$R^5$ is chlorine;
$R^6$ is hydrogen; and
n is 1.

A further particular preferred embodiment of the invention relates to compounds of the formula I or I', to their pharmacologically tolerated salts and to the N-oxides thereof, wherein
X is a group N—$R^4$;
$R^1$ is hydrogen;
$R^2$ is hydrogen;
$R^3$ is $C_1$-$C_2$ alkyl or $C_1$-$C_2$ alkoxy, preferably methyl or methoxy;
$R^4$ is hydrogen;
$R^5$ is fluorine;
$R^6$ is hydrogen; and
n is 1.

A further particular preferred embodiment of the invention relates to compounds of the formula I or I', to their pharmacologically tolerated salts and to the N-oxides thereof, wherein
X is a group N—$R^4$;
$R^1$ is hydrogen;
$R^2$ is hydrogen;
$R^3$ is $C_1$-$C_2$ alkyl or $C_1$-$C_2$ alkoxy, preferably methyl or methoxy;
$R^4$ is hydrogen;
$R^5$ is difluoromethoxy;
$R^6$ is hydrogen; and
n is 1.

Examples of compounds according to the present invention are the compounds of the formula I, their pharmacologically tolerated salts and the N-oxides thereof, wherein $R^6$ is hydrogen, and the meanings of X, $R^1$, $R^2$, $R^3$, $R^4$ and $R^5$ and the position of $R^5$ and of the moiety $OCHF_2$ on the benzene ring is given in the following table A:

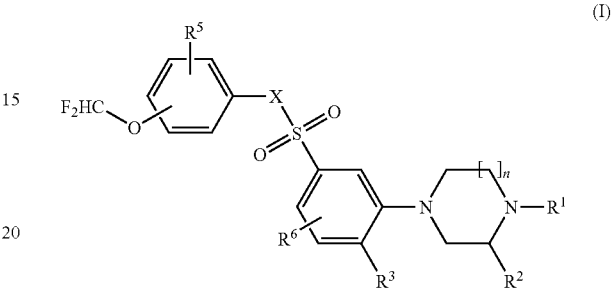

(I)

TABLE A

| No. | n | $R^1$ | $R^2$ | $R^3$ | X | $OCHF_2$* | $R^5$ |
|---|---|---|---|---|---|---|---|
| 1. | 1 | H | H | $OCH_3$ | NH | ortho | H |
| 2. | 1 | H | H | $OCH_3$ | NH | meta | H |
| 3. | 1 | H | H | $OCH_3$ | NH | para | H |
| 4. | 1 | H | H | $OCH_3$ | NH | ortho | $CH_3$ (para to NH) |
| 5. | 1 | H | H | $OCH_3$ | NH | ortho | $CH_3$ (para to $OCHF_2$) |
| 6. | 1 | H | H | $OCH_3$ | NH | meta | $OCH_3$ (para to NH) |
| 7. | 1 | H | H | $OCH_3$ | NH | meta | $OCH_3$ (para to $OCHF_2$) |
| 8. | 1 | H | H | $OCH_3$ | NH | meta | $CH_3$ (para to NH) |
| 9. | 1 | H | H | $OCH_3$ | NH | ortho | Cl (para to NH) |
| 10. | 1 | H | H | $OCH_3$ | NH | ortho | Cl (para to $OCHF_2$) |
| 11. | 1 | H | H | $OCH_3$ | NH | ortho | F (para to NH) |
| 12. | 1 | H | H | $OCH_3$ | NH | ortho | F (para to $OCHF_2$) |
| 13. | 1 | H | H | $OCH_3$ | NH | meta | $OCHF_2$ (para to NH) |
| 14. | 1 | $CH_3$ | H | $OCH_3$ | NH | ortho | H |
| 15. | 1 | $CH_3$ | H | $OCH_3$ | NH | meta | H |
| 16. | 1 | $CH_3$ | H | $OCH_3$ | NH | para | H |
| 17. | 1 | $CH_3$ | H | $OCH_3$ | NH | ortho | $CH_3$ (para to NH) |
| 18. | 1 | $CH_3$ | H | $OCH_3$ | NH | ortho | $CH_3$ (para to $OCHF_2$) |
| 19. | 1 | $CH_3$ | H | $OCH_3$ | NH | meta | $OCH_3$ (para to NH) |
| 20. | 1 | $CH_3$ | H | $OCH_3$ | NH | meta | $OCH_3$ (para to $OCHF_2$) |
| 21. | 1 | $CH_3$ | H | $OCH_3$ | NH | meta | $CH_3$ (para to NH) |
| 22. | 1 | $CH_3$ | H | $OCH_3$ | NH | ortho | Cl (para to NH) |
| 23. | 1 | $CH_3$ | H | $OCH_3$ | NH | ortho | Cl (para to $OCHF_2$) |
| 24. | 1 | $CH_3$ | H | $OCH_3$ | NH | ortho | F (para to NH) |
| 25. | 1 | $CH_3$ | H | $OCH_3$ | NH | ortho | F (para to $OCHF_2$) |
| 26. | 1 | $CH_3$ | H | $OCH_3$ | NH | meta | $OCHF_2$ (para to NH) |
| 27. | 1 | H | H | $OCH_3$ | $NCH_3$ | ortho | H |
| 28. | 1 | H | H | $OCH_3$ | $NCH_3$ | meta | H |
| 29. | 1 | H | H | $OCH_3$ | $NCH_3$ | para | H |
| 30. | 1 | H | H | $OCH_3$ | $NCH_3$ | ortho | $CH_3$ (para to X) |
| 31. | 1 | H | H | $OCH_3$ | $NCH_3$ | ortho | $CH_3$ (para to $OCHF_2$) |
| 32. | 1 | H | H | $OCH_3$ | $NCH_3$ | meta | $OCH_3$ (para to X) |
| 33. | 1 | H | H | $OCH_3$ | $NCH_3$ | meta | $OCH_3$ (para to $OCHF_2$) |
| 34. | 1 | H | H | $OCH_3$ | $NCH_3$ | meta | $CH_3$ (para to X) |
| 35. | 1 | H | H | $OCH_3$ | $NCH_3$ | ortho | Cl (para to X) |
| 36. | 1 | H | H | $OCH_3$ | $NCH_3$ | ortho | Cl (para to $OCHF_2$) |
| 37. | 1 | H | H | $OCH_3$ | $NCH_3$ | ortho | F (para to X) |
| 38. | 1 | H | H | $OCH_3$ | $NCH_3$ | ortho | F (para to $OCHF_2$) |
| 39. | 1 | H | H | $OCH_3$ | $NCH_3$ | meta | $OCHF_2$ (para to X) |
| 40. | 1 | $CH_3$ | H | $OCH_3$ | $NCH_3$ | ortho | H |
| 41. | 1 | $CH_3$ | H | $OCH_3$ | $NCH_3$ | meta | H |
| 42. | 1 | $CH_3$ | H | $OCH_3$ | $NCH_3$ | para | H |
| 43. | 1 | $CH_3$ | H | $OCH_3$ | $NCH_3$ | ortho | $CH_3$ (para to X) |
| 44. | 1 | $CH_3$ | H | $OCH_3$ | $NCH_3$ | ortho | $CH_3$ (para to $OCHF_2$) |
| 45. | 1 | $CH_3$ | H | $OCH_3$ | $NCH_3$ | meta | $OCH_3$ (para to X) |
| 46. | 1 | $CH_3$ | H | $OCH_3$ | $NCH_3$ | meta | $OCH_3$ (para to $OCHF_2$) |
| 47. | 1 | $CH_3$ | H | $OCH_3$ | $NCH_3$ | meta | $CH_3$ (para to X) |
| 48. | 1 | $CH_3$ | H | $OCH_3$ | $NCH_3$ | ortho | Cl (para to X) |

TABLE A-continued

| No. | n | R¹ | R² | R³ | X | OCHF$_2$* | R⁵ |
|---|---|---|---|---|---|---|---|
| 49. | 1 | CH$_3$ | H | OCH$_3$ | NCH$_3$ | ortho | Cl (para to OCHF$_2$) |
| 50. | 1 | CH$_3$ | H | OCH$_3$ | NCH$_3$ | ortho | F (para to X) |
| 51. | 1 | CH$_3$ | H | OCH$_3$ | NCH$_3$ | ortho | F (para to OCHF$_2$) |
| 52. | 1 | CH$_3$ | H | OCH$_3$ | NCH$_3$ | meta | OCHF$_2$ (para to X) |
| 53. | 1 | H | H | OCH$_3$ | NCH$_2$CH$_3$ | ortho | H |
| 54. | 1 | H | H | OCH$_3$ | NCH$_2$CH$_3$ | meta | H |
| 55. | 1 | H | H | OCH$_3$ | NCH$_2$CH$_3$ | para | H |
| 56. | 1 | H | H | OCH$_3$ | NCH$_2$CH$_3$ | ortho | CH$_3$ (para to X) |
| 57. | 1 | H | H | OCH$_3$ | NCH$_2$CH$_3$ | ortho | CH$_3$ (para to OCHF$_2$) |
| 58. | 1 | H | H | OCH$_3$ | NCH$_2$CH$_3$ | meta | OCH$_3$ (para to X) |
| 59. | 1 | H | H | OCH$_3$ | NCH$_2$CH$_3$ | meta | OCH$_3$ (para to OCHF$_2$) |
| 60. | 1 | H | H | OCH$_3$ | NCH$_2$CH$_3$ | meta | CH$_3$ (para to X) |
| 61. | 1 | CH$_3$ | H | OCH$_3$ | NCH$_2$CH$_3$ | ortho | H |
| 62. | 1 | CH$_3$ | H | OCH$_3$ | NCH$_2$CH$_3$ | meta | H |
| 63. | 1 | CH$_3$ | H | OCH$_3$ | NCH$_2$CH$_3$ | para | H |
| 64. | 1 | CH$_3$ | H | OCH$_3$ | NCH$_2$CH$_3$ | ortho | CH$_3$ (para to X) |
| 65. | 1 | CH$_3$ | H | OCH$_3$ | NCH$_2$CH$_3$ | ortho | CH$_3$ (para to OCHF$_2$) |
| 66. | 1 | CH$_3$ | H | OCH$_3$ | NCH$_2$CH$_3$ | meta | OCH$_3$ (para to X) |
| 67. | 1 | CH$_3$ | H | OCH$_3$ | NCH$_2$CH$_3$ | meta | OCH$_3$ (para to OCHF$_2$) |
| 68. | 1 | CH$_3$ | H | OCH$_3$ | NCH$_2$CH$_3$ | meta | CH$_3$ (para to X) |
| 69. | 1 | H | H | OCH$_3$ | N(CH$_2$)$_2$CH$_3$ | ortho | H |
| 70. | 1 | H | H | OCH$_3$ | N(CH$_2$)$_2$CH$_3$ | meta | H |
| 71. | 1 | H | H | OCH$_3$ | N(CH$_2$)$_2$CH$_3$ | para | H |
| 72. | 1 | H | H | OCH$_3$ | N(CH$_2$)$_2$CH$_3$ | ortho | CH$_3$ (para to X) |
| 73. | 1 | H | H | OCH$_3$ | N(CH$_2$)$_2$CH$_3$ | ortho | CH$_3$ (para to OCHF$_2$) |
| 74. | 1 | H | H | OCH$_3$ | N(CH$_2$)$_2$CH$_3$ | meta | OCH$_3$ (para to X) |
| 75. | 1 | H | H | OCH$_3$ | N(CH$_2$)$_2$CH$_3$ | meta | OCH$_3$ (para to OCHF$_2$) |
| 76. | 1 | H | H | OCH$_3$ | N(CH$_2$)$_2$CH$_3$ | meta | CH$_3$ (para to X) |
| 77. | 1 | CH$_3$ | H | OCH$_3$ | N(CH$_2$)$_2$CH$_3$ | ortho | H |
| 78. | 1 | CH$_3$ | H | OCH$_3$ | N(CH$_2$)$_2$CH$_3$ | meta | H |
| 79. | 1 | CH$_3$ | H | OCH$_3$ | N(CH$_2$)$_2$CH$_3$ | para | H |
| 80. | 1 | CH$_3$ | H | OCH$_3$ | N(CH$_2$)$_2$CH$_3$ | ortho | CH$_3$ (para to X) |
| 81. | 1 | CH$_3$ | H | OCH$_3$ | N(CH$_2$)$_2$CH$_3$ | ortho | CH$_3$ (para to OCHF$_2$) |
| 82. | 1 | CH$_3$ | H | OCH$_3$ | N(CH$_2$)$_2$CH$_3$ | meta | OCH$_3$ (para to X) |
| 83. | 1 | CH$_3$ | H | OCH$_3$ | N(CH$_2$)$_2$CH$_3$ | meta | OCH$_3$ (para to OCHF$_2$) |
| 84. | 1 | CH$_3$ | H | OCH$_3$ | N(CH$_2$)$_2$CH$_3$ | meta | CH$_3$ (para to X) |
| 85. | 1 | H | H | OCH$_3$ | N(CH$_2$)-cyclopropyl | ortho | H |
| 86. | 1 | H | H | OCH$_3$ | N(CH$_2$)-cyclopropyl | meta | H |
| 87. | 1 | H | H | OCH$_3$ | N(CH$_2$)-cyclopropyl | para | H |
| 88. | 1 | H | H | OCH$_3$ | N(CH$_2$)-cyclopropyl | ortho | CH$_3$ (para to X) |
| 89. | 1 | H | H | OCH$_3$ | N(CH$_2$)-cyclopropyl | ortho | CH$_3$ (para to OCHF$_2$) |
| 90. | 1 | H | H | OCH$_3$ | N(CH$_2$)-cyclopropyl | meta | OCH$_3$ (para to X) |
| 91. | 1 | H | H | OCH$_3$ | N(CH$_2$)-cyclopropyl | meta | OCH$_3$ (para to OCHF$_2$) |
| 92. | 1 | H | H | OCH$_3$ | N(CH$_2$)-cyclopropyl | meta | CH$_3$ (para to X) |
| 93. | 1 | CH$_3$ | H | OCH$_3$ | N(CH$_2$)-cyclopropyl | ortho | H |
| 94. | 1 | CH$_3$ | H | OCH$_3$ | N(CH$_2$)-cyclopropyl | meta | H |
| 95. | 1 | CH$_3$ | H | OCH$_3$ | N(CH$_2$)-cyclopropyl | para | H |
| 96. | 1 | CH$_3$ | H | OCH$_3$ | N(CH$_2$)-cyclopropyl | ortho | CH$_3$ (para to X) |
| 97. | 1 | CH$_3$ | H | OCH$_3$ | N(CH$_2$)-cyclopropyl | ortho | CH$_3$ (para to OCHF$_2$) |
| 98. | 1 | CH$_3$ | H | OCH$_3$ | N(CH$_2$)-cyclopropyl | meta | OCH$_3$ (para to X) |
| 99. | 1 | CH$_3$ | H | OCH$_3$ | N(CH$_2$)-cyclopropyl | meta | OCH$_3$ (para to OCHF$_2$) |
| 100. | 1 | CH$_3$ | H | OCH$_3$ | N(CH$_2$)-cyclopropyl | meta | CH$_3$ (para to X) |
| 101. | 1 | H | H | OCH$_3$ | bond | ortho | H |
| 102. | 1 | H | H | OCH$_3$ | bond | meta | H |
| 103. | 1 | H | H | OCH$_3$ | bond | para | H |
| 104. | 1 | H | H | OCH$_3$ | bond | ortho | CH$_3$ (para to X) |
| 105. | 1 | H | H | OCH$_3$ | bond | ortho | CH$_3$ (para to OCHF$_2$) |
| 106. | 1 | H | H | OCH$_3$ | bond | meta | OCH$_3$ (para to X) |
| 107. | 1 | H | H | OCH$_3$ | bond | meta | OCH$_3$ (para to OCHF$_2$) |
| 108. | 1 | H | H | OCH$_3$ | bond | meta | CH$_3$ (para to X) |
| 109. | 1 | CH$_3$ | H | OCH$_3$ | bond | ortho | H |
| 110. | 1 | CH$_3$ | H | OCH$_3$ | bond | meta | H |
| 111. | 1 | CH$_3$ | H | OCH$_3$ | bond | para | H |
| 112. | 1 | CH$_3$ | H | OCH$_3$ | bond | ortho | CH$_3$ (para to X) |
| 113. | 1 | CH$_3$ | H | OCH$_3$ | bond | ortho | CH$_3$ (para to OCHF$_2$) |
| 114. | 1 | CH$_3$ | H | OCH$_3$ | bond | meta | OCH$_3$ (para to X) |
| 115. | 1 | CH$_3$ | H | OCH$_3$ | bond | meta | OCH$_3$ (para to OCHF$_2$) |
| 116. | 1 | CH$_3$ | H | OCH$_3$ | bond | meta | CH$_3$ (para to X) |
| 117. | 2 | H | H | OCH$_3$ | NH | ortho | H |
| 118. | 2 | H | H | OCH$_3$ | NH | meta | H |
| 119. | 2 | H | H | OCH$_3$ | NH | para | H |
| 120. | 2 | H | H | OCH$_3$ | NH | ortho | CH$_3$ (para to NH) |
| 121. | 2 | H | H | OCH$_3$ | NH | ortho | CH$_3$ (para to OCHF$_2$) |
| 122. | 2 | H | H | OCH$_3$ | NH | meta | OCH$_3$ (para to NH) |
| 123. | 2 | H | H | OCH$_3$ | NH | meta | OCH$_3$ (para to OCHF$_2$) |
| 124. | 2 | H | H | OCH$_3$ | NH | meta | CH$_3$ (para to NH) |
| 125. | 2 | H | H | OCH$_3$ | NH | ortho | Cl (para to NH) |
| 126. | 2 | H | H | OCH$_3$ | NH | ortho | Cl (para to OCHF$_2$) |

TABLE A-continued

| No. | n | R$^1$ | R$^2$ | R$^3$ | X | OCHF$_2$* | R$^5$ |
|---|---|---|---|---|---|---|---|
| 127. | 2 | H | H | OCH$_3$ | NH | ortho | F (para to NH) |
| 128. | 2 | H | H | OCH$_3$ | NH | ortho | F (para to OCHF$_2$) |
| 129. | 2 | H | H | OCH$_3$ | NH | meta | OCHF$_2$ (para to NH) |
| 130. | 2 | CH$_3$ | H | OCH$_3$ | NH | ortho | H |
| 131. | 2 | CH$_3$ | H | OCH$_3$ | NH | meta | H |
| 132. | 2 | CH$_3$ | H | OCH$_3$ | NH | para | H |
| 133. | 2 | CH$_3$ | H | OCH$_3$ | NH | ortho | CH$_3$ (para to NH) |
| 134. | 2 | CH$_3$ | H | OCH$_3$ | NH | ortho | CH$_3$ (para to OCHF$_2$) |
| 135. | 2 | CH$_3$ | H | OCH$_3$ | NH | meta | OCH$_3$ (para to NH) |
| 136. | 2 | CH$_3$ | H | OCH$_3$ | NH | meta | OCH$_3$ (para to OCHF$_2$) |
| 137. | 2 | CH$_3$ | H | OCH$_3$ | NH | meta | CH$_3$ (para to NH) |
| 138. | 2 | CH$_3$ | H | OCH$_3$ | NH | ortho | Cl (para to NH) |
| 139. | 2 | CH$_3$ | H | OCH$_3$ | NH | ortho | Cl (para to OCHF$_2$) |
| 140. | 2 | CH$_3$ | H | OCH$_3$ | NH | ortho | F (para to NH) |
| 141. | 2 | CH$_3$ | H | OCH$_3$ | NH | ortho | F (para to OCHF$_2$) |
| 142. | 2 | CH$_3$ | H | OCH$_3$ | NH | meta | OCHF$_2$ (para to NH) |
| 143. | 2 | H | H | OCH$_3$ | NCH$_3$ | ortho | H |
| 144. | 2 | H | H | OCH$_3$ | NCH$_3$ | meta | H |
| 145. | 2 | H | H | OCH$_3$ | NCH$_3$ | para | H |
| 146. | 2 | H | H | OCH$_3$ | NCH$_3$ | ortho | CH$_3$ (para to X) |
| 147. | 2 | H | H | OCH$_3$ | NCH$_3$ | ortho | CH$_3$ (para to OCHF$_2$) |
| 148. | 2 | H | H | OCH$_3$ | NCH$_3$ | meta | OCH$_3$ (para to X) |
| 149. | 2 | H | H | OCH$_3$ | NCH$_3$ | meta | OCH$_3$ (para to OCHF$_2$) |
| 150. | 2 | H | H | OCH$_3$ | NCH$_3$ | meta | CH$_3$ (para to X) |
| 151. | 2 | H | H | OCH$_3$ | NCH$_3$ | ortho | Cl (para to X) |
| 152. | 2 | H | H | OCH$_3$ | NCH$_3$ | ortho | Cl (para to OCHF$_2$) |
| 153. | 2 | H | H | OCH$_3$ | NCH$_3$ | ortho | F (para to X) |
| 154. | 2 | H | H | OCH$_3$ | NCH$_3$ | ortho | F (para to OCHF$_2$) |
| 155. | 2 | H | H | OCH$_3$ | NCH$_3$ | meta | OCHF$_2$ (para to X) |
| 156. | 2 | CH$_3$ | H | OCH$_3$ | NCH$_3$ | ortho | H |
| 157. | 2 | CH$_3$ | H | OCH$_3$ | NCH$_3$ | meta | H |
| 158. | 2 | CH$_3$ | H | OCH$_3$ | NCH$_3$ | para | H |
| 159. | 2 | CH$_3$ | H | OCH$_3$ | NCH$_3$ | ortho | CH$_3$ (para to X) |
| 160. | 2 | CH$_3$ | H | OCH$_3$ | NCH$_3$ | ortho | CH$_3$ (para to OCHF$_2$) |
| 161. | 2 | CH$_3$ | H | OCH$_3$ | NCH$_3$ | meta | OCH$_3$ (para to X) |
| 162. | 2 | CH$_3$ | H | OCH$_3$ | NCH$_3$ | meta | OCH$_3$ (para to OCHF$_2$) |
| 163. | 2 | CH$_3$ | H | OCH$_3$ | NCH$_3$ | meta | CH$_3$ (para to X) |
| 164. | 2 | CH$_3$ | H | OCH$_3$ | NCH$_3$ | ortho | Cl (para to X) |
| 165. | 2 | CH$_3$ | H | OCH$_3$ | NCH$_3$ | ortho | Cl (para to OCHF$_2$) |
| 166. | 2 | CH$_3$ | H | OCH$_3$ | NCH$_3$ | ortho | F (para to X) |
| 167. | 2 | CH$_3$ | H | OCH$_3$ | NCH$_3$ | ortho | F (para to OCHF$_2$) |
| 168. | 2 | CH$_3$ | H | OCH$_3$ | NCH$_3$ | meta | OCHF$_2$ (para to X) |
| 169. | 2 | H | H | OCH$_3$ | NCH$_2$CH$_3$ | ortho | H |
| 170. | 2 | H | H | OCH$_3$ | NCH$_2$CH$_3$ | meta | H |
| 171. | 2 | H | H | OCH$_3$ | NCH$_2$CH$_3$ | para | H |
| 172. | 2 | H | H | OCH$_3$ | NCH$_2$CH$_3$ | ortho | CH$_3$ (para to X) |
| 173. | 2 | H | H | OCH$_3$ | NCH$_2$CH$_3$ | ortho | CH$_3$ (para to OCHF$_2$) |
| 174. | 2 | H | H | OCH$_3$ | NCH$_2$CH$_3$ | meta | OCH$_3$ (para to X) |
| 175. | 2 | H | H | OCH$_3$ | NCH$_2$CH$_3$ | meta | OCH$_3$ (para to OCHF$_2$) |
| 176. | 2 | H | H | OCH$_3$ | NCH$_2$CH$_3$ | meta | CH$_3$ (para to X) |
| 177. | 2 | CH$_3$ | H | OCH$_3$ | NCH$_2$CH$_3$ | ortho | H |
| 178. | 2 | CH$_3$ | H | OCH$_3$ | NCH$_2$CH$_3$ | meta | H |
| 179. | 2 | CH$_3$ | H | OCH$_3$ | NCH$_2$CH$_3$ | para | H |
| 180. | 2 | CH$_3$ | H | OCH$_3$ | NCH$_2$CH$_3$ | ortho | CH$_3$ (para to X) |
| 181. | 2 | CH$_3$ | H | OCH$_3$ | NCH$_2$CH$_3$ | ortho | CH$_3$ (para to OCHF$_2$) |
| 182. | 2 | CH$_3$ | H | OCH$_3$ | NCH$_2$CH$_3$ | meta | OCH$_3$ (para to X) |
| 183. | 2 | CH$_3$ | H | OCH$_3$ | NCH$_2$CH$_3$ | meta | OCH$_3$ (para to OCHF$_2$) |
| 184. | 2 | CH$_3$ | H | OCH$_3$ | NCH$_2$CH$_3$ | meta | CH$_3$ (para to X) |
| 185. | 2 | H | H | OCH$_3$ | N(CH$_2$)$_2$CH$_3$ | ortho | H |
| 186. | 2 | H | H | OCH$_3$ | N(CH$_2$)$_2$CH$_3$ | meta | H |
| 187. | 2 | H | H | OCH$_3$ | N(CH$_2$)$_2$CH$_3$ | para | H |
| 188. | 2 | H | H | OCH$_3$ | N(CH$_2$)$_2$CH$_3$ | ortho | CH$_3$ (para to X) |
| 189. | 2 | H | H | OCH$_3$ | N(CH$_2$)$_2$CH$_3$ | ortho | CH$_3$ (para to OCHF$_2$) |
| 190. | 2 | H | H | OCH$_3$ | N(CH$_2$)$_2$CH$_3$ | meta | OCH$_3$ (para to X) |
| 191. | 2 | H | H | OCH$_3$ | N(CH$_2$)$_2$CH$_3$ | meta | OCH$_3$ (para to OCHF$_2$) |
| 192. | 2 | H | H | OCH$_3$ | N(CH$_2$)$_2$CH$_3$ | meta | CH$_3$ (para to X) |
| 193. | 2 | CH$_3$ | H | OCH$_3$ | N(CH$_2$)$_2$CH$_3$ | ortho | H |
| 194. | 2 | CH$_3$ | H | OCH$_3$ | N(CH$_2$)$_2$CH$_3$ | meta | H |
| 195. | 2 | CH$_3$ | H | OCH$_3$ | N(CH$_2$)$_2$CH$_3$ | para | H |
| 196. | 2 | CH$_3$ | H | OCH$_3$ | N(CH$_2$)$_2$CH$_3$ | ortho | CH$_3$ (para to X) |
| 197. | 2 | CH$_3$ | H | OCH$_3$ | N(CH$_2$)$_2$CH$_3$ | ortho | CH$_3$ (para to OCHF$_2$) |
| 198. | 2 | CH$_3$ | H | OCH$_3$ | N(CH$_2$)$_2$CH$_3$ | meta | OCH$_3$ (para to X) |
| 199. | 2 | CH$_3$ | H | OCH$_3$ | N(CH$_2$)$_2$CH$_3$ | meta | OCH$_3$ (para to OCHF$_2$) |
| 200. | 2 | CH$_3$ | H | OCH$_3$ | N(CH$_2$)$_2$CH$_3$ | meta | CH$_3$ (para to X) |
| 201. | 2 | H | H | OCH$_3$ | N(CH$_2$)-cyclopropyl | ortho | H |
| 202. | 2 | H | H | OCH$_3$ | N(CH$_2$)-cyclopropyl | meta | H |
| 203. | 2 | H | H | OCH$_3$ | N(CH$_2$)-cyclopropyl | para | H |
| 204. | 2 | H | H | OCH$_3$ | N(CH$_2$)-cyclopropyl | ortho | CH$_3$ (para to X) |

TABLE A-continued

| No. | n | R¹ | R² | R³ | X | OCHF₂* | R⁵ |
|---|---|---|---|---|---|---|---|
| 205. | 2 | H | H | OCH₃ | N(CH₂)-cyclopropyl | ortho | CH₃ (para to OCHF₂) |
| 206. | 2 | H | H | OCH₃ | N(CH₂)-cyclopropyl | meta | OCH₃ (para to X) |
| 207. | 2 | H | H | OCH₃ | N(CH₂)-cyclopropyl | meta | OCH₃ (para to OCHF₂) |
| 208. | 2 | H | H | OCH₃ | N(CH₂)-cyclopropyl | meta | CH₃ (para to X) |
| 209. | 2 | CH₃ | H | OCH₃ | N(CH₂)-cyclopropyl | mrtho | H |
| 210. | 2 | CH₃ | H | OCH₃ | N(CH₂)-cyclopropyl | meta | H |
| 211. | 2 | CH₃ | H | OCH₃ | N(CH₂)-cyclopropyl | para | H |
| 212. | 2 | CH₃ | H | OCH₃ | N(CH₂)-cyclopropyl | ortho | CH₃ (para to X) |
| 213. | 2 | CH₃ | H | OCH₃ | N(CH₂)-cyclopropyl | ortho | CH₃ (para to OCHF₂) |
| 214. | 2 | CH₃ | H | OCH₃ | N(CH₂)-cyclopropyl | meta | OCH₃ (para to X) |
| 215. | 2 | CH₃ | H | OCH₃ | N(CH₂)-cyclopropyl | meta | OCH₃ (para to OCHF₂) |
| 216. | 2 | CH₃ | H | OCH₃ | N(CH₂)-cyclopropyl | meta | CH₃ (para to X) |
| 217. | 2 | H | H | OCH₃ | bond | ortho | H |
| 218. | 2 | H | H | OCH₃ | bond | meta | H |
| 219. | 2 | H | H | OCH₃ | bond | para | H |
| 220. | 2 | H | H | OCH₃ | bond | ortho | CH₃ (para to X) |
| 221. | 2 | H | H | OCH₃ | bond | ortho | CH₃ (para to OCHF₂) |
| 222. | 2 | H | H | OCH₃ | bond | meta | OCH₃ (para to X) |
| 223. | 2 | H | H | OCH₃ | bond | meta | OCH₃ (para to OCHF₂) |
| 224. | 2 | H | H | OCH₃ | bond | meta | CH₃ (para to X) |
| 225. | 2 | CH₃ | H | OCH₃ | bond | ortho | H |
| 226. | 2 | CH₃ | H | OCH₃ | bond | meta | H |
| 227. | 2 | CH₃ | H | OCH₃ | bond | para | H |
| 228. | 2 | CH₃ | H | OCH₃ | bond | ortho | CH₃ (para to X) |
| 229. | 2 | CH₃ | H | OCH₃ | bond | ortho | CH₃ (para to OCHF₂) |
| 230. | 2 | CH₃ | H | OCH₃ | bond | meta | OCH₃ (para to X) |
| 231. | 2 | CH₃ | H | OCH₃ | bond | meta | OCH₃ (para to OCHF₂) |
| 232. | 2 | CH₃ | H | OCH₃ | bond | meta | CH₃ (para to X) |
| 233. | 1 | H | H | OCHF₂ | NH | ortho | H |
| 234. | 1 | H | H | OCHF₂ | NH | meta | H |
| 235. | 1 | H | H | OCHF₂ | NH | para | H |
| 236. | 1 | H | H | OCHF₂ | NH | ortho | CH₃ (para to NH) |
| 237. | 1 | H | H | OCHF₂ | NH | ortho | CH₃ (para to OCHF₂) |
| 238. | 1 | H | H | OCHF₂ | NH | meta | OCH₃ (para to NH) |
| 239. | 1 | H | H | OCHF₂ | NH | meta | OCH₃ (para to OCHF₂) |
| 240. | 1 | H | H | OCHF₂ | NH | meta | CH₃ (para to NH) |
| 241. | 1 | H | H | OCHF₂ | NH | ortho | Cl (para to NH) |
| 242. | 1 | H | H | OCHF₂ | NH | ortho | Cl (para to OCHF₂) |
| 243. | 1 | H | H | OCHF₂ | NH | ortho | F (para to NH) |
| 244. | 1 | H | H | OCHF₂ | NH | ortho | F (para to OCHF₂) |
| 245. | 1 | H | H | OCHF₂ | NH | meta | OCHF₂ (para to NH) |
| 246. | 1 | CH₃ | H | OCHF₂ | NH | ortho | H |
| 247. | 1 | CH₃ | H | OCHF₂ | NH | meta | H |
| 248. | 1 | CH₃ | H | OCHF₂ | NH | para | H |
| 249. | 1 | CH₃ | H | OCHF₂ | NH | ortho | CH₃ (para to NH) |
| 250. | 1 | CH₃ | H | OCHF₂ | NH | ortho | CH₃ (para to OCHF₂) |
| 251. | 1 | CH₃ | H | OCHF₂ | NH | meta | OCH₃ (para to NH) |
| 252. | 1 | CH₃ | H | OCHF₂ | NH | meta | OCH₃ (para to OCHF₂) |
| 253. | 1 | CH₃ | H | OCHF₂ | NH | meta | CH₃ (para to NH) |
| 254. | 1 | CH₃ | H | OCHF₂ | NH | ortho | Cl (para to NH) |
| 255. | 1 | CH₃ | H | OCHF₂ | NH | ortho | Cl (para to OCHF₂) |
| 256. | 1 | CH₃ | H | OCHF₂ | NH | ortho | F (para to NH) |
| 257. | 1 | CH₃ | H | OCHF₂ | NH | ortho | F (para to OCHF₂) |
| 258. | 1 | CH₃ | H | OCHF₂ | NH | meta | OCHF₂ (para to NH) |
| 259. | 1 | H | H | OCHF₂ | NCH₃ | ortho | H |
| 260. | 1 | H | H | OCHF₂ | NCH₃ | meta | H |
| 261. | 1 | H | H | OCHF₂ | NCH₃ | para | H |
| 262. | 1 | H | H | OCHF₂ | NCH₃ | ortho | CH₃ (para to X) |
| 263. | 1 | H | H | OCHF₂ | NCH₃ | ortho | CH₃ (para to OCHF₂) |
| 264. | 1 | H | H | OCHF₂ | NCH₃ | meta | OCH₃ (para to X) |
| 265. | 1 | H | H | OCHF₂ | NCH₃ | meta | OCH₃ (para to OCHF₂) |
| 266. | 1 | H | H | OCHF₂ | NCH₃ | meta | CH₃ (para to X) |
| 267. | 1 | H | H | OCHF₂ | NCH₃ | ortho | Cl (para to X) |
| 268. | 1 | H | H | OCHF₂ | NCH₃ | ortho | Cl (para to OCHF₂) |
| 269. | 1 | H | H | OCHF₂ | NCH₃ | ortho | F (para to X) |
| 270. | 1 | H | H | OCHF₂ | NCH₃ | ortho | F (para to OCHF₂) |
| 271. | 1 | H | H | OCHF₂ | NCH₃ | meta | OCHF₂ (para to X) |
| 272. | 1 | CH₃ | H | OCHF₂ | NCH₃ | ortho | H |
| 273. | 1 | CH₃ | H | OCHF₂ | NCH₃ | meta | H |
| 274. | 1 | CH₃ | H | OCHF₂ | NCH₃ | para | H |
| 275. | 1 | CH₃ | H | OCHF₂ | NCH₃ | ortho | CH₃ (para to X) |
| 276. | 1 | CH₃ | H | OCHF₂ | NCH₃ | ortho | CH₃ (para to OCHF₂) |
| 277. | 1 | CH₃ | H | OCHF₂ | NCH₃ | meta | OCH₃ (para to X) |
| 278. | 1 | CH₃ | H | OCHF₂ | NCH₃ | meta | OCH₃ (para to OCHF₂) |
| 279. | 1 | CH₃ | H | OCHF₂ | NCH₃ | meta | CH₃ (para to X) |
| 280. | 1 | CH₃ | H | OCHF₂ | NCH₃ | ortho | Cl (para to X) |
| 281. | 1 | CH₃ | H | OCHF₂ | NCH₃ | ortho | Cl (para to OCHF₂) |
| 282. | 1 | CH₃ | H | OCHF₂ | NCH₃ | ortho | F (para to X) |

TABLE A-continued

| No. | n | $R^1$ | $R^2$ | $R^3$ | X | $OCHF_2$* | $R^5$ |
|---|---|---|---|---|---|---|---|
| 283. | 1 | $CH_3$ | H | $OCHF_2$ | $NCH_3$ | ortho | F (para to $OCHF_2$) |
| 284. | 1 | $CH_3$ | H | $OCHF_2$ | $NCH_3$ | meta | $OCHF_2$ (para to X) |
| 285. | 1 | H | H | $OCHF_2$ | $NCH_2CH_3$ | ortho | H |
| 286. | 1 | H | H | $OCHF_2$ | $NCH_2CH_3$ | meta | H |
| 287. | 1 | H | H | $OCHF_2$ | $NCH_2CH_3$ | para | H |
| 288. | 1 | H | H | $OCHF_2$ | $NCH_2CH_3$ | ortho | $CH_3$ (para to X) |
| 289. | 1 | H | H | $OCHF_2$ | $NCH_2CH_3$ | ortho | $CH_3$ (para to $OCHF_2$) |
| 290. | 1 | H | H | $OCHF_2$ | $NCH_2CH_3$ | meta | $OCH_3$ (para to X) |
| 291. | 1 | H | H | $OCHF_2$ | $NCH_2CH_3$ | meta | $OCH_3$ (para to $OCHF_2$) |
| 292. | 1 | H | H | $OCHF_2$ | $NCH_2CH_3$ | meta | $CH_3$ (para to X) |
| 293. | 1 | $CH_3$ | H | $OCHF_2$ | $NCH_2CH_3$ | ortho | H |
| 294. | 1 | $CH_3$ | H | $OCHF_2$ | $NCH_2CH_3$ | meta | H |
| 295. | 1 | $CH_3$ | H | $OCHF_2$ | $NCH_2CH_3$ | para | H |
| 296. | 1 | $CH_3$ | H | $OCHF_2$ | $NCH_2CH_3$ | ortho | $CH_3$ (para to X) |
| 297. | 1 | $CH_3$ | H | $OCHF_2$ | $NCH_2CH_3$ | ortho | $CH_3$ (para to $OCHF_2$) |
| 298. | 1 | $CH_3$ | H | $OCHF_2$ | $NCH_2CH_3$ | meta | $OCH_3$ (para to X) |
| 299. | 1 | $CH_3$ | H | $OCHF_2$ | $NCH_2CH_3$ | meta | $OCH_3$ (para to $OCHF_2$) |
| 300. | 1 | $CH_3$ | H | $OCHF_2$ | $NCH_2CH_3$ | meta | $CH_3$ (para to X) |
| 301. | 1 | H | H | $OCHF_2$ | $N(CH_2)_2CH_3$ | ortho | H |
| 302. | 1 | H | H | $OCHF_2$ | $N(CH_2)_2CH_3$ | meta | H |
| 303. | 1 | H | H | $OCHF_2$ | $N(CH_2)_2CH_3$ | para | H |
| 304. | 1 | H | H | $OCHF_2$ | $N(CH_2)_2CH_3$ | ortho | $CH_3$ (para to X) |
| 305. | 1 | H | H | $OCHF_2$ | $N(CH_2)_2CH_3$ | ortho | $CH_3$ (para to $OCHF_2$) |
| 306. | 1 | H | H | $OCHF_2$ | $N(CH_2)_2CH_3$ | meta | $OCH_3$ (para to X) |
| 307. | 1 | H | H | $OCHF_2$ | $N(CH_2)_2CH_3$ | meta | $OCH_3$ (para to $OCHF_2$) |
| 308. | 1 | H | H | $OCHF_2$ | $N(CH_2)_2CH_3$ | meta | $CH_3$ (para to X) |
| 309. | 1 | $CH_3$ | H | $OCHF_2$ | $N(CH_2)_2CH_3$ | ortho | H |
| 310. | 1 | $CH_3$ | H | $OCHF_2$ | $N(CH_2)_2CH_3$ | meta | H |
| 311. | 1 | $CH_3$ | H | $OCHF_2$ | $N(CH_2)_2CH_3$ | para | H |
| 312. | 1 | $CH_3$ | H | $OCHF_2$ | $N(CH_2)_2CH_3$ | ortho | $CH_3$ (para to X) |
| 313. | 1 | $CH_3$ | H | $OCHF_2$ | $N(CH_2)_2CH_3$ | ortho | $CH_3$ (para to $OCHF_2$) |
| 314. | 1 | $CH_3$ | H | $OCHF_2$ | $N(CH_2)_2CH_3$ | meta | $OCH_3$ (para to X) |
| 315. | 1 | $CH_3$ | H | $OCHF_2$ | $N(CH_2)_2CH_3$ | meta | $OCH_3$ (para to $OCHF_2$) |
| 316. | 1 | $CH_3$ | H | $OCHF_2$ | $N(CH_2)_2CH_3$ | meta | $CH_3$ (para to X) |
| 317. | 1 | H | H | $OCHF_2$ | $N(CH_2)$-cyclopropyl | ortho | H |
| 318. | 1 | H | H | $OCHF_2$ | $N(CH_2)$-cyclopropyl | meta | H |
| 319. | 1 | H | H | $OCHF_2$ | $N(CH_2)$-cyclopropyl | para | H |
| 320. | 1 | H | H | $OCHF_2$ | $N(CH_2)$-cyclopropyl | ortho | $CH_3$ (para to X) |
| 321. | 1 | H | H | $OCHF_2$ | $N(CH_2)$-cyclopropyl | ortho | $CH_3$ (para to $OCHF_2$) |
| 322. | 1 | H | H | $OCHF_2$ | $N(CH_2)$-cyclopropyl | meta | $OCH_3$ (para to X) |
| 323. | 1 | H | H | $OCHF_2$ | $N(CH_2)$-cyclopropyl | meta | $OCH_3$ (para to $OCHF_2$) |
| 324. | 1 | H | H | $OCHF_2$ | $N(CH_2)$-cyclopropyl | meta | $CH_3$ (para to X) |
| 325. | 1 | $CH_3$ | H | $OCHF_2$ | $N(CH_2)$-cyclopropyl | ortho | H |
| 326. | 1 | $CH_3$ | H | $OCHF_2$ | $N(CH_2)$-cyclopropyl | meta | H |
| 327. | 1 | $CH_3$ | H | $OCHF_2$ | $N(CH_2)$-cyclopropyl | para | H |
| 328. | 1 | $CH_3$ | H | $OCHF_2$ | $N(CH_2)$-cyclopropyl | ortho | $CH_3$ (para to X) |
| 329. | 1 | $CH_3$ | H | $OCHF_2$ | $N(CH_2)$-cyclopropyl | ortho | $CH_3$ (para to $OCHF_2$) |
| 330. | 1 | $CH_3$ | H | $OCHF_2$ | $N(CH_2)$-cyclopropyl | meta | $OCH_3$ (para to X) |
| 331. | 1 | $CH_3$ | H | $OCHF_2$ | $N(CH_2)$-cyclopropyl | meta | $OCH_3$ (para to $OCHF_2$) |
| 332. | 1 | $CH_3$ | H | $OCHF_2$ | $N(CH_2)$-cyclopropyl | meta | $CH_3$ (para to X) |
| 333. | 1 | H | H | $OCHF_2$ | bond | ortho | H |
| 334. | 1 | H | H | $OCHF_2$ | bond | meta | H |
| 335. | 1 | H | H | $OCHF_2$ | bond | para | H |
| 336. | 1 | H | H | $OCHF_2$ | bond | ortho | $CH_3$ (para to X) |
| 337. | 1 | H | H | $OCHF_2$ | bond | ortho | $CH_3$ (para to $OCHF_2$) |
| 338. | 1 | H | H | $OCHF_2$ | bond | meta | $OCH_3$ (para to X) |
| 339. | 1 | H | H | $OCHF_2$ | bond | meta | $OCH_3$ (para to $OCHF_2$) |
| 340. | 1 | H | H | $OCHF_2$ | bond | meta | $CH_3$ (para to X) |
| 341. | 1 | $CH_3$ | H | $OCHF_2$ | bond | ortho | H |
| 342. | 1 | $CH_3$ | H | $OCHF_2$ | bond | meta | H |
| 343. | 1 | $CH_3$ | H | $OCHF_2$ | bond | para | H |
| 344. | 1 | $CH_3$ | H | $OCHF_2$ | bond | ortho | $CH_3$ (para to X) |
| 345. | 1 | $CH_3$ | H | $OCHF_2$ | bond | ortho | $CH_3$ (para to $OCHF_2$) |
| 346. | 1 | $CH_3$ | H | $OCHF_2$ | bond | meta | $OCH_3$ (para to X) |
| 347. | 1 | $CH_3$ | H | $OCHF_2$ | bond | meta | $OCH_3$ (para to $OCHF_2$) |
| 348. | 1 | $CH_3$ | H | $OCHF_2$ | bond | meta | $CH_3$ (para to X) |
| 349. | 2 | H | H | $OCHF_2$ | NH | ortho | H |
| 350. | 2 | H | H | $OCHF_2$ | NH | meta | H |
| 351. | 2 | H | H | $OCHF_2$ | NH | para | H |
| 352. | 2 | H | H | $OCHF_2$ | NH | ortho | $CH_3$ (para to NH) |
| 353. | 2 | H | H | $OCHF_2$ | NH | ortho | $CH_3$ (para to $OCHF_2$) |
| 354. | 2 | H | H | $OCHF_2$ | NH | meta | $OCH_3$ (para to NH) |
| 355. | 2 | H | H | $OCHF_2$ | NH | meta | $OCH_3$ (para to $OCHF_2$) |
| 356. | 2 | H | H | $OCHF_2$ | NH | meta | $CH_3$ (para to NH) |
| 357. | 2 | H | H | $OCHF_2$ | NH | ortho | Cl (para to NH) |
| 358. | 2 | H | H | $OCHF_2$ | NH | ortho | Cl (para to $OCHF_2$) |
| 359. | 2 | H | H | $OCHF_2$ | NH | ortho | F (para to NH) |
| 360. | 2 | H | H | $OCHF_2$ | NH | ortho | F (para to $OCHF_2$) |

TABLE A-continued

| No. | n | R¹ | R² | R³ | X | OCHF₂* | R⁵ |
|---|---|---|---|---|---|---|---|
| 361. | 2 | H | H | OCHF₂ | NH | meta | OCHF₂ (para to NH) |
| 362. | 2 | CH₃ | H | OCHF₂ | NH | ortho | H |
| 363. | 2 | CH₃ | H | OCHF₂ | NH | meta | H |
| 364. | 2 | CH₃ | H | OCHF₂ | NH | para | H |
| 365. | 2 | CH₃ | H | OCHF₂ | NH | ortho | CH₃ (para to NH) |
| 366. | 2 | CH₃ | H | OCHF₂ | NH | ortho | CH₃ (para to OCHF₂) |
| 367. | 2 | CH₃ | H | OCHF₂ | NH | meta | OCH₃ (para to NH) |
| 368. | 2 | CH₃ | H | OCHF₂ | NH | meta | OCH₃ (para to OCHF₂) |
| 369. | 2 | CH₃ | H | OCHF₂ | NH | meta | CH₃ (para to NH) |
| 370. | 2 | CH₃ | H | OCHF₂ | NH | ortho | Cl (para to NH) |
| 371. | 2 | CH₃ | H | OCHF₂ | NH | ortho | Cl (para to OCHF₂) |
| 372. | 2 | CH₃ | H | OCHF₂ | NH | ortho | F (para to NH) |
| 373. | 2 | CH₃ | H | OCHF₂ | NH | ortho | F (para to OCHF₂) |
| 374. | 2 | CH₃ | H | OCHF₂ | NH | meta | OCHF₂ (para to NH) |
| 375. | 2 | H | H | OCHF₂ | NCH₃ | ortho | H |
| 376. | 2 | H | H | OCHF₂ | NCH₃ | meta | H |
| 377. | 2 | H | H | OCHF₂ | NCH₃ | para | H |
| 378. | 2 | H | H | OCHF₂ | NCH₃ | ortho | CH₃ (para to X) |
| 379. | 2 | H | H | OCHF₂ | NCH₃ | ortho | CH₃ (para to OCHF₂) |
| 380. | 2 | H | H | OCHF₂ | NCH₃ | meta | OCH₃ (para to X) |
| 381. | 2 | H | H | OCHF₂ | NCH₃ | meta | OCH₃ (para to OCHF₂) |
| 382. | 2 | H | H | OCHF₂ | NCH₃ | meta | CH₃ (para to X) |
| 383. | 2 | H | H | OCHF₂ | NCH₃ | ortho | Cl (para to X) |
| 384. | 2 | H | H | OCHF₂ | NCH₃ | ortho | Cl (para to OCHF₂) |
| 385. | 2 | H | H | OCHF₂ | NCH₃ | ortho | F (para to X) |
| 386. | 2 | H | H | OCHF₂ | NCH₃ | ortho | F (para to OCHF₂) |
| 387. | 2 | H | H | OCHF₂ | NCH₃ | meta | OCHF₂ (para to X) |
| 388. | 2 | CH₃ | H | OCHF₂ | NCH₃ | ortho | H |
| 389. | 2 | CH₃ | H | OCHF₂ | NCH₃ | meta | H |
| 390. | 2 | CH₃ | H | OCHF₂ | NCH₃ | para | H |
| 391. | 2 | CH₃ | H | OCHF₂ | NCH₃ | ortho | CH₃ (para to X) |
| 392. | 2 | CH₃ | H | OCHF₂ | NCH₃ | ortho | CH₃ (para to OCHF₂) |
| 393. | 2 | CH₃ | H | OCHF₂ | NCH₃ | meta | OCH₃ (para to X) |
| 394. | 2 | CH₃ | H | OCHF₂ | NCH₃ | meta | OCH₃ (para to OCHF₂) |
| 395. | 2 | CH₃ | H | OCHF₂ | NCH₃ | meta | CH₃ (para to X) |
| 396. | 2 | CH₃ | H | OCHF₂ | NCH₃ | ortho | Cl (para to X) |
| 397. | 2 | CH₃ | H | OCHF₂ | NCH₃ | ortho | Cl (para to OCHF₂) |
| 398. | 2 | CH₃ | H | OCHF₂ | NCH₃ | ortho | F (para to X) |
| 399. | 2 | CH₃ | H | OCHF₂ | NCH₃ | ortho | F (para to OCHF₂) |
| 400. | 2 | CH₃ | H | OCHF₂ | NCH₃ | meta | OCHF₂ (para to X) |
| 401. | 2 | H | H | OCHF₂ | NCH₂CH₃ | ortho | H |
| 402. | 2 | H | H | OCHF₂ | NCH₂CH₃ | meta | H |
| 403. | 2 | H | H | OCHF₂ | NCH₂CH₃ | para | H |
| 404. | 2 | H | H | OCHF₂ | NCH₂CH₃ | ortho | CH₃ (para to X) |
| 405. | 2 | H | H | OCHF₂ | NCH₂CH₃ | ortho | CH₃ (para to OCHF₂) |
| 406. | 2 | H | H | OCHF₂ | NCH₂CH₃ | meta | OCH₃ (para to X) |
| 407. | 2 | H | H | OCHF₂ | NCH₂CH₃ | meta | OCH₃ (para to OCHF₂) |
| 408. | 2 | H | H | OCHF₂ | NCH₂CH₃ | meta | CH₃ (para to X) |
| 409. | 2 | CH₃ | H | OCHF₂ | NCH₂CH₃ | ortho | H |
| 410. | 2 | CH₃ | H | OCHF₂ | NCH₂CH₃ | meta | H |
| 411. | 2 | CH₃ | H | OCHF₂ | NCH₂CH₃ | para | H |
| 412. | 2 | CH₃ | H | OCHF₂ | NCH₂CH₃ | ortho | CH₃ (para to X) |
| 413. | 2 | CH₃ | H | OCHF₂ | NCH₂CH₃ | ortho | CH₃ (para to OCHF₂) |
| 414. | 2 | CH₃ | H | OCHF₂ | NCH₂CH₃ | meta | OCH₃ (para to X) |
| 415. | 2 | CH₃ | H | OCHF₂ | NCH₂CH₃ | meta | OCH₃ (para to OCHF₂) |
| 416. | 2 | CH₃ | H | OCHF₂ | NCH₂CH₃ | meta | CH₃ (para to X) |
| 417. | 2 | H | H | OCHF₂ | N(CH₂)₂CH₃ | ortho | H |
| 418. | 2 | H | H | OCHF₂ | N(CH₂)₂CH₃ | meta | H |
| 419. | 2 | H | H | OCHF₂ | N(CH₂)₂CH₃ | para | H |
| 420. | 2 | H | H | OCHF₂ | N(CH₂)₂CH₃ | ortho | CH₃ (para to X) |
| 421. | 2 | H | H | OCHF₂ | N(CH₂)₂CH₃ | ortho | CH₃ (para to OCHF₂) |
| 422. | 2 | H | H | OCHF₂ | N(CH₂)₂CH₃ | meta | OCH₃ (para to X) |
| 423. | 2 | H | H | OCHF₂ | N(CH₂)₂CH₃ | meta | OCH₃ (para to OCHF₂) |
| 424. | 2 | H | H | OCHF₂ | N(CH₂)₂CH₃ | meta | CH₃ (para to X) |
| 425. | 2 | CH₃ | H | OCHF₂ | N(CH₂)₂CH₃ | ortho | H |
| 426. | 2 | CH₃ | H | OCHF₂ | N(CH₂)₂CH₃ | meta | H |
| 427. | 2 | CH₃ | H | OCHF₂ | N(CH₂)₂CH₃ | para | H |
| 428. | 2 | CH₃ | H | OCHF₂ | N(CH₂)₂CH₃ | ortho | CH₃ (para to X) |
| 429. | 2 | CH₃ | H | OCHF₂ | N(CH₂)₂CH₃ | ortho | CH₃ (para to OCHF₂) |
| 430. | 2 | CH₃ | H | OCHF₂ | N(CH₂)₂CH₃ | meta | OCH₃ (para to X) |
| 431. | 2 | CH₃ | H | OCHF₂ | N(CH₂)₂CH₃ | meta | OCH₃ (para to OCHF₂) |
| 432. | 2 | CH₃ | H | OCHF₂ | N(CH₂)₂CH₃ | meta | CH₃ (para to X) |
| 433. | 2 | H | H | OCHF₂ | N(CH₂)-cyclopropyl | ortho | H |
| 434. | 2 | H | H | OCHF₂ | N(CH₂)-cyclopropyl | meta | H |
| 435. | 2 | H | H | OCHF₂ | N(CH₂)-cyclopropyl | para | H |
| 436. | 2 | H | H | OCHF₂ | N(CH₂)-cyclopropyl | ortho | CH₃ (para to X) |
| 437. | 2 | H | H | OCHF₂ | N(CH₂)-cyclopropyl | ortho | CH₃ (para to OCHF₂) |
| 438. | 2 | H | H | OCHF₂ | N(CH₂)-cyclopropyl | meta | OCH₃ (para to X) |

TABLE A-continued

| No. | n | R¹ | R² | R³ | X | OCHF$_2$* | R⁵ |
|---|---|---|---|---|---|---|---|
| 439. | 2 | H | H | OCHF$_2$ | N(CH$_2$)-cyclopropyl | meta | OCH$_3$ (para to OCHF$_2$) |
| 440. | 2 | H | H | OCHF$_2$ | N(CH$_2$)-cyclopropyl | meta | CH$_3$ (para to X) |
| 441. | 2 | CH$_3$ | H | OCHF$_2$ | N(CH$_2$)-cyclopropyl | ortho | H |
| 442. | 2 | CH$_3$ | H | OCHF$_2$ | N(CH$_2$)-cyclopropyl | meta | H |
| 443. | 2 | CH$_3$ | H | OCHF$_2$ | N(CH$_2$)-cyclopropyl | para | H |
| 444. | 2 | CH$_3$ | H | OCHF$_2$ | N(CH$_2$)-cyclopropyl | ortho | CH$_3$ (para to X) |
| 445. | 2 | CH$_3$ | H | OCHF$_2$ | N(CH$_2$)-cyclopropyl | ortho | CH$_3$ (para to OCHF$_2$) |
| 446. | 2 | CH$_3$ | H | OCHF$_2$ | N(CH$_2$)-cyclopropyl | meta | OCH$_3$ (para to X) |
| 447. | 2 | CH$_3$ | H | OCHF$_2$ | N(CH$_2$)-cyclopropyl | meta | OCH$_3$ (para to OCHF$_2$) |
| 448. | 2 | CH$_3$ | H | OCHF$_2$ | N(CH$_2$)-cyclopropyl | meta | CH$_3$ (para to X) |
| 449. | 2 | H | H | OCHF$_2$ | bond | ortho | H |
| 450. | 2 | H | H | OCHF$_2$ | bond | meta | H |
| 451. | 2 | H | H | OCHF$_2$ | bond | para | H |
| 452. | 2 | H | H | OCHF$_2$ | bond | ortho | CH$_3$ (para to X) |
| 453. | 2 | H | H | OCHF$_2$ | bond | ortho | CH$_3$ (para to OCHF$_2$) |
| 454. | 2 | H | H | OCHF$_2$ | bond | meta | OCH$_3$ (para to X) |
| 455. | 2 | H | H | OCHF$_2$ | bond | meta | OCH$_3$ (para to OCHF$_2$) |
| 456. | 2 | H | H | OCHF$_2$ | bond | meta | CH$_3$ (para to X) |
| 457. | 2 | CH$_3$ | H | OCHF$_2$ | bond | ortho | H |
| 458. | 2 | CH$_3$ | H | OCHF$_2$ | bond | meta | H |
| 459. | 2 | CH$_3$ | H | OCHF$_2$ | bond | para | H |
| 460. | 2 | CH$_3$ | H | OCHF$_2$ | bond | ortho | CH$_3$ (para to X) |
| 461. | 2 | CH$_3$ | H | OCHF$_2$ | bond | ortho | CH$_3$ (para to OCHF$_2$) |
| 462. | 2 | CH$_3$ | H | OCHF$_2$ | bond | meta | OCH$_3$ (para to X) |
| 463. | 2 | CH$_3$ | H | OCHF$_2$ | bond | meta | OCH$_3$ (para to OCHF$_2$) |
| 464. | 2 | CH$_3$ | H | OCHF$_2$ | bond | meta | CH$_3$ (para to X) |
| 465. | 1 | H | H | CH$_3$ | NH | ortho | H |
| 466. | 1 | H | H | CH$_3$ | NH | meta | H |
| 467. | 1 | H | H | CH$_3$ | NH | para | H |
| 468. | 1 | H | H | CH$_3$ | NH | ortho | CH$_3$ (para to NH) |
| 469. | 1 | H | H | CH$_3$ | NH | ortho | CH$_3$ (para to OCHF$_2$) |
| 470. | 1 | H | H | CH$_3$ | NH | meta | OCH$_3$ (para to NH) |
| 471. | 1 | H | H | CH$_3$ | NH | meta | OCH$_3$ (para to OCHF$_2$) |
| 472. | 1 | H | H | CH$_3$ | NH | meta | CH$_3$ (para to NH) |
| 473. | 1 | H | H | CH$_3$ | NH | ortho | Cl (para to NH) |
| 474. | 1 | H | H | CH$_3$ | NH | ortho | Cl (para to OCHF$_2$) |
| 475. | 1 | H | H | CH$_3$ | NH | ortho | F (para to NH) |
| 476. | 1 | H | H | CH$_3$ | NH | ortho | F (para to OCHF$_2$) |
| 477. | 1 | H | H | CH$_3$ | NH | meta | OCHF$_2$ (para to NH) |
| 478. | 1 | CH$_3$ | H | CH$_3$ | NH | ortho | H |
| 479. | 1 | CH$_3$ | H | CH$_3$ | NH | meta | H |
| 480. | 1 | CH$_3$ | H | CH$_3$ | NH | para | H |
| 481. | 1 | CH$_3$ | H | CH$_3$ | NH | ortho | CH$_3$ (para to NH) |
| 482. | 1 | CH$_3$ | H | CH$_3$ | NH | ortho | CH$_3$ (para to OCHF$_2$) |
| 483. | 1 | CH$_3$ | H | CH$_3$ | NH | meta | OCH$_3$ (para to NH) |
| 484. | 1 | CH$_3$ | H | CH$_3$ | NH | meta | OCH$_3$ (para to OCHF$_2$) |
| 485. | 1 | CH$_3$ | H | CH$_3$ | NH | meta | CH$_3$ (para to NH) |
| 486. | 1 | CH$_3$ | H | CH$_3$ | NH | ortho | Cl (para to NH) |
| 487. | 1 | CH$_3$ | H | CH$_3$ | NH | ortho | Cl (para to OCHF$_2$) |
| 488. | 1 | CH$_3$ | H | CH$_3$ | NH | ortho | F (para to NH) |
| 489. | 1 | CH$_3$ | H | CH$_3$ | NH | ortho | F (para to OCHF$_2$) |
| 490. | 1 | CH$_3$ | H | CH$_3$ | NH | meta | OCHF$_2$ (para to NH) |
| 491. | 1 | H | H | CH$_3$ | NCH$_3$ | ortho | H |
| 492. | 1 | H | H | CH$_3$ | NCH$_3$ | meta | H |
| 493. | 1 | H | H | CH$_3$ | NCH$_3$ | para | H |
| 494. | 1 | H | H | CH$_3$ | NCH$_3$ | ortho | CH$_3$ (para to X) |
| 495. | 1 | H | H | CH$_3$ | NCH$_3$ | ortho | CH$_3$ (para to OCHF$_2$) |
| 496. | 1 | H | H | CH$_3$ | NCH$_3$ | meta | OCH$_3$ (para to X) |
| 497. | 1 | H | H | CH$_3$ | NCH$_3$ | meta | OCH$_3$ (para to OCHF$_2$) |
| 498. | 1 | H | H | CH$_3$ | NCH$_3$ | meta | CH$_3$ (para to X) |
| 499. | 1 | H | H | CH$_3$ | NCH$_3$ | ortho | Cl (para to X) |
| 500. | 1 | H | H | CH$_3$ | NCH$_3$ | ortho | Cl (para to OCHF$_2$) |
| 501. | 1 | H | H | CH$_3$ | NCH$_3$ | ortho | F (para to X) |
| 502. | 1 | H | H | CH$_3$ | NCH$_3$ | ortho | F (para to OCHF$_2$) |
| 503. | 1 | H | H | CH$_3$ | NCH$_3$ | meta | OCHF$_2$ (para to X) |
| 504. | 1 | CH$_3$ | H | CH$_3$ | NCH$_3$ | ortho | H |
| 505. | 1 | CH$_3$ | H | CH$_3$ | NCH$_3$ | meta | H |
| 506. | 1 | CH$_3$ | H | CH$_3$ | NCH$_3$ | para | H |
| 507. | 1 | CH$_3$ | H | CH$_3$ | NCH$_3$ | ortho | CH$_3$ (para to X) |
| 508. | 1 | CH$_3$ | H | CH$_3$ | NCH$_3$ | ortho | CH$_3$ (para to OCHF$_2$) |
| 509. | 1 | CH$_3$ | H | CH$_3$ | NCH$_3$ | meta | OCH$_3$ (para to X) |
| 510. | 1 | CH$_3$ | H | CH$_3$ | NCH$_3$ | meta | OCH$_3$ (para to OCHF$_2$) |
| 511. | 1 | CH$_3$ | H | CH$_3$ | NCH$_3$ | meta | CH$_3$ (para to X) |
| 512. | 1 | CH$_3$ | H | CH$_3$ | NCH$_3$ | ortho | Cl (para to X) |
| 513. | 1 | CH$_3$ | H | CH$_3$ | NCH$_3$ | ortho | Cl (para to OCHF$_2$) |
| 514. | 1 | CH$_3$ | H | CH$_3$ | NCH$_3$ | ortho | F (para to X) |
| 515. | 1 | CH$_3$ | H | CH$_3$ | NCH$_3$ | ortho | F (para to OCHF$_2$) |
| 516. | 1 | CH$_3$ | H | CH$_3$ | NCH$_3$ | meta | OCHF$_2$ (para to X) |

TABLE A-continued

| No. | n | R¹ | R² | R³ | X | OCHF$_2$* | R⁵ |
|---|---|---|---|---|---|---|---|
| 517. | 1 | H | H | CH$_3$ | NCH$_2$CH$_3$ | ortho | H |
| 518. | 1 | H | H | CH$_3$ | NCH$_2$CH$_3$ | meta | H |
| 519. | 1 | H | H | CH$_3$ | NCH$_2$CH$_3$ | para | H |
| 520. | 1 | H | H | CH$_3$ | NCH$_2$CH$_3$ | ortho | CH$_3$ (para to X) |
| 521. | 1 | H | H | CH$_3$ | NCH$_2$CH$_3$ | ortho | CH$_3$ (para to OCHF$_2$) |
| 522. | 1 | H | H | CH$_3$ | NCH$_2$CH$_3$ | meta | OCH$_3$ (para to X) |
| 523. | 1 | H | H | CH$_3$ | NCH$_2$CH$_3$ | meta | OCH$_3$ (para to OCHF$_2$) |
| 524. | 1 | H | H | CH$_3$ | NCH$_2$CH$_3$ | meta | CH$_3$ (para to X) |
| 525. | 1 | CH$_3$ | H | CH$_3$ | NCH$_2$CH$_3$ | ortho | H |
| 526. | 1 | CH$_3$ | H | CH$_3$ | NCH$_2$CH$_3$ | meta | H |
| 527. | 1 | CH$_3$ | H | CH$_3$ | NCH$_2$CH$_3$ | para | H |
| 528. | 1 | CH$_3$ | H | CH$_3$ | NCH$_2$CH$_3$ | ortho | CH$_3$ (para to X) |
| 529. | 1 | CH$_3$ | H | CH$_3$ | NCH$_2$CH$_3$ | ortho | CH$_3$ (para to OCHF$_2$) |
| 530. | 1 | CH$_3$ | H | CH$_3$ | NCH$_2$CH$_3$ | meta | OCH$_3$ (para to X) |
| 531. | 1 | CH$_3$ | H | CH$_3$ | NCH$_2$CH$_3$ | meta | OCH$_3$ (para to OCHF$_2$) |
| 532. | 1 | CH$_3$ | H | CH$_3$ | NCH$_2$CH$_3$ | meta | CH$_3$ (para to X) |
| 533. | 1 | H | H | CH$_3$ | N(CH$_2$)$_2$CH$_3$ | ortho | H |
| 534. | 1 | H | H | CH$_3$ | N(CH$_2$)$_2$CH$_3$ | meta | H |
| 535. | 1 | H | H | CH$_3$ | N(CH$_2$)$_2$CH$_3$ | para | H |
| 536. | 1 | H | H | CH$_3$ | N(CH$_2$)$_2$CH$_3$ | ortho | CH$_3$ (para to X) |
| 537. | 1 | H | H | CH$_3$ | N(CH$_2$)$_2$CH$_3$ | ortho | CH$_3$ (para to OCHF$_2$) |
| 538. | 1 | H | H | CH$_3$ | N(CH$_2$)$_2$CH$_3$ | meta | OCH$_3$ (para to X) |
| 539. | 1 | H | H | CH$_3$ | N(CH$_2$)$_2$CH$_3$ | meta | OCH$_3$ (para to OCHF$_2$) |
| 540. | 1 | H | H | CH$_3$ | N(CH$_2$)$_2$CH$_3$ | meta | CH$_3$ (para to X) |
| 541. | 1 | CH$_3$ | H | CH$_3$ | N(CH$_2$)$_2$CH$_3$ | ortho | H |
| 542. | 1 | CH$_3$ | H | CH$_3$ | N(CH$_2$)$_2$CH$_3$ | meta | H |
| 543. | 1 | CH$_3$ | H | CH$_3$ | N(CH$_2$)$_2$CH$_3$ | para | H |
| 544. | 1 | CH$_3$ | H | CH$_3$ | N(CH$_2$)$_2$CH$_3$ | ortho | CH$_3$ (para to X) |
| 545. | 1 | CH$_3$ | H | CH$_3$ | N(CH$_2$)$_2$CH$_3$ | ortho | CH$_3$ (para to OCHF$_2$) |
| 546. | 1 | CH$_3$ | H | CH$_3$ | N(CH$_2$)$_2$CH$_3$ | meta | OCH$_3$ (para to X) |
| 547. | 1 | CH$_3$ | H | CH$_3$ | N(CH$_2$)$_2$CH$_3$ | meta | OCH$_3$ (para to OCHF$_2$) |
| 548. | 1 | CH$_3$ | H | CH$_3$ | N(CH$_2$)$_2$CH$_3$ | meta | CH$_3$ (para to X) |
| 549. | 1 | H | H | CH$_3$ | N(CH$_2$)-cyclopropyl | ortho | H |
| 550. | 1 | H | H | CH$_3$ | N(CH$_2$)-cyclopropyl | meta | H |
| 551. | 1 | H | H | CH$_3$ | N(CH$_2$)-cyclopropyl | para | H |
| 552. | 1 | H | H | CH$_3$ | N(CH$_2$)-cyclopropyl | ortho | CH$_3$ (para to X) |
| 553. | 1 | H | H | CH$_3$ | N(CH$_2$)-cyclopropyl | ortho | CH$_3$ (para to OCHF$_2$) |
| 554. | 1 | H | H | CH$_3$ | N(CH$_2$)-cyclopropyl | meta | OCH$_3$ (para to X) |
| 555. | 1 | H | H | CH$_3$ | N(CH$_2$)-cyclopropyl | meta | OCH$_3$ (para to OCHF$_2$) |
| 556. | 1 | H | H | CH$_3$ | N(CH$_2$)-cyclopropyl | meta | CH$_3$ (para to X) |
| 557. | 1 | CH$_3$ | H | CH$_3$ | N(CH$_2$)-cyclopropyl | ortho | H |
| 558. | 1 | CH$_3$ | H | CH$_3$ | N(CH$_2$)-cyclopropyl | meta | H |
| 559. | 1 | CH$_3$ | H | CH$_3$ | N(CH$_2$)-cyclopropyl | para | H |
| 560. | 1 | CH$_3$ | H | CH$_3$ | N(CH$_2$)-cyclopropyl | ortho | CH$_3$ (para to X) |
| 561. | 1 | CH$_3$ | H | CH$_3$ | N(CH$_2$)-cyclopropyl | ortho | CH$_3$ (para to OCHF$_2$) |
| 562. | 1 | CH$_3$ | H | CH$_3$ | N(CH$_2$)-cyclopropyl | meta | OCH$_3$ (para to X) |
| 563. | 1 | CH$_3$ | H | CH$_3$ | N(CH$_2$)-cyclopropyl | meta | OCH$_3$ (para to OCHF$_2$) |
| 564. | 1 | CH$_3$ | H | CH$_3$ | N(CH$_2$)-cyclopropyl | meta | CH$_3$ (para to X) |
| 565. | 1 | H | H | CH$_3$ | bond | ortho | H |
| 566. | 1 | H | H | CH$_3$ | bond | meta | H |
| 567. | 1 | H | H | CH$_3$ | bond | para | H |
| 568. | 1 | H | H | CH$_3$ | bond | ortho | CH$_3$ (para to X) |
| 569. | 1 | H | H | CH$_3$ | bond | ortho | CH$_3$ (para to OCHF$_2$) |
| 570. | 1 | H | H | CH$_3$ | bond | meta | OCH$_3$ (para to X) |
| 571. | 1 | H | H | CH$_3$ | bond | meta | OCH$_3$ (para to OCHF$_2$) |
| 572. | 1 | H | H | CH$_3$ | bond | meta | CH$_3$ (para to X) |
| 573. | 1 | CH$_3$ | H | CH$_3$ | bond | ortho | H |
| 574. | 1 | CH$_3$ | H | CH$_3$ | bond | meta | H |
| 575. | 1 | CH$_3$ | H | CH$_3$ | bond | para | H |
| 576. | 1 | CH$_3$ | H | CH$_3$ | bond | ortho | CH$_3$ (para to X) |
| 577. | 1 | CH$_3$ | H | CH$_3$ | bond | ortho | CH$_3$ (para to OCHF$_2$) |
| 578. | 1 | CH$_3$ | H | CH$_3$ | bond | meta | OCH$_3$ (para to X) |
| 579. | 1 | CH$_3$ | H | CH$_3$ | bond | meta | OCH$_3$ (para to OCHF$_2$) |
| 580. | 1 | CH$_3$ | H | CH$_3$ | bond | meta | CH$_3$ (para to X) |
| 581. | 2 | H | H | CH$_3$ | NH | ortho | H |
| 582. | 2 | H | H | CH$_3$ | NH | meta | H |
| 583. | 2 | H | H | CH$_3$ | NH | para | H |
| 584. | 2 | H | H | CH$_3$ | NH | ortho | CH$_3$ (para to NH) |
| 585. | 2 | H | H | CH$_3$ | NH | ortho | CH$_3$ (para to OCHF$_2$) |
| 586. | 2 | H | H | CH$_3$ | NH | meta | OCH$_3$ (para to NH) |
| 587. | 2 | H | H | CH$_3$ | NH | meta | OCH$_3$ (para to OCHF$_2$) |
| 588. | 2 | H | H | CH$_3$ | NH | meta | CH$_3$ (para to NH) |
| 589. | 2 | H | H | CH$_3$ | NH | ortho | Cl (para to NH) |
| 590. | 2 | H | H | CH$_3$ | NH | ortho | Cl (para to OCHF$_2$) |
| 591. | 2 | H | H | CH$_3$ | NH | ortho | F (para to NH) |
| 592. | 2 | H | H | CH$_3$ | NH | ortho | F (para to OCHF$_2$) |
| 593. | 2 | H | H | CH$_3$ | NH | meta | OCHF$_2$ (para to NH) |
| 594. | 2 | CH$_3$ | H | CH$_3$ | NH | ortho | H |

TABLE A-continued

| No. | n | R¹ | R² | R³ | X | OCHF$_2$* | R⁵ |
|---|---|---|---|---|---|---|---|
| 595. | 2 | CH$_3$ | H | CH$_3$ | NH | meta | H |
| 596. | 2 | CH$_3$ | H | CH$_3$ | NH | para | H |
| 597. | 2 | CH$_3$ | H | CH$_3$ | NH | ortho | CH$_3$ (para to NH) |
| 598. | 2 | CH$_3$ | H | CH$_3$ | NH | ortho | CH$_3$ (para to OCHF$_2$) |
| 599. | 2 | CH$_3$ | H | CH$_3$ | NH | meta | OCH$_3$ (para to NH) |
| 600. | 2 | CH$_3$ | H | CH$_3$ | NH | meta | OCH$_3$ (para to OCHF$_2$) |
| 601. | 2 | CH$_3$ | H | CH$_3$ | NH | meta | CH$_3$ (para to NH) |
| 602. | 2 | CH$_3$ | H | CH$_3$ | NH | ortho | Cl (para to NH) |
| 603. | 2 | CH$_3$ | H | CH$_3$ | NH | ortho | Cl (para to OCHF$_2$) |
| 604. | 2 | CH$_3$ | H | CH$_3$ | NH | ortho | F (para to NH) |
| 605. | 2 | CH$_3$ | H | CH$_3$ | NH | ortho | F (para to OCHF$_2$) |
| 606. | 2 | CH$_3$ | H | CH$_3$ | NH | meta | OCHF$_2$ (para to NH) |
| 607. | 2 | H | H | CH$_3$ | NCH$_3$ | ortho | H |
| 608. | 2 | H | H | CH$_3$ | NCH$_3$ | meta | H |
| 609. | 2 | H | H | CH$_3$ | NCH$_3$ | para | H |
| 610. | 2 | H | H | CH$_3$ | NCH$_3$ | ortho | CH$_3$ (para to X) |
| 611. | 2 | H | H | CH$_3$ | NCH$_3$ | ortho | CH$_3$ (para to OCHF$_2$) |
| 612. | 2 | H | H | CH$_3$ | NCH$_3$ | meta | OCH$_3$ (para to X) |
| 613. | 2 | H | H | CH$_3$ | NCH$_3$ | meta | OCH$_3$ (para to OCHF$_2$) |
| 614. | 2 | H | H | CH$_3$ | NCH$_3$ | meta | CH$_3$ (para to X) |
| 615. | 2 | H | H | CH$_3$ | NCH$_3$ | ortho | Cl (para to X) |
| 616. | 2 | H | H | CH$_3$ | NCH$_3$ | ortho | Cl (para to OCHF$_2$) |
| 617. | 2 | H | H | CH$_3$ | NCH$_3$ | ortho | F (para to X) |
| 618. | 2 | H | H | CH$_3$ | NCH$_3$ | ortho | F (para to OCHF$_2$) |
| 619. | 2 | H | H | CH$_3$ | NCH$_3$ | meta | OCHF$_2$ (para to X) |
| 620. | 2 | CH$_3$ | H | CH$_3$ | NCH$_3$ | ortho | H |
| 621. | 2 | CH$_3$ | H | CH$_3$ | NCH$_3$ | meta | H |
| 622. | 2 | CH$_3$ | H | CH$_3$ | NCH$_3$ | para | H |
| 623. | 2 | CH$_3$ | H | CH$_3$ | NCH$_3$ | ortho | CH$_3$ (para to X) |
| 624. | 2 | CH$_3$ | H | CH$_3$ | NCH$_3$ | ortho | CH$_3$ (para to OCHF$_2$) |
| 625. | 2 | CH$_3$ | H | CH$_3$ | NCH$_3$ | meta | OCH$_3$ (para to X) |
| 626. | 2 | CH$_3$ | H | CH$_3$ | NCH$_3$ | meta | OCH$_3$ (para to OCHF$_2$) |
| 627. | 2 | CH$_3$ | H | CH$_3$ | NCH$_3$ | meta | CH$_3$ (para to X) |
| 628. | 2 | CH$_3$ | H | CH$_3$ | NCH$_3$ | ortho | Cl (para to X) |
| 629. | 2 | CH$_3$ | H | CH$_3$ | NCH$_3$ | ortho | Cl (para to OCHF$_2$) |
| 630. | 2 | CH$_3$ | H | CH$_3$ | NCH$_3$ | ortho | F (para to X) |
| 631. | 2 | CH$_3$ | H | CH$_3$ | NCH$_3$ | ortho | F (para to OCHF$_2$) |
| 632. | 2 | CH$_3$ | H | CH$_3$ | NCH$_3$ | meta | OCHF$_2$ (para to X) |
| 633. | 2 | H | H | CH$_3$ | NCH$_2$CH$_3$ | ortho | H |
| 634. | 2 | H | H | CH$_3$ | NCH$_2$CH$_3$ | meta | H |
| 635. | 2 | H | H | CH$_3$ | NCH$_2$CH$_3$ | para | H |
| 636. | 2 | H | H | CH$_3$ | NCH$_2$CH$_3$ | ortho | CH$_3$ (para to X) |
| 637. | 2 | H | H | CH$_3$ | NCH$_2$CH$_3$ | ortho | CH$_3$ (para to OCHF$_2$) |
| 638. | 2 | H | H | CH$_3$ | NCH$_2$CH$_3$ | meta | OCH$_3$ (para to X) |
| 639. | 2 | H | H | CH$_3$ | NCH$_2$CH$_3$ | meta | OCH$_3$ (para to OCHF$_2$) |
| 640. | 2 | H | H | CH$_3$ | NCH$_2$CH$_3$ | meta | CH$_3$ (para to X) |
| 641. | 2 | CH$_3$ | H | CH$_3$ | NCH$_2$CH$_3$ | ortho | H |
| 642. | 2 | CH$_3$ | H | CH$_3$ | NCH$_2$CH$_3$ | meta | H |
| 643. | 2 | CH$_3$ | H | CH$_3$ | NCH$_2$CH$_3$ | para | H |
| 644. | 2 | CH$_3$ | H | CH$_3$ | NCH$_2$CH$_3$ | ortho | CH$_3$ (para to X) |
| 645. | 2 | CH$_3$ | H | CH$_3$ | NCH$_2$CH$_3$ | ortho | CH$_3$ (para to OCHF$_2$) |
| 646. | 2 | CH$_3$ | H | CH$_3$ | NCH$_2$CH$_3$ | meta | OCH$_3$ (para to X) |
| 647. | 2 | CH$_3$ | H | CH$_3$ | NCH$_2$CH$_3$ | meta | OCH$_3$ (para to OCHF$_2$) |
| 648. | 2 | CH$_3$ | H | CH$_3$ | NCH$_2$CH$_3$ | meta | CH$_3$ (para to X) |
| 649. | 2 | H | H | CH$_3$ | N(CH$_2$)$_2$CH$_3$ | ortho | H |
| 650. | 2 | H | H | CH$_3$ | N(CH$_2$)$_2$CH$_3$ | meta | H |
| 651. | 2 | H | H | CH$_3$ | N(CH$_2$)$_2$CH$_3$ | para | H |
| 652. | 2 | H | H | CH$_3$ | N(CH$_2$)$_2$CH$_3$ | ortho | CH$_3$ (para to X) |
| 653. | 2 | H | H | CH$_3$ | N(CH$_2$)$_2$CH$_3$ | ortho | CH$_3$ (para to OCHF$_2$) |
| 654. | 2 | H | H | CH$_3$ | N(CH$_2$)$_2$CH$_3$ | meta | OCH$_3$ (para to X) |
| 655. | 2 | H | H | CH$_3$ | N(CH$_2$)$_2$CH$_3$ | meta | OCH$_3$ (para to OCHF$_2$) |
| 656. | 2 | H | H | CH$_3$ | N(CH$_2$)$_2$CH$_3$ | meta | CH$_3$ (para to X) |
| 657. | 2 | CH$_3$ | H | CH$_3$ | N(CH$_2$)$_2$CH$_3$ | ortho | H |
| 658. | 2 | CH$_3$ | H | CH$_3$ | N(CH$_2$)$_2$CH$_3$ | meta | H |
| 659. | 2 | CH$_3$ | H | CH$_3$ | N(CH$_2$)$_2$CH$_3$ | para | H |
| 660. | 2 | CH$_3$ | H | CH$_3$ | N(CH$_2$)$_2$CH$_3$ | ortho | CH$_3$ (para to X) |
| 661. | 2 | CH$_3$ | H | CH$_3$ | N(CH$_2$)$_2$CH$_3$ | ortho | CH$_3$ (para to OCHF$_2$) |
| 662. | 2 | CH$_3$ | H | CH$_3$ | N(CH$_2$)$_2$CH$_3$ | meta | OCH$_3$ (para to X) |
| 663. | 2 | CH$_3$ | H | CH$_3$ | N(CH$_2$)$_2$CH$_3$ | meta | OCH$_3$ (para to OCHF$_2$) |
| 664. | 2 | CH$_3$ | H | CH$_3$ | N(CH$_2$)$_2$CH$_3$ | meta | CH$_3$ (para to X) |
| 665. | 2 | H | H | CH$_3$ | N(CH$_2$)-cyclopropyl | ortho | H |
| 666. | 2 | H | H | CH$_3$ | N(CH$_2$)-cyclopropyl | meta | H |
| 667. | 2 | H | H | CH$_3$ | N(CH$_2$)-cyclopropyl | para | H |
| 668. | 2 | H | H | CH$_3$ | N(CH$_2$)-cyclopropyl | ortho | CH$_3$ (para to X) |
| 669. | 2 | H | H | CH$_3$ | N(CH$_2$)-cyclopropyl | ortho | CH$_3$ (para to OCHF$_2$) |
| 670. | 2 | H | H | CH$_3$ | N(CH$_2$)-cyclopropyl | meta | OCH$_3$ (para to X) |
| 671. | 2 | H | H | CH$_3$ | N(CH$_2$)-cyclopropyl | meta | OCH$_3$ (para to OCHF$_2$) |
| 672. | 2 | H | H | CH$_3$ | N(CH$_2$)-cyclopropyl | meta | CH$_3$ (para to X) |

TABLE A-continued

| No. | n | R$^1$ | R$^2$ | R$^3$ | X | OCHF$_2$* | R$^5$ |
|---|---|---|---|---|---|---|---|
| 673. | 2 | CH$_3$ | H | CH$_3$ | N(CH$_2$)-cyclopropyl | ortho | H |
| 674. | 2 | CH$_3$ | H | CH$_3$ | N(CH$_2$)-cyclopropyl | meta | H |
| 675. | 2 | CH$_3$ | H | CH$_3$ | N(CH$_2$)-cyclopropyl | para | H |
| 676. | 2 | CH$_3$ | H | CH$_3$ | N(CH$_2$)-cyclopropyl | ortho | CH$_3$ (para to X) |
| 677. | 2 | CH$_3$ | H | CH$_3$ | N(CH$_2$)-cyclopropyl | ortho | CH$_3$ (para to OCHF$_2$) |
| 678. | 2 | CH$_3$ | H | CH$_3$ | N(CH$_2$)-cyclopropyl | meta | OCH$_3$ (para to X) |
| 679. | 2 | CH$_3$ | H | CH$_3$ | N(CH$_2$)-cyclopropyl | meta | OCH$_3$ (para to OCHF$_2$) |
| 680. | 2 | CH$_3$ | H | CH$_3$ | N(CH$_2$)-cyclopropyl | meta | CH$_3$ (para to X) |
| 681. | 2 | H | H | CH$_3$ | bond | ortho | H |
| 682. | 2 | H | H | CH$_3$ | bond | meta | H |
| 683. | 2 | H | H | CH$_3$ | bond | para | H |
| 684. | 2 | H | H | CH$_3$ | bond | ortho | CH$_3$ (para to X) |
| 685. | 2 | H | H | CH$_3$ | bond | ortho | CH$_3$ (para to OCHF$_2$) |
| 686. | 2 | H | H | CH$_3$ | bond | meta | OCH$_3$ (para to X) |
| 687. | 2 | H | H | CH$_3$ | bond | meta | OCH$_3$ (para to OCHF$_2$) |
| 688. | 2 | H | H | CH$_3$ | bond | meta | CH$_3$ (para to X) |
| 689. | 2 | CH$_3$ | H | CH$_3$ | bond | ortho | H |
| 690. | 2 | CH$_3$ | H | CH$_3$ | bond | meta | H |
| 691. | 2 | CH$_3$ | H | CH$_3$ | bond | para | H |
| 692. | 2 | CH$_3$ | H | CH$_3$ | bond | ortho | CH$_3$ (para to X) |
| 693. | 2 | CH$_3$ | H | CH$_3$ | bond | ortho | CH$_3$ (para to OCHF$_2$) |
| 694. | 2 | CH$_3$ | H | CH$_3$ | bond | meta | OCH$_3$ (para to X) |
| 695. | 2 | CH$_3$ | H | CH$_3$ | bond | meta | OCH$_3$ (para to OCHF$_2$) |
| 696. | 2 | CH$_3$ | H | CH$_3$ | bond | meta | CH$_3$ (para to X) |
| 697. | 1 | H | H | F | NH | ortho | H |
| 698. | 1 | H | H | F | NH | meta | H |
| 699. | 1 | H | H | F | NH | para | H |
| 700. | 1 | H | H | F | NH | ortho | CH$_3$ (para to NH) |
| 701. | 1 | H | H | F | NH | ortho | CH$_3$ (para to OCHF$_2$) |
| 702. | 1 | H | H | F | NH | meta | OCH$_3$ (para to NH) |
| 703. | 1 | H | H | F | NH | meta | OCH$_3$ (para to OCHF$_2$) |
| 704. | 1 | H | H | F | NH | meta | CH$_3$ (para to NH) |
| 705. | 1 | H | H | F | NH | ortho | Cl (para to NH) |
| 706. | 1 | H | H | F | NH | ortho | Cl (para to OCHF$_2$) |
| 707. | 1 | H | H | F | NH | ortho | F (para to NH) |
| 708. | 1 | H | H | F | NH | ortho | F (para to OCHF$_2$) |
| 709. | 1 | H | H | F | NH | meta | OCHF$_2$ (para to NH) |
| 710. | 1 | CH$_3$ | H | F | NH | ortho | H |
| 711. | 1 | CH$_3$ | H | F | NH | meta | H |
| 712. | 1 | CH$_3$ | H | F | NH | para | H |
| 713. | 1 | CH$_3$ | H | F | NH | ortho | CH$_3$ (para to NH) |
| 714. | 1 | CH$_3$ | H | F | NH | ortho | CH$_3$ (para to OCHF$_2$) |
| 715. | 1 | CH$_3$ | H | F | NH | meta | OCH$_3$ (para to NH) |
| 716. | 1 | CH$_3$ | H | F | NH | meta | OCH$_3$ (para to OCHF$_2$) |
| 717. | 1 | CH$_3$ | H | F | NH | meta | CH$_3$ (para to NH) |
| 718. | 1 | CH$_3$ | H | F | NH | ortho | Cl (para to NH) |
| 719. | 1 | CH$_3$ | H | F | NH | ortho | Cl (para to OCHF$_2$) |
| 720. | 1 | CH$_3$ | H | F | NH | ortho | F (para to NH) |
| 721. | 1 | CH$_3$ | H | F | NH | ortho | F (para to OCHF$_2$) |
| 722. | 1 | CH$_3$ | H | F | NH | meta | OCHF$_2$ (para to NH) |
| 723. | 1 | H | H | F | NCH$_3$ | ortho | H |
| 724. | 1 | H | H | F | NCH$_3$ | meta | H |
| 725. | 1 | H | H | F | NCH$_3$ | para | H |
| 726. | 1 | H | H | F | NCH$_3$ | ortho | CH$_3$ (para to X) |
| 727. | 1 | H | H | F | NCH$_3$ | ortho | CH$_3$ (para to OCHF$_2$) |
| 728. | 1 | H | H | F | NCH$_3$ | meta | OCH$_3$ (para to X) |
| 729. | 1 | H | H | F | NCH$_3$ | meta | OCH$_3$ (para to OCHF$_2$) |
| 730. | 1 | H | H | F | NCH$_3$ | meta | CH$_3$ (para to X) |
| 731. | 1 | H | H | F | NCH$_3$ | ortho | Cl (para to X) |
| 732. | 1 | H | H | F | NCH$_3$ | ortho | Cl (para to OCHF$_2$) |
| 733. | 1 | H | H | F | NCH$_3$ | ortho | F (para to X) |
| 734. | 1 | H | H | F | NCH$_3$ | ortho | F (para to OCHF$_2$) |
| 735. | 1 | H | H | F | NCH$_3$ | meta | OCHF$_2$ (para to X) |
| 736. | 1 | CH$_3$ | H | F | NCH$_3$ | ortho | H |
| 737. | 1 | CH$_3$ | H | F | NCH$_3$ | meta | H |
| 738. | 1 | CH$_3$ | H | F | NCH$_3$ | para | H |
| 739. | 1 | CH$_3$ | H | F | NCH$_3$ | ortho | CH$_3$ (para to X) |
| 740. | 1 | CH$_3$ | H | F | NCH$_3$ | ortho | CH$_3$ (para to OCHF$_2$) |
| 741. | 1 | CH$_3$ | H | F | NCH$_3$ | meta | OCH$_3$ (para to X) |
| 742. | 1 | CH$_3$ | H | F | NCH$_3$ | meta | OCH$_3$ (para to OCHF$_2$) |
| 743. | 1 | CH$_3$ | H | F | NCH$_3$ | meta | CH$_3$ (para to X) |
| 744. | 1 | CH$_3$ | H | F | NCH$_3$ | ortho | Cl (para to X) |
| 745. | 1 | CH$_3$ | H | F | NCH$_3$ | ortho | Cl (para to OCHF$_2$) |
| 746. | 1 | CH$_3$ | H | F | NCH$_3$ | ortho | F (para to X) |
| 747. | 1 | CH$_3$ | H | F | NCH$_3$ | ortho | F (para to OCHF$_2$) |
| 748. | 1 | CH$_3$ | H | F | NCH$_3$ | meta | OCHF$_2$ (para to X) |
| 749. | 1 | H | H | F | NCH$_2$CH$_3$ | ortho | H |
| 750. | 1 | H | H | F | NCH$_2$CH$_3$ | meta | H |

TABLE A-continued

| No. | n | R¹ | R² | R³ | X | OCHF$_2$* | R⁵ |
|---|---|---|---|---|---|---|---|
| 751. | 1 | H | H | F | NCH$_2$CH$_3$ | para | H |
| 752. | 1 | H | H | F | NCH$_2$CH$_3$ | ortho | CH$_3$ (para to X) |
| 753. | 1 | H | H | F | NCH$_2$CH$_3$ | ortho | CH$_3$ (para to OCHF$_2$) |
| 754. | 1 | H | H | F | NCH$_2$CH$_3$ | meta | OCH$_3$ (para to X) |
| 755. | 1 | H | H | F | NCH$_2$CH$_3$ | meta | OCH$_3$ (para to OCHF$_2$) |
| 756. | 1 | H | H | F | NCH$_2$CH$_3$ | meta | CH$_3$ (para to X) |
| 757. | 1 | CH$_3$ | H | F | NCH$_2$CH$_3$ | ortho | H |
| 758. | 1 | CH$_3$ | H | F | NCH$_2$CH$_3$ | meta | H |
| 759. | 1 | CH$_3$ | H | F | NCH$_2$CH$_3$ | para | H |
| 760. | 1 | CH$_3$ | H | F | NCH$_2$CH$_3$ | ortho | CH$_3$ (para to X) |
| 761. | 1 | CH$_3$ | H | F | NCH$_2$CH$_3$ | ortho | CH$_3$ (para to OCHF$_2$) |
| 762. | 1 | CH$_3$ | H | F | NCH$_2$CH$_3$ | meta | OCH$_3$ (para to X) |
| 763. | 1 | CH$_3$ | H | F | NCH$_2$CH$_3$ | meta | OCH$_3$ (para to OCHF$_2$) |
| 764. | 1 | CH$_3$ | H | F | NCH$_2$CH$_3$ | meta | CH$_3$ (para to X) |
| 765. | 1 | H | H | F | N(CH$_2$)$_2$CH$_3$ | ortho | H |
| 766. | 1 | H | H | F | N(CH$_2$)$_2$CH$_3$ | meta | H |
| 767. | 1 | H | H | F | N(CH$_2$)$_2$CH$_3$ | para | H |
| 768. | 1 | H | H | F | N(CH$_2$)$_2$CH$_3$ | ortho | CH$_3$ (para to X) |
| 769. | 1 | H | H | F | N(CH$_2$)$_2$CH$_3$ | ortho | CH$_3$ (para to OCHF$_2$) |
| 770. | 1 | H | H | F | N(CH$_2$)$_2$CH$_3$ | meta | OCH$_3$ (para to X) |
| 771. | 1 | H | H | F | N(CH$_2$)$_2$CH$_3$ | meta | OCH$_3$ (para to OCHF$_2$) |
| 772. | 1 | H | H | F | N(CH$_2$)$_2$CH$_3$ | meta | CH$_3$ (para to X) |
| 773. | 1 | CH$_3$ | H | F | N(CH$_2$)$_2$CH$_3$ | ortho | H |
| 774. | 1 | CH$_3$ | H | F | N(CH$_2$)$_2$CH$_3$ | meta | H |
| 775. | 1 | CH$_3$ | H | F | N(CH$_2$)$_2$CH$_3$ | para | H |
| 776. | 1 | CH$_3$ | H | F | N(CH$_2$)$_2$CH$_3$ | ortho | CH$_3$ (para to X) |
| 777. | 1 | CH$_3$ | H | F | N(CH$_2$)$_2$CH$_3$ | ortho | CH$_3$ (para to OCHF$_2$) |
| 778. | 1 | CH$_3$ | H | F | N(CH$_2$)$_2$CH$_3$ | meta | OCH$_3$ (para to X) |
| 779. | 1 | CH$_3$ | H | F | N(CH$_2$)$_2$CH$_3$ | meta | OCH$_3$ (para to OCHF$_2$) |
| 780. | 1 | CH$_3$ | H | F | N(CH$_2$)$_2$CH$_3$ | meta | CH$_3$ (para to X) |
| 781. | 1 | H | H | F | N(CH$_2$)-cyclopropyl | ortho | H |
| 782. | 1 | H | H | F | N(CH$_2$)-cyclopropyl | meta | H |
| 783. | 1 | H | H | F | N(CH$_2$)-cyclopropyl | para | H |
| 784. | 1 | H | H | F | N(CH$_2$)-cyclopropyl | ortho | CH$_3$ (para to X) |
| 785. | 1 | H | H | F | N(CH$_2$)-cyclopropyl | ortho | CH$_3$ (para to OCHF$_2$) |
| 786. | 1 | H | H | F | N(CH$_2$)-cyclopropyl | meta | OCH$_3$ (para to X) |
| 787. | 1 | H | H | F | N(CH$_2$)-cyclopropyl | meta | OCH$_3$ (para to OCHF$_2$) |
| 788. | 1 | H | H | F | N(CH$_2$)-cyclopropyl | meta | CH$_3$ (para to X) |
| 789. | 1 | CH$_3$ | H | F | N(CH$_2$)-cyclopropyl | ortho | H |
| 790. | 1 | CH$_3$ | H | F | N(CH$_2$)-cyclopropyl | meta | H |
| 791. | 1 | CH$_3$ | H | F | N(CH$_2$)-cyclopropyl | para | H |
| 792. | 1 | CH$_3$ | H | F | N(CH$_2$)-cyclopropyl | ortho | CH$_3$ (para to X) |
| 793. | 1 | CH$_3$ | H | F | N(CH$_2$)-cyclopropyl | ortho | CH$_3$ (para to OCHF$_2$) |
| 794. | 1 | CH$_3$ | H | F | N(CH$_2$)-cyclopropyl | meta | OCH$_3$ (para to X) |
| 795. | 1 | CH$_3$ | H | F | N(CH$_2$)-cyclopropyl | meta | OCH$_3$ (para to OCHF$_2$) |
| 796. | 1 | CH$_3$ | H | F | N(CH$_2$)-cyclopropyl | meta | CH$_3$ (para to X) |
| 797. | 1 | H | H | F | bond | ortho | H |
| 798. | 1 | H | H | F | bond | meta | H |
| 799. | 1 | H | H | F | bond | para | H |
| 800. | 1 | H | H | F | bond | ortho | CH$_3$ (para to X) |
| 801. | 1 | H | H | F | bond | ortho | CH$_3$ (para to OCHF$_2$) |
| 802. | 1 | H | H | F | bond | meta | OCH$_3$ (para to X) |
| 803. | 1 | H | H | F | bond | meta | OCH$_3$ (para to OCHF$_2$) |
| 804. | 1 | H | H | F | bond | meta | CH$_3$ (para to X) |
| 805. | 1 | CH$_3$ | H | F | bond | ortho | H |
| 806. | 1 | CH$_3$ | H | F | bond | meta | H |
| 807. | 1 | CH$_3$ | H | F | bond | para | H |
| 808. | 1 | CH$_3$ | H | F | bond | ortho | CH$_3$ (para to X) |
| 809. | 1 | CH$_3$ | H | F | bond | ortho | CH$_3$ (para to OCHF$_2$) |
| 810. | 1 | CH$_3$ | H | F | bond | meta | OCH$_3$ (para to X) |
| 811. | 1 | CH$_3$ | H | F | bond | meta | OCH$_3$ (para to OCHF$_2$) |
| 812. | 1 | CH$_3$ | H | F | bond | meta | CH$_3$ (para to X) |
| 813. | 2 | H | H | F | NH | ortho | H |
| 814. | 2 | H | H | F | NH | meta | H |
| 815. | 2 | H | H | F | NH | para | H |
| 816. | 2 | H | H | F | NH | ortho | CH$_3$ (para to NH) |
| 817. | 2 | H | H | F | NH | ortho | CH$_3$ (para to OCHF$_2$) |
| 818. | 2 | H | H | F | NH | meta | OCH$_3$ (para to NH) |
| 819. | 2 | H | H | F | NH | meta | OCH$_3$ (para to OCHF$_2$) |
| 820. | 2 | H | H | F | NH | meta | CH$_3$ (para to NH) |
| 821. | 2 | H | H | F | NH | ortho | Cl (para to NH) |
| 822. | 2 | H | H | F | NH | ortho | Cl (para to OCHF$_2$) |
| 823. | 2 | H | H | F | NH | ortho | F (para to NH) |
| 824. | 2 | H | H | F | NH | ortho | F (para to OCHF$_2$) |
| 825. | 2 | H | H | F | NH | meta | OCHF$_2$ (para to NH) |
| 826. | 2 | CH$_3$ | H | F | NH | ortho | H |
| 827. | 2 | CH$_3$ | H | F | NH | meta | H |
| 828. | 2 | CH$_3$ | H | F | NH | para | H |

TABLE A-continued

| No. | n | R¹ | R² | R³ | X | OCHF₂* | R⁵ |
|---|---|---|---|---|---|---|---|
| 829. | 2 | CH₃ | H | F | NH | ortho | CH₃ (para to NH) |
| 830. | 2 | CH₃ | H | F | NH | ortho | CH₃ (para to OCHF₂) |
| 831. | 2 | CH₃ | H | F | NH | meta | OCH₃ (para to NH) |
| 832. | 2 | CH₃ | H | F | NH | meta | OCH₃ (para to OCHF₂) |
| 833. | 2 | CH₃ | H | F | NH | meta | CH₃ (para to NH) |
| 834. | 2 | CH₃ | H | F | NH | ortho | Cl (para to NH) |
| 835. | 2 | CH₃ | H | F | NH | ortho | Cl (para to OCHF₂) |
| 836. | 2 | CH₃ | H | F | NH | ortho | F (para to NH) |
| 837. | 2 | CH₃ | H | F | NH | ortho | F (para to OCHF₂) |
| 838. | 2 | CH₃ | H | F | NH | meta | OCHF₂ (para to NH) |
| 839. | 2 | H | H | F | NCH₃ | ortho | H |
| 840. | 2 | H | H | F | NCH₃ | meta | H |
| 841. | 2 | H | H | F | NCH₃ | para | H |
| 842. | 2 | H | H | F | NCH₃ | ortho | CH₃ (para to X) |
| 843. | 2 | H | H | F | NCH₃ | ortho | CH₃ (para to OCHF₂) |
| 844. | 2 | H | H | F | NCH₃ | meta | OCH₃ (para to X) |
| 845. | 2 | H | H | F | NCH₃ | meta | OCH₃ (para to OCHF₂) |
| 846. | 2 | H | H | F | NCH₃ | meta | CH₃ (para to X) |
| 847. | 2 | H | H | F | NCH₃ | ortho | Cl (para to X) |
| 848. | 2 | H | H | F | NCH₃ | ortho | Cl (para to OCHF₂) |
| 849. | 2 | H | H | F | NCH₃ | ortho | F (para to X) |
| 850. | 2 | H | H | F | NCH₃ | ortho | F (para to OCHF₂) |
| 851. | 2 | H | H | F | NCH₃ | meta | OCHF₂ (para to X) |
| 852. | 2 | CH₃ | H | F | NCH₃ | ortho | H |
| 853. | 2 | CH₃ | H | F | NCH₃ | meta | H |
| 854. | 2 | CH₃ | H | F | NCH₃ | para | H |
| 855. | 2 | CH₃ | H | F | NCH₃ | ortho | CH₃ (para to X) |
| 856. | 2 | CH₃ | H | F | NCH₃ | ortho | CH₃ (para to OCHF₂) |
| 857. | 2 | CH₃ | H | F | NCH₃ | meta | OCH₃ (para to X) |
| 858. | 2 | CH₃ | H | F | NCH₃ | meta | OCH₃ (para to OCHF₂) |
| 859. | 2 | CH₃ | H | F | NCH₃ | meta | CH₃ (para to X) |
| 860. | 2 | CH₃ | H | F | NH | ortho | Cl (para to X) |
| 861. | 2 | CH₃ | H | F | NH | ortho | Cl (para to OCHF₂) |
| 862. | 2 | CH₃ | H | F | NH | ortho | F (para to X) |
| 863. | 2 | CH₃ | H | F | NH | ortho | F (para to OCHF₂) |
| 864. | 2 | CH₃ | H | F | NH | meta | OCHF₂ (para to X) |
| 865. | 2 | H | H | F | NCH₂CH₃ | ortho | H |
| 866. | 2 | H | H | F | NCH₂CH₃ | meta | H |
| 867. | 2 | H | H | F | NCH₂CH₃ | para | H |
| 868. | 2 | H | H | F | NCH₂CH₃ | ortho | CH₃ (para to X) |
| 869. | 2 | H | H | F | NCH₂CH₃ | ortho | CH₃ (para to OCHF₂) |
| 870. | 2 | H | H | F | NCH₂CH₃ | meta | OCH₃ (para to X) |
| 871. | 2 | H | H | F | NCH₂CH₃ | meta | OCH₃ (para to OCHF₂) |
| 872. | 2 | H | H | F | NCH₂CH₃ | meta | CH₃ (para to X) |
| 873. | 2 | CH₃ | H | F | NCH₂CH₃ | ortho | H |
| 874. | 2 | CH₃ | H | F | NCH₂CH₃ | meta | H |
| 875. | 2 | CH₃ | H | F | NCH₂CH₃ | para | H |
| 876. | 2 | CH₃ | H | F | NCH₂CH₃ | ortho | CH₃ (para to X) |
| 877. | 2 | CH₃ | H | F | NCH₂CH₃ | ortho | CH₃ (para to OCHF₂) |
| 878. | 2 | CH₃ | H | F | NCH₂CH₃ | meta | OCH₃ (para to X) |
| 879. | 2 | CH₃ | H | F | NCH₂CH₃ | meta | OCH₃ (para to OCHF₂) |
| 880. | 2 | CH₃ | H | F | NCH₂CH₃ | meta | CH₃ (para to X) |
| 881. | 2 | H | H | F | N(CH₂)₂CH₃ | ortho | H |
| 882. | 2 | H | H | F | N(CH₂)₂CH₃ | meta | H |
| 883. | 2 | H | H | F | N(CH₂)₂CH₃ | para | H |
| 884. | 2 | H | H | F | N(CH₂)₂CH₃ | ortho | CH₃ (para to X) |
| 885. | 2 | H | H | F | N(CH₂)₂CH₃ | ortho | CH₃ (para to OCHF₂) |
| 886. | 2 | H | H | F | N(CH₂)₂CH₃ | meta | OCH₃ (para to X) |
| 887. | 2 | H | H | F | N(CH₂)₂CH₃ | meta | OCH₃ (para to OCHF₂) |
| 888. | 2 | H | H | F | N(CH₂)₂CH₃ | meta | CH₃ (para to X) |
| 889. | 2 | CH₃ | H | F | N(CH₂)₂CH₃ | ortho | H |
| 890. | 2 | CH₃ | H | F | N(CH₂)₂CH₃ | meta | H |
| 891. | 2 | CH₃ | H | F | N(CH₂)₂CH₃ | para | H |
| 892. | 2 | CH₃ | H | F | N(CH₂)₂CH₃ | ortho | CH₃ (para to X) |
| 893. | 2 | CH₃ | H | F | N(CH₂)₂CH₃ | ortho | CH₃ (para to OCHF₂) |
| 894. | 2 | CH₃ | H | F | N(CH₂)₂CH₃ | meta | OCH₃ (para to X) |
| 895. | 2 | CH₃ | H | F | N(CH₂)₂CH₃ | meta | OCH₃ (para to OCHF₂) |
| 896. | 2 | CH₃ | H | F | N(CH₂)₂CH₃ | meta | CH₃ (para to X) |
| 897. | 2 | H | H | F | N(CH₂)-cyclopropyl | ortho | H |
| 898. | 2 | H | H | F | N(CH₂)-cyclopropyl | meta | H |
| 899. | 2 | H | H | F | N(CH₂)-cyclopropyl | para | H |
| 900. | 2 | H | H | F | N(CH₂)-cyclopropyl | ortho | CH₃ (para to X) |
| 901. | 2 | H | H | F | N(CH₂)-cyclopropyl | ortho | CH₃ (para to OCHF₂) |
| 902. | 2 | H | H | F | N(CH₂)-cyclopropyl | Meta | OCH₃ (para to X) |
| 903. | 2 | H | H | F | N(CH₂)-cyclopropyl | meta | OCH₃ (para to OCHF₂) |
| 904. | 2 | H | H | F | N(CH₂)-cyclopropyl | meta | CH₃ (para to X) |
| 905. | 2 | CH₃ | H | F | N(CH₂)-cyclopropyl | ortho | H |
| 906. | 2 | CH₃ | H | F | N(CH₂)-cyclopropyl | meta | H |

TABLE A-continued

| No. | n | R¹ | R² | R³ | X | OCHF₂* | R⁵ |
|---|---|---|---|---|---|---|---|
| 907. | 2 | CH₃ | H | F | N(CH₂)-cyclopropyl | para | H |
| 908. | 2 | CH₃ | H | F | N(CH₂)-cyclopropyl | ortho | CH₃ (para to X) |
| 909. | 2 | CH₃ | H | F | N(CH₂)-cyclopropyl | ortho | CH₃ (para to OCHF₂) |
| 910. | 2 | CH₃ | H | F | N(CH₂)-cyclopropyl | meta | OCH₃ (para to X) |
| 911. | 2 | CH₃ | H | F | N(CH₂)-cyclopropyl | meta | OCH₃ (para to OCHF₂) |
| 912. | 2 | CH₃ | H | F | N(CH₂)-cyclopropyl | meta | CH₃ (para to X) |
| 913. | 2 | H | H | F | bond | ortho | H |
| 914. | 2 | H | H | F | bond | meta | H |
| 915. | 2 | H | H | F | bond | para | H |
| 916. | 2 | H | H | F | bond | ortho | CH₃ (para to X) |
| 917. | 2 | H | H | F | bond | ortho | CH₃ (para to OCHF₂) |
| 918. | 2 | H | H | F | bond | meta | OCH₃ (para to X) |
| 919. | 2 | H | H | F | bond | meta | OCH₃ (para to OCHF₂) |
| 920. | 2 | H | H | F | bond | meta | CH₃ (para to X) |
| 921. | 2 | CH₃ | H | F | bond | ortho | H |
| 922. | 2 | CH₃ | H | F | bond | meta | H |
| 923. | 2 | CH₃ | H | F | bond | para | H |
| 924. | 2 | CH₃ | H | F | bond | ortho | CH₃ (para to X) |
| 925. | 2 | CH₃ | H | F | bond | ortho | CH₃ (para to OCHF₂) |
| 926. | 2 | CH₃ | H | F | bond | meta | OCH₃ (para to X) |
| 927. | 2 | CH₃ | H | F | bond | meta | OCH₃ (para to OCHF₂) |
| 928. | 2 | CH₃ | H | F | bond | meta | CH₃ (para to X) |

*Position of OCHF₂ versus X

Examples of compounds according to the present invention are the compounds of the formula I', their pharmacologically tolerated salts and the N-oxides thereof, wherein R⁵ and R⁶ are hydrogen, and the meanings of X, R¹, R², R³, R⁴ and n and the position of X is given in the following table B:

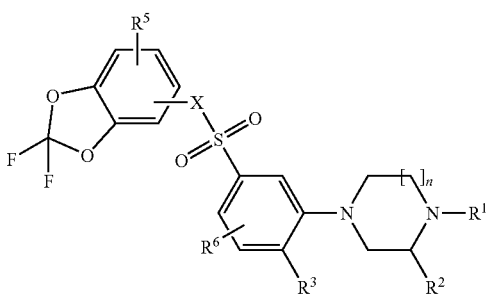

(I')

TABLE B

| | n | R¹ | R² | R³ | X | Position of X vs. difluorodioxolan |
|---|---|---|---|---|---|---|
| 929. | 1 | H | H | OCH₃ | NH | ortho |
| 930. | 1 | H | H | OCH₃ | NH | meta |
| 931. | 1 | CH₃ | H | OCH₃ | NH | ortho |
| 932. | 1 | CH₃ | H | OCH₃ | NH | meta |
| 933. | 2 | H | H | OCH₃ | NH | ortho |
| 934. | 2 | H | H | OCH₃ | NH | meta |
| 935. | 2 | CH₃ | H | OCH₃ | NH | ortho |
| 936. | 2 | CH₃ | H | OCH₃ | NH | meta |
| 937. | 1 | H | H | OCH₃ | NCH₃ | ortho |
| 938. | 1 | H | H | OCH₃ | NCH₃ | meta |
| 939. | 1 | CH₃ | H | OCH₃ | NCH₃ | ortho |
| 940. | 1 | CH₃ | H | OCH₃ | NCH₃ | meta |
| 941. | 2 | H | H | OCH₃ | NCH₃ | ortho |
| 942. | 2 | H | H | OCH₃ | NCH₃ | meta |
| 943. | 2 | CH₃ | H | OCH₃ | NCH₃ | ortho |
| 944. | 2 | CH₃ | H | OCH₃ | NCH₃ | meta |
| 945. | 1 | H | H | OCH₃ | NCH₂CH₃ | ortho |
| 946. | 1 | H | H | OCH₃ | NCH₂CH₃ | meta |
| 947. | 1 | CH₃ | H | OCH₃ | NCH₂CH₃ | ortho |
| 948. | 1 | CH₃ | H | OCH₃ | NCH₂CH₃ | meta |

TABLE B-continued

| | n | R¹ | R² | R³ | X | Position of X vs. difluorodioxolan |
|---|---|---|---|---|---|---|
| 949. | 2 | H | H | OCH₃ | NCH₂CH₃ | ortho |
| 950. | 2 | H | H | OCH₃ | NCH₂CH₃ | meta |
| 951. | 2 | CH₃ | H | OCH₃ | NCH₂CH₃ | ortho |
| 952. | 2 | CH₃ | H | OCH₃ | NCH₂CH₃ | meta |
| 953. | 1 | H | H | OCH₃ | NCH₂CH₂CH₃ | ortho |
| 954. | 1 | H | H | OCH₃ | NCH₂CH₂CH₃ | meta |
| 955. | 1 | CH₃ | H | OCH₃ | NCH₂CH₂CH₃ | ortho |
| 956. | 1 | CH₃ | H | OCH₃ | NCH₂CH₂CH₃ | meta |
| 957. | 2 | H | H | OCH₃ | NCH₂CH₂CH₃ | ortho |
| 958. | 2 | H | H | OCH₃ | NCH₂CH₂CH₃ | meta |
| 959. | 2 | CH₃ | H | OCH₃ | NCH₂CH₂CH₃ | ortho |
| 960. | 2 | CH₃ | H | OCH₃ | NCH₂CH₂CH₃ | meta |
| 961. | 1 | H | H | OCH₃ | Bond | meta |
| 962. | 1 | CH₃ | H | OCH₃ | Bond | ortho |
| 963. | 1 | CH₃ | H | OCH₃ | Bond | meta |
| 964. | 2 | H | H | OCH₃ | Bond | ortho |
| 965. | 2 | H | H | OCH₃ | Bond | meta |
| 966. | 2 | CH₃ | H | OCH₃ | Bond | ortho |
| 967. | 2 | CH₃ | H | OCH₃ | Bond | meta |
| 968. | 1 | H | H | OCHF₂ | NCH₃ | ortho |
| 969. | 1 | H | H | OCHF₂ | NCH₃ | meta |
| 970. | 1 | CH₃ | H | OCHF₂ | NCH₃ | ortho |
| 971. | 1 | CH₃ | H | OCHF₂ | NCH₃ | meta |
| 972. | 2 | H | H | OCHF₂ | NCH₃ | ortho |
| 973. | 2 | H | H | OCHF₂ | NCH₃ | meta |
| 974. | 2 | CH₃ | H | OCHF₂ | NCH₃ | ortho |
| 975. | 2 | CH₃ | H | OCHF₂ | NCH₃ | meta |
| 976. | 1 | H | H | OCHF₂ | NCH₂CH₃ | ortho |
| 977. | 1 | H | H | OCHF₂ | NCH₂CH₃ | meta |
| 978. | 1 | CH₃ | H | OCHF₂ | NCH₂CH₃ | ortho |
| 979. | 1 | CH₃ | H | OCHF₂ | NCH₂CH₃ | meta |
| 980. | 2 | H | H | OCHF₂ | NCH₂CH₃ | ortho |
| 981. | 2 | H | H | OCHF₂ | NCH₂CH₃ | meta |
| 982. | 2 | CH₃ | H | OCHF₂ | NCH₂CH₃ | ortho |
| 983. | 2 | CH₃ | H | OCHF₂ | NCH₂CH₃ | meta |
| 984. | 1 | H | H | OCHF₂ | NCH₂CH₂CH₃ | ortho |
| 985. | 1 | H | H | OCHF₂ | NCH₂CH₂CH₃ | meta |
| 986. | 1 | CH₃ | H | OCHF₂ | NCH₂CH₂CH₃ | ortho |
| 987. | 1 | CH₃ | H | OCHF₂ | NCH₂CH₂CH₃ | meta |
| 988. | 2 | H | H | OCHF₂ | NCH₂CH₂CH₃ | ortho |
| 989. | 2 | H | H | OCHF₂ | NCH₂CH₂CH₃ | meta |
| 990. | 2 | CH₃ | H | OCHF₂ | NCH₂CH₂CH₃ | ortho |
| 991. | 2 | CH₃ | H | OCHF₂ | NCH₂CH₂CH₃ | meta |
| 992. | 1 | H | H | OCHF₂ | Bond | meta |
| 993. | 1 | CH₃ | H | OCHF₂ | Bond | ortho |
| 994. | 1 | CH₃ | H | OCHF₂ | Bond | meta |

TABLE B-continued

| | n | R¹ | R² | R³ | X | Position of X vs. difluorodioxolan |
|---|---|---|---|---|---|---|
| 995. | 2 | H | H | OCHF₂ | Bond | ortho |
| 996. | 2 | H | H | OCHF₂ | Bond | meta |
| 997. | 2 | CH₃ | H | OCHF₂ | Bond | ortho |
| 998. | 2 | CH₃ | H | OCHF₂ | Bond | meta |
| 999. | 1 | H | H | CH₃ | NCH₃ | ortho |
| 1000. | 1 | H | H | CH₃ | NCH₃ | meta |
| 1001. | 1 | CH₃ | H | CH₃ | NCH₃ | ortho |
| 1002. | 1 | CH₃ | H | CH₃ | NCH₃ | meta |
| 1003. | 2 | H | H | CH₃ | NCH₃ | ortho |
| 1004. | 2 | H | H | CH₃ | NCH₃ | meta |
| 1005. | 2 | CH₃ | H | CH₃ | NCH₃ | ortho |
| 1006. | 2 | CH₃ | H | CH₃ | NCH₃ | meta |
| 1007. | 1 | H | H | CH₃ | NCH₂CH₃ | ortho |
| 1008. | 1 | H | H | CH₃ | NCH₂CH₃ | meta |
| 1009. | 1 | CH₃ | H | CH₃ | NCH₂CH₃ | ortho |
| 1010. | 1 | CH₃ | H | CH₃ | NCH₂CH₃ | meta |
| 1011. | 2 | H | H | CH₃ | NCH₂CH₃ | ortho |
| 1012. | 2 | H | H | CH₃ | NCH₂CH₃ | meta |
| 1013. | 2 | CH₃ | H | CH₃ | NCH₂CH₃ | ortho |
| 1014. | 2 | CH₃ | H | CH₃ | NCH₂CH₃ | meta |
| 1015. | 1 | H | H | CH₃ | NCH₂CH₂CH₃ | ortho |
| 1016. | 1 | H | H | CH₃ | NCH₂CH₂CH₃ | meta |
| 1017. | 1 | CH₃ | H | CH₃ | NCH₂CH₂CH₃ | ortho |
| 1018. | 1 | CH₃ | H | CH₃ | NCH₂CH₂CH₃ | meta |
| 1019. | 2 | H | H | CH₃ | NCH₂CH₂CH₃ | ortho |
| 1020. | 2 | H | H | CH₃ | NCH₂CH₂CH₃ | meta |
| 1021. | 2 | CH₃ | H | CH₃ | NCH₂CH₂CH₃ | ortho |
| 1022. | 2 | CH₃ | H | CH₃ | NCH₂CH₂CH₃ | meta |
| 1023. | 1 | H | H | CH₃ | Bond | meta |
| 1024. | 1 | H | H | CH₃ | Bond | ortho |
| 1025. | 1 | CH₃ | H | CH₃ | Bond | meta |
| 1026. | 2 | H | H | CH₃ | Bond | ortho |
| 1027. | 2 | H | H | CH₃ | Bond | meta |
| 1028. | 2 | CH₃ | H | CH₃ | Bond | ortho |
| 1029. | 2 | CH₃ | H | CH₃ | Bond | meta |
| 1030. | 1 | H | H | F | NCH₃ | ortho |
| 1031. | 1 | H | H | F | NCH₃ | meta |
| 1032. | 1 | CH₃ | H | F | NCH₃ | ortho |
| 1033. | 1 | CH₃ | H | F | NCH₃ | meta |
| 1034. | 2 | H | H | F | NCH₃ | ortho |
| 1035. | 2 | H | H | F | NCH₃ | meta |
| 1036. | 2 | CH₃ | H | F | NCH₃ | ortho |
| 1037. | 2 | CH₃ | H | F | NCH₃ | meta |
| 1038. | 1 | H | H | F | NCH₂CH₃ | ortho |
| 1039. | 1 | H | H | F | NCH₂CH₃ | meta |
| 1040. | 1 | CH₃ | H | F | NCH₂CH₃ | ortho |
| 1041. | 1 | CH₃ | H | F | NCH₂CH₃ | meta |
| 1042. | 2 | H | H | F | NCH₂CH₃ | ortho |
| 1043. | 2 | H | H | F | NCH₂CH₃ | meta |
| 1044. | 2 | CH₃ | H | F | NCH₂CH₃ | ortho |
| 1045. | 2 | CH₃ | H | F | NCH₂CH₃ | meta |
| 1046. | 1 | H | H | F | NCH₂CH₂CH₃ | ortho |
| 1047. | 1 | H | H | F | NCH₂CH₂CH₃ | meta |
| 1048. | 1 | CH₃ | H | F | NCH₂CH₂CH₃ | ortho |
| 1049. | 1 | CH₃ | H | F | NCH₂CH₂CH₃ | meta |
| 1050. | 2 | H | H | F | NCH₂CH₂CH₃ | ortho |
| 1051. | 2 | H | H | F | NCH₂CH₂CH₃ | meta |
| 1052. | 2 | CH₃ | H | F | NCH₂CH₂CH₃ | ortho |
| 1053. | 2 | CH₃ | H | F | NCH₂CH₂CH₃ | meta |
| 1054. | 1 | H | H | F | Bond | meta |
| 1055. | 1 | CH₃ | H | F | Bond | ortho |
| 1056. | 1 | CH₃ | H | F | Bond | meta |
| 1057. | 2 | H | H | F | Bond | ortho |
| 1058. | 2 | H | H | F | Bond | meta |
| 1059. | 2 | CH₃ | H | F | Bond | ortho |
| 1060. | 2 | CH₃ | H | F | Bond | meta |

Table C:

Further examples are compounds of the formula I, where $R^6$ is hydrogen, n, $R^1$, $R^3$, X and $R^5$ are as defined in the rows of Table A, wherein $R^2$ is methyl instead of hydrogen (compounds 1061 to 1988) and the physiologically tolerated acid addition salts or the N-oxides thereof.

Table D:

Further examples are compounds of the formula I', where $R^5$ and $R^6$ are hydrogen, n, $R^1$, $R^3$ and X are as defined in the rows of Table B, wherein $R^2$ is methyl instead of hydrogen (compounds 1989 to 2120) and the physiologically tolerated acid addition salts or the N-oxides thereof.

The compounds I and I' according to the invention are prepared in analogy with methods known from the literature. An important approach to the compounds according to the invention is offered by the reaction of a 1-(piperazin-1-yl) or 1-(homopiperazin-1-yl) compound II where $R^3$ is e.g. methyl or methoxy with chlorosulfonic acid and subsequent reaction of the intermediate sulfonyl chloride with an aniline derivative IV as depicted in scheme 1 or with a 2,2-difluorobenzo[1,3]dioxolane derivative IVa as depicted in scheme 1a.

Scheme 1:

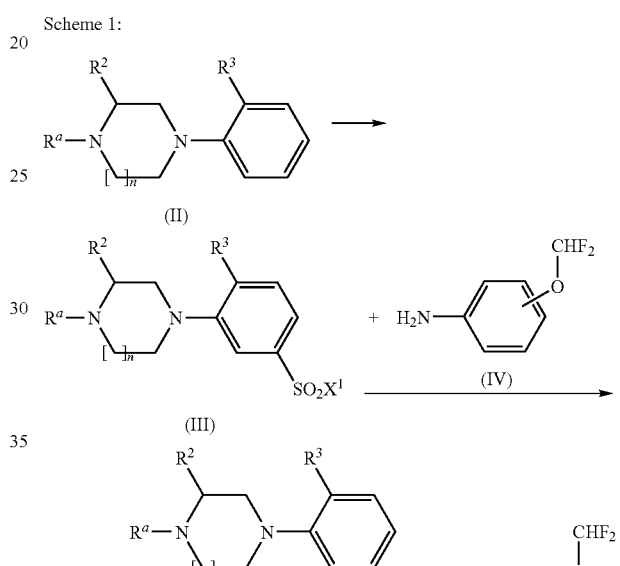

Scheme 1a:

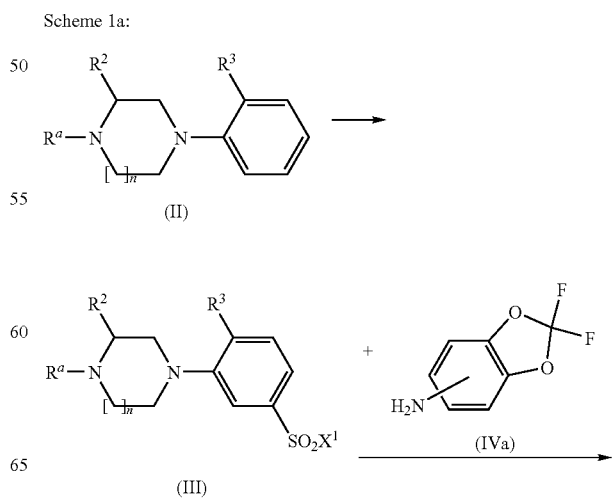

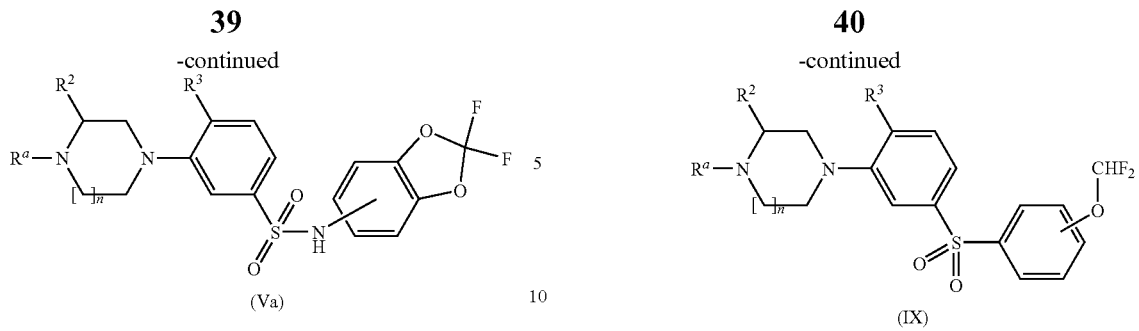

In schemes 1 and 1a, n, $R^2$ and $R^3$ are as defined herein. $R^a$ is a nitrogen protecting group or methyl. Suitable N-protecting groups are described, for example, in P. J. Kocienski "Protecting Groups", $2^{nd}$ ed., Georg Thieme Verlag, Stuttgart 2000, pp 186-237 and in the literature cited therein. Preferred examples of N-protecting groups are e.g. oxycarbonyl groups such as $C_1$-$C_6$-alkoxycarbonyl, e.g. methoxycarbonyl, ethoxycarbonyl and Boc (tert-butoxycarbonyl) and other oxycarbonyl groups such as benzyloxycarbonyl (Cbz), allyloxycarbonyl, 9-fluorenylmethoxycarbonyl (Fmoc) and 2-trimethylsilylethoxycarbonyl (Teoc), or 2-propenyl (allyl). Especially preferred for introduction of a sulfonylchloride group is the trifluoroacetyl group as a protecting group for the piperazine or homopiperazine nitrogen. $X^1$ is a nucleophilically displaceable leaving group, in particular a halogen atom and, especially, chlorine or bromine.

Sulfone compounds of the present invention where X is a bond can be prepared according to schemes 2 and 3, either from compounds VII (which in itself can be prepared from aniline compounds VI where the $NH_2$ group is transformed into a group $X^2$ which can either be e.g. iodine or bromine, via a Sandmeyer reaction) by reaction with a thiophenol compound VIIIa and subsequent oxidation of the sulfide (scheme 2) with suitable oxidizing agents such as oxone or peracids, or by reaction of a compound VII with the salt of a sulfinic acid derivative VIIIb (usually the sodium salt) without the further need for an oxidative step (scheme 3; e.g. Synlett, 2003, 361 Cacchi et al.).

In schemes 2 and 3, n, $R^2$ and $R^3$ are as defined herein. $R^a$ is a nitrogen protecting group or methyl.

Scheme 2:

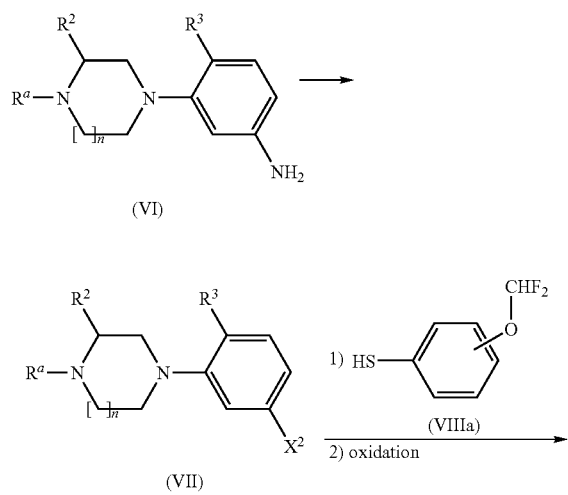

Scheme 3:

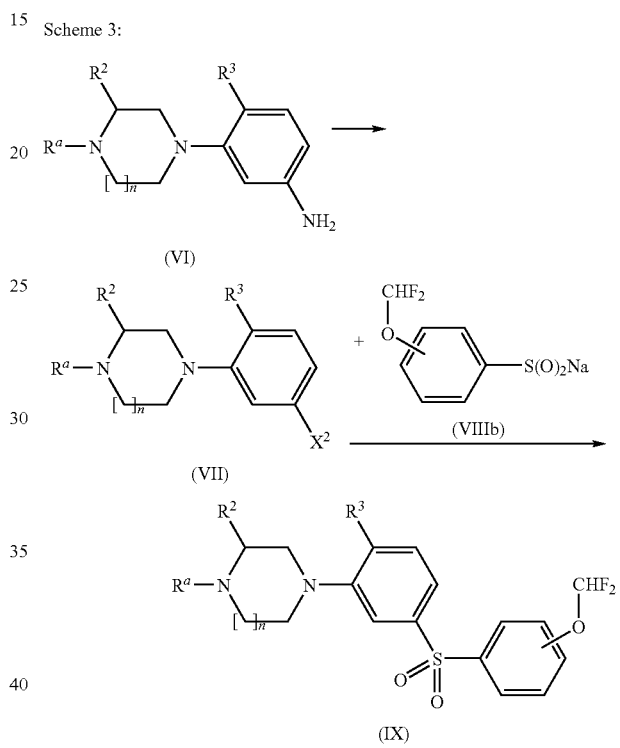

Compounds of formula (IX) can be prepared by the palladium-catalyzed reaction of the sulfinic acid salt VIIIb with compounds VII, wherein $X^2$ is bromine or iodine. A suitable palladium catalyst is tris(dibenzylideneacetone)dipalladium (0) ($Pd_2(dba)_3$). The sulfone (IX) is usually prepared in the presence of Xantphos, a rigid bidendate ligand. The reaction is also usually carried out in the presence of n-tetrabutylammonium chloride. Sulfinate compounds VIIIb are either commercially available or can e.g. be prepared from the corresponding sulfonyl chlorides by reaction with sodium sulfite under basic conditions.

Compounds VIIa, wherein $R^3$ is as defined above, can also be prepared from suitable aniline compounds by reaction with a suitably protected bis(2-chloroethyl)-amine where $R^a$ can e.g. be the p-tolyl-sulfonyl group.

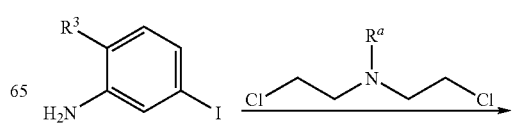

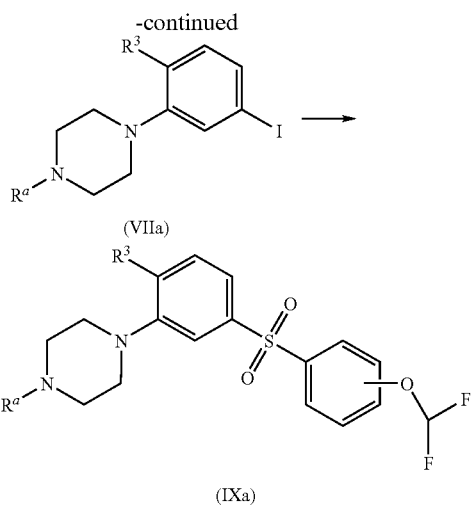

(VIIa)

(IXa)

Compounds of the formulae V and Va, wherein $R^a$ is a nitrogen protecting group, in particular trifluoroacetyl, a $C_1$-$C_6$-alkoxycarbonyl group such as methoxycarbonyl, ethoxycarbonyl and Boc (tert-butoxycarbonyl), are novel and thus form also part of the present invention.

Compounds of the formula V, wherein $R^a$ is methyl correspond to compounds I, wherein $R^1$ is methyl. Compounds of the formula Va, wherein $R^a$ is methyl correspond to compounds I', wherein $R^1$ is methyl.

The reaction depicted in schemes 1 and 1a takes place under the reaction conditions which are customary for preparing arylsulfonamide compounds or arylsulfonic esters, respectively, and which are described, for example, in J. March, Advanced Organic Chemistry, 3$^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108.

The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the abovementioned solvents. The reaction of compound III with compound IV (or compound IVa) is customarily carried out in the presence of an auxiliary base. Suitable bases are inorganic bases, such as sodium carbonate or potassium carbonate, or sodium hydrogen carbonate or potassium hydrogen carbonate, and organic bases, for example trialkylamines, such as triethylamine, or pyridine compounds, such as pyridine, lutidine, 4-dimethylamino-pyridine and the like. The latter compounds can at the same time serve as solvents. The auxiliary base is customarily employed in at least equimolar quantities, based on the amine compound II.

The reaction of compound III with compound IV or IVa, respectively yields compound V or Va, respectively, which, in case $R^a$ is an N-protecting group, is deprotected to yield the compound of the general formula I or I', wherein $R^1$ is hydrogen. Deprotection of the compound V or Va, respectively, can be achieved by standard methods, e.g. by the methods as described in P. J. Kocienski "Protecting Groups", 2$^{nd}$ ed., Georg Thieme Verlag, Stuttgart 2000, pp 186-237 and in the literature cited therein.

Customary methods can then be used to react these compounds with a methylating agent such as methyl iodide or dimethyl sulfate resulting in a compound of the formula I or I', respectively, in which $R^1$ is methyl. The reaction conditions which are required for this methylating reaction are disclosed, for example, in WO 02/083652, Tetrahedron 2000, 56(38) pp. 7553-7560 and Synlett. 2000 (4), pp. 475-480.

For preparing a compound of formula I or I', respectively, in which $R^1$ is methyl, it is likewise possible to react a compound of formula I or I', in which $R^1$ is hydrogen, with formaldehyde in the presence of a reducing agent in a sense of a reductive amination. Suitable reducing agents are borohydrides such as sodium borohydride, sodium cyanoborohydride, sodium triacetoxyborohydride or borane-pyridine. The reductive amination is usually carried out in an organic solvent such as dichloromethane, 1,2-dichloroethane, tetrahydrofuran or acetonitrile.

Reaction of the compound V or Va with an alkylating agent yields a compound of the formula V' or V'a, respectively, wherein n, $R^a$, $R^2$ and $R^3$ are as defined above. In the compound of the formula V' or V'a, respectively, the sulfonamide hydrogen is replaced by $C_1$-$C_4$ alkyl, $C_3$-$C_4$ cycloalkyl, or $C_3$-$C_4$ cycloalkyl-$CH_2$—.

It is possible to react the compound V or Va with a methylating agent such as methyl iodide or dimethyl sulfate to yield a compound of the formula Vc or Vd, respectively, wherein n, $R^a$, $R^2$ and $R^3$ are as defined above.

(Vc)

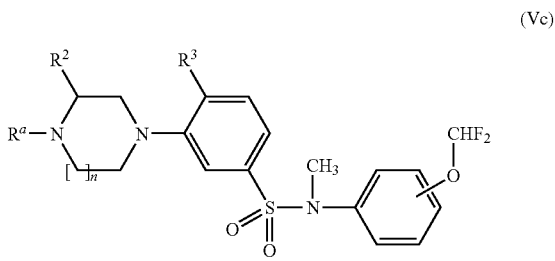

(Vd)

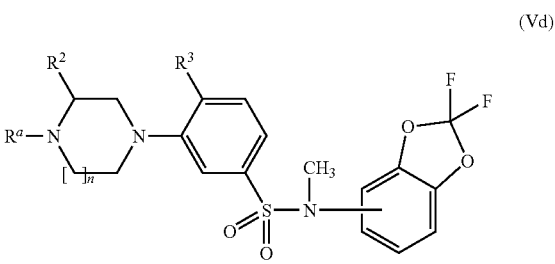

If $R^a$ in formulae Vc or Vd is an N-protecting group, compound Vc or Vd, respectively is deprotected to yield the compound of the general formula I, wherein $R^1$ is hydrogen. Deprotection of the compound Vc or Vd can be achieved by standard methods, e.g. by the methods as described in P. J. Kocienski "Protecting Groups", 2$^{nd}$ ed., Georg Thieme Verlag, Stuttgart 2000, pp 186-237 and in the literature cited therein.

Compounds V and IX where $R^a$ is methyl can best be prepared by reaction of compounds V and IX where $R^a$ is hydrogen with formaldehyde under reducing conditions as described above.

The compounds of the general formula VI are known per se or can be prepared in the manner shown in scheme 4.

Scheme 4:

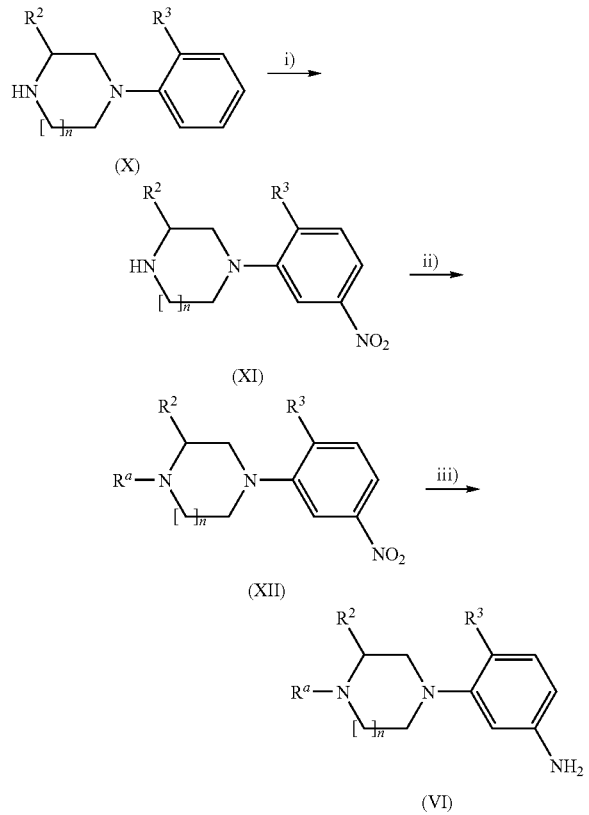

In scheme 4, n, $R^a$, $R^2$ and $R^3$ are as defined herein.

In step i) of scheme 4, the compound X is subjected to a nitration under standard conditions thereby yielding compound XI. Reaction conditions can be taken e.g. from U.S. Pat. No. 6,599,904 or from the working examples of the present application.

In step ii) of scheme 4, the NH-group of compound XI is protected, either by a conventional N-protecting group as defined above or by introducing a methyl group via a methylating agent such as methyl bromide, methyl iodide or dimethyl sulfate. Introduction of an N-protecting group into compound XI can be achieved by standard methods, e.g. by the methods as described in P. J. Kocienski "Protecting Groups", $2^{nd}$ ed., Georg Thieme Verlag, Stuttgart 2000, pp 186-237 and in the literature cited therein. Methylation of compound XI is likewise achieved by standard methods of Organic chemistry.

In step iii), the nitro group in compound XII is reduced to the $NH_2$ group to yield compound VI. The reaction conditions which are required for step iii) correspond to the customary conditions for reducing aromatic nitro groups which have been described extensively in the literature (see, for example, J. March, Advanced Organic Chemistry, 3rd ed., J. Wiley & Sons, New-York, 1985, p. 1183 and the literature cited in this reference). The reduction can be achieved, for example, by reacting the nitro compound XII with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p. 480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of XII to VI can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of compound XII, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of XII with tin(II) chloride is preferably carried out in an inert organic solvent, preferably an alcohol such as methanol, ethanol, isopropanol or butanol.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I and I' are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The compounds of the present invention can be a $5\text{-}HT_6$ receptor agonist, including partial agonistic activity, or a $5\text{-}HT_6$ receptor antagonist, including inverse agonist activity.

The compounds of formulae I and I' according to the present invention, as well as their salts and their N-oxides, have a surprisingly high affinity for $5\text{-}HT_6$ receptors. The high affinity of the compounds according to the invention for $5\text{-}HT_6$ receptors is reflected in very low in-vitro receptor binding constants ($K_i(5\text{-}HT_6)$ values) of as a rule less than 500, 100 or 50 nM (nmol/l), preferably of less than 10 nM and, in particular of less than 5 nM. The displacement of $^3H$-LSD can, for example, be used in receptor binding studies for determining binding affinities to $5\text{-}HT_6$ receptors.

Furthermore the compounds of formulae I and I', as well as their salts and their N-oxides, are highly selective $5\text{-}HT_6$ receptor ligands which, because of their low affinity for other receptors such as dopamine receptors, adrenergic receptors, muscarinic receptors, histamine receptors, opiate receptors, in particular dopamine $D_2$, $\alpha_1$-adrenergic and histamine $H_1$ receptors, give rise to fewer side-effects than other, less selective $5\text{-}HT_6$ ligands.

For instance the $5\text{-}HT_6/D_2$, $5\text{-}HT_6/\alpha_1$-adrenergic or $5\text{-}HT_6/H_1$ selectivities of the compounds according to the present invention, i.e. the ratios $K_i(D_2)/K_i(5\text{-}HT_6)$, $K_i(\alpha_1\text{-}$ adrenergic)/$K_i$(5-HT$_6$) or $K_i$(H$_1$)/$K_i$(5-HT$_6$) of the receptor binding constants, is as a rule at least 25, preferably at least 50, even better at least 100.

The displacement of [$^3$H]SCH23390 or [$^{125}$I]spiperone can be used, for example, for carrying out receptor binding studies on D$_1$, D$_2$ and D$_4$ receptors.

Furthermore the compounds of the present invention because of their structural features are susceptible to display an enhanced brain penetration than other known 5-HT$_6$ receptor ligands.

Because of their binding profile, the compounds of the present invention can be used for treating diseases which respond to 5-HT$_6$ receptor ligands (or which are susceptible to treatment with a 5-HT$_6$ receptor ligand), i.e. they are effective for treating those medical disorders or diseases in which exerting an influence on (modulating) the 5-HT$_6$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-HT$_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, addiction diseases including e.g. drug addiction and obesity.

The addiction diseases include psychic disorders and behavioral disturbances which are caused by the abuse of psychotropic substances, including certain pharmaceuticals, such as sedative, anxiolytica, hypnotics or narcotics (hereinafter also referred to as drug addiction), and also other addiction diseases, such as addiction to gaming (gambling; impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, hallucinogens, NMDA-receptor antagonists such phencyclidine and related cyclidines, dextrometorphan, dextrorphan, ibogaine, ketimine and tiletamine, cannabis, nicotine and alcohol. Other addiction diseases include gaming (gambling), including problem gambling (compulsive gambling, ludomania), computer or video game addiction and internet addiction.

With regard to the treatment of addiction diseases, particular preference is given to those compounds according to the present invention which themselves do not possess any psychotropic effect. This can also be observed in a test using rats, which, after having been administered compounds which can be used in accordance with the invention, reduce their self administration of psychotropic substances, for example cocaine or alcohol.

According to another aspect of the present invention, the compounds according to the invention are suitable for treating disorders whose causes can at least partially be attributed to an anomalous activity of 5-HT$_6$ receptors.

According to another aspect of the present invention, the treatment is directed, in particular, toward those disorders which can be influenced, within the sense of an expedient medicinal treatment, by the binding of preferably exogeneously administered binding partners (ligands) to 5-HT$_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of the present invention can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of the present invention are particularly suitable for treating addiction diseases caused for instance by the abuse of psychotropic substances, such as pharmaceuticals, narcotics, nicotine or alcohol, including psychic disorders and behavioral disturbances related thereto. The compounds of the present invention are likewise particularly suitable for treating addiction diseases which are not caused by the abuse of psychotropic substances, such as gaming (gambling), including problem gambling (compulsive gambling, ludomania), computer or video game addiction and internet addiction. With regard to addiction diseases, the compound of the present invention can be used for the therapy during addiction and also for preventing relapse into addiction.

According to another aspect of the invention the compounds of formulae (I) and (I)', their salts and their N-oxides are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of formulae I or I', their salts and/or their N-oxides are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops.

Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the present invention without limiting its scope.

The compounds were either characterized via proton-NMR in $d_6$-dimethylsulfoxid or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts ($\delta$) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

I. Preparation of the Intermediate Compounds V and IX

I.1 Preparation of the Intermediate Compounds V

PREPARATION EXAMPLE 1

N-(3-Difluoromethoxy-phenyl)-4-methyl-3-[4-(2,2,2-trifluoro-acetyl)-piperazin-1-yl]-benzenesulfonamide

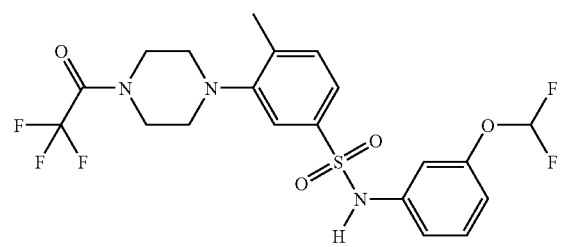

1.1 2,2,2-Trifluoro-1-(4-o-tolyl-piperazin-1-yl)-ethanone

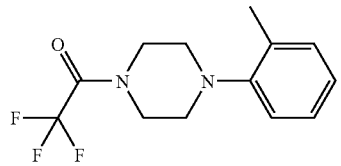

29.9 g of 2,2,2-trifluoroacetic anhydride (104 mmol) were dissolved in 150 mL of dichloromethane, cooled to −20° C., and 20 g of 1-o-tolylpiperazine-1,4-diium chloride (80 mmol)—dissolved in 150 mL of dichloromethane—added dropwise. After stirring for 16 h at room temperature, 400 ml of ice water were added, the organic phase separated, washed twice with water, and the pH adjusted to neutral with 1% aqueous sodium bicarbonate solution. The organic phase was washed with saturated aqueous sodium chloride, dried over sodium sulphate, filtered and the solvent evaporated to yield 21.5 g of product which crystallized upon cooling.

1.2 4-Methyl-3-[4-(2,2,2-trifluoro-acetyl)-piperazin-1-yl]-benzenesulfonyl chloride

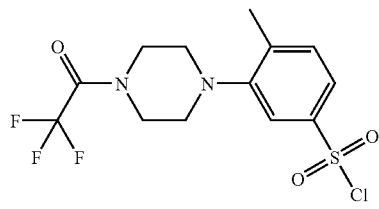

To a solution of 2 g of 2,2,2-trifluoro-1-(4-o-tolyl-piperazin-1-yl)-ethanone (7.35 mmol) in 5 mL of dichloromethane at −5° C. were slowly added 19.7 g of chlorosulfonic acid (169 mmol). After stirring for 2 h at −5° C., the reaction mixture continued stirring for 16 h, thereby slowly allowed to warm to room temperature. After cooling to 0° C., the reaction mixture was slowly added to a water/ice mixture. The aqueous phase was extracted five times with dichloromethane, the combined organic phases washed with aqueous sodium bicarbonate solution and saturated sodium chloride solution. The organic layer was dried over magnesium sulphate, filtered, and the solvent evaporated to yield 2.2 g of product as a white solid.

1.3 N-(3-Difluoromethoxy-phenyl)-4-methyl-3-[4-(2,2,2-trifluoro-acetyl)-piperazin-1-yl]-benzenesulfonamide

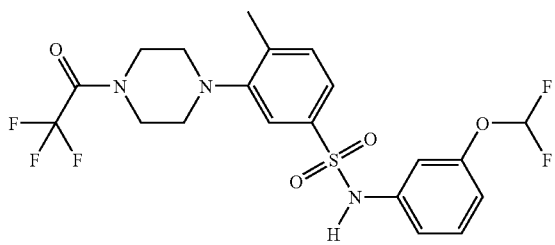

0.429 g of 3-(difluoromethoxy)-aniline (2.7 mmol) were dissolved in 5 mL of pyridine. 1 g of 4-methyl-3-[4-(2,2,2-trifluoro-acetyl)-piperazin-1-yl]-benzenesulfonylchloride (2.7 mmol) were added slowly at room temperature. After stirring for 16 h at room temperature, the reaction mixture was evaporated several times after addition of toluene. The residue was dissolved in dichloromethane and washed several times with 5% aqueous ammonium chloride. The organic phase was then washed with saturated aqueous sodium chloride, dried over sodium sulphate, filtered, and the solvent evaporated. The crude product was purified via silica gel chromatography using dichloromethane/methanol (0-5%) to yield 0.63 g of product.

For the preparation of the intermediate compounds V' or V'a, respectively, i.e. compounds of the formula V or V', respectively, wherein the sulphonamide hydrogen ($R^4$=H) is replaced by $C_1$-$C_4$ alkyl, $C_3$-$C_4$ cycloalkyl, or $C_3$-$C_4$ cycloalkyl-$CH_2$— (compounds V or V', respectively, with $R^4$=$C_1$-$C_4$ alkyl, $C_3$-$C_4$ cycloalkyl, or $C_3$-$C_4$ cycloalkyl-$CH_2$—), where $R^4$ is e.g. a methyl group, the corresponding trifluoroacetyl group has to be removed by reaction under basic conditions, followed by reprotection with tert.butyl-dicarbonate, reaction of this Boc-protected intermediate V with sodium hydride and an alkylating agent, e.g. in case that $R^4$ is methyl, methyl iodide. The N-methylated derivative can then be deprotected at the piperazine or homopiperazine moiety under standard acidic conditions to yield final products.

PREPARATION EXAMPLE 2

N-(3-Difluoromethoxy-phenyl)-4-methyl-3-[4-(2,2,2-trifluoro-acetyl)-[1,4]diazepan-1-yl]-benzenesulfonamide

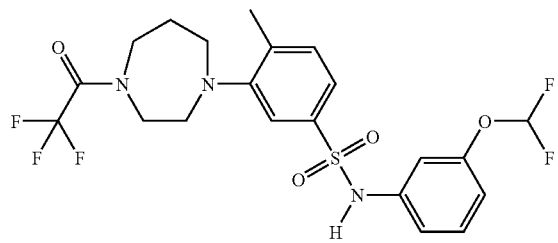

The compound can be prepared as described for PREPARATION EXAMPLE 1 starting from commercially available 1-o-tolyl-[1,4]diazepane.

1.2 Preparation of Intermediate Compounds IX

PREPARATION EXAMPLE 3

1-[5-(3-Difluoromethoxy-benzenesulfonyl)-2-methyl-phenyl]-4-(toluene-4-sulfonyl)-piperazine

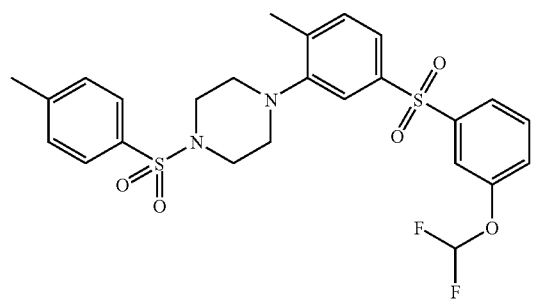

3.1 1-(5-Iodo-2-methyl-phenyl)-4-(toluene-4-sulfonyl)-piperazine

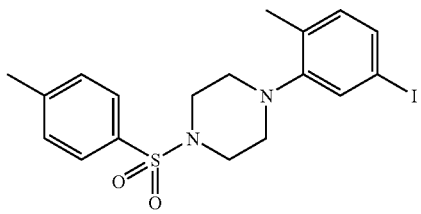

9.97 g of N,N-bis(2-chloroethyl)-4-methylbenzenesulfonamide (30.3 mmol) and 5.03 g of potassium iodide (30.3 mmol) in 75 mL of cyclohexanol were stirred for 1 h at 80° C. After addition of 7.7 g of sodium carbonate (72.7 mmol) and 5.65 g of 5-iodo-2-methyl-aniline (24.2 mmol), stirring continued for 8 h at 160° C. At room temperature, the mixture was filtered, washed with dichloromethane, and the filtrate evaporated to dryness. The residue was dissolved in dichloromethane, filtered, and the solvent evaporated. The remaining residue was trituated with n-heptane and the crystalline product filtered off, washed several times with n-heptane and dried in vacuo to yield 10.7 g of product.

3.2 1-[5-(3-Difluoromethoxy-benzenesulfonyl)-2-methyl-phenyl]-4-(toluene-4-sulfonyl)-piperazine

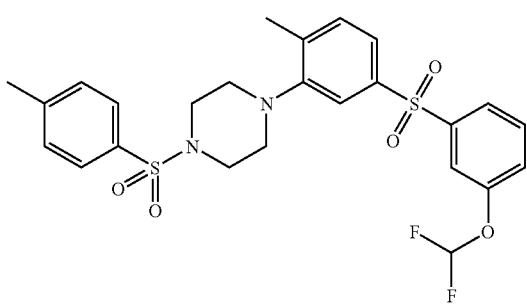

0.521 g of 1-(5-Iodo-2-methyl-phenyl)-4-(toluene-4-sulfonyl)-piperazine (1.14 mmol), 0.315 g of sodium 3-(difluoromethoxy)benzenesulfinate (1.37 mmol), 0.558 g of cesium carbonate (1.713 mmol), 0.026 g of Pd(dba)$_3$ (0.029 mmol), 0.033 g of Xantphos (0.059 mmol) and 0.381 g of tetrabutylammonium chloride (1.37 mmol) were stirred for 8 h in 10 mL of toluene. The reaction mixture was filtered and the solvent evaporated. The crude product was purified via silica gel chromatography with toluene/methanol 20:1 (2.5% triethylamine), fractions containing the product combined and the solvents evaporated to yield 0.386 g of product.

II. Preparation of the Compounds I

EXAMPLE 1

N-(3-Difluoromethoxy-phenyl)-4-methyl-3-piperazin-1-yl-benzenesulfonamide hydrochloride

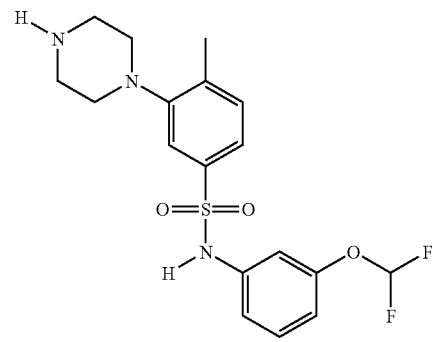

0.63 g of N-(3-Difluoromethoxy-phenyl)-4-methyl-3-[4-(2,2,2-trifluoro-acetyl)-piperazin-1-yl]-benzenesulfonamide (1.28 mmol) were dissolved in 90 ml of methanol, 2.77 ml of 6N aqueous sodium hydroxide (16.6 mmol) added and the reaction stirred at 67° C. for 10 min. 150 mL of water were added, the aqueous layer extracted with ethyl acetate, and the organic phase washed with saturated aqueous sodium chloride, dried over sodium sulfate, filtered and the solvent evaporated. The residue was converted to the hydrochloride salt by addition of HCl in diethyl ether. Evaporation to dryness followed by dissolution of the remaining white solid in water and lyophilisation of the aqueous phase yielded 0.535 g of product.

ESI-MS: 398.1 [M+H]$^+$ $^1$H-NMR (DMSO-d$_6$, 400 Hz): δ [ppm] 10.45 (s, 1H), 9.0 (broad, 2H), 7.3-7.45 (m, 3H), 7.25 (m, 1H), 7.15 (t, 1H), 6.95 (d, 1H), 6.9 (s, 1H), 6.85 (d, 1H), 3.25 (broad, 4H), 3.0 (broad, 4H), 2.25 (s, 3H).

EXAMPLE 2

3-[1,4]Diazepan-1-yl-N-(3-difluoromethoxy-phenyl)-4-methyl-benzenesulfonamide hydrochloride

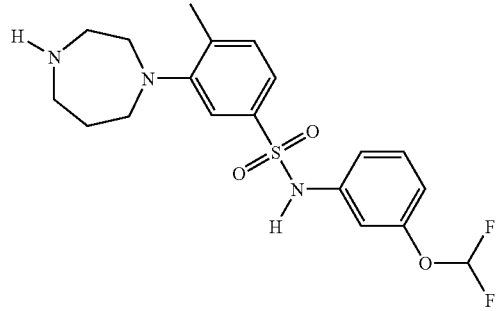

The product was obtained as described for Example 1 by reaction of N-(3-difluoromethoxy-phenyl)-4-methyl-3-[4-(2,2,2-trifluoro-acetyl)-[1,4]diazepan-1-yl]-benzenesulfonamide with aqueous sodium hydroxide.

ESI-MS: 412.1 [M+H]$^+$ $^1$H-NMR (DMSO-d$_6$, 400 Hz): δ [ppm] 10.5 (s, 1H), 9.55 (s, broad, 2H), 7.45 (s, 1H), 7.0-7.4 (several m, 4H), 7.0 (d, 1H), 6.95 (s, 1H), 6.8 (d, 1H), 4.0 (s, broad, 2H), 3.2 (broad, 6H), 3.0 (m, 2H), 2.25 (s, 3H).

EXAMPLE 3

1-[5-(3-Difluoromethoxy-benzenesulfonyl)-2-methyl-phenyl]-piperazine hydrochloride

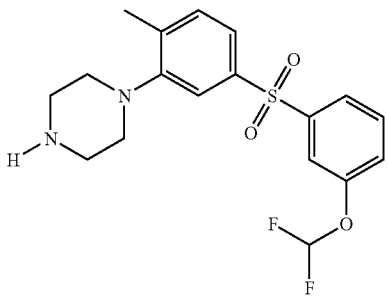

0.75 g of 4-hydroxy-benzoic acid (7.06 mmol) and 2.485 mL of 32% HBr in acetic acid (72.4 mmol) were mixed under stirring and the suspension cooled to 0° C. 0.379 g of 1-[5-(3-difluoromethoxy-benzenesulfonyl)-2-methyl-phenyl]-4-(toluene-4-sulfonyl)-piperazine (0.706 mmol) dissolved in 5 mL of acetic acid were added and the reaction mixture stirred for 16 h. Additional 30 equivalents of HBr in acetic acid were added, stirred for 18 h, and the reaction added slowly to ice water. The pH was adjusted to neutral conditions with addition of aqueous ammonia, the aqueous layer extracted three times with dichloromethane, the combined organic layers dried over magnesium sulphate, filtered and the solvent evaporated. The crude product was purified via silica gel chromatography using toluene/methanol 5:1 (2.5% triethylamine), the solvents evaporated and the residue redissolved in a small amount of ethyl acetate. The hydrochloride was precipitated by addition of 2 N hydrochlorid acid in diethyl ether yielding 0.059 g of product.

ESI-MS: 383.1 [M+H]+

$^1$H-NMR (DMSO-$d_6$, 400 Hz): δ [ppm] 9.5 (s broad, 2H), 7.8 (d, 1H), 7.7 (s, 1H), 7.65 (m, 1H), 7.6 (d, 1H), 7.5 (m, 2H), 7.45 (d, 1H), 7.4 (t, 1H), 3.2 (broad, 4H), 3.1 (broad, 4H), 2.3 (s, 3H).

The compounds of Examples 4 to 49 can be prepared in a manner analogous to the preparations described above.

EXAMPLE 4

N-(2-Difluoromethoxy-phenyl)-N-methyl-3-(4-methyl-piperazin-1-yl)-benzene-sulfonamide hydrochloride

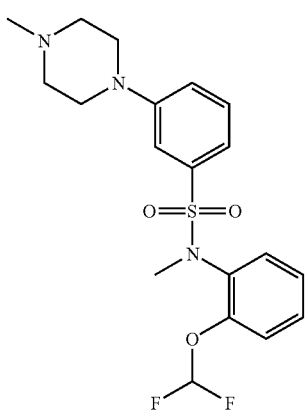

ESI-MS: 412.1 [M+H]+

$^1$H-NMR (DMSO-$d_6$, 400 Hz): δ [ppm] 6.9-7.5 (several m, 9H), 3.5 (broad, 8H), 3.1 (s, 3H), 2.75 (s, 3H).

EXAMPLE 5

N-(2-Difluoromethoxy-phenyl)-4-methyl-3-(4-methyl-piperazin-1-yl)-benzene-sulfonamide hydrochloride

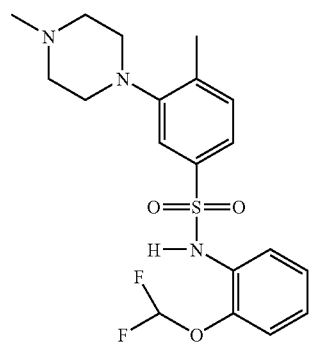

ESI-MS: 412.1 [M+H]+

$^1$H-NMR (DMSO-$d_6$, 400 Hz): δ [ppm] 11.4 (broad, 1H), 9.9 (s, 1H), 7.4 (s, 1H), 7.05-7.35 (several m, 6H), 6.95 (t, 1H), 3.45 (broad, 2H), 3.2 (broad, 2H), 3.1 (broad, 4H), 2.8 (s, 3H), 2.3 (s, 3H).

EXAMPLE 6

N-(3-Difluoromethoxy-4-methyl-phenyl)-4-methyl-3-piperazin-1-yl-benzene-sulfonamide hydrochloride

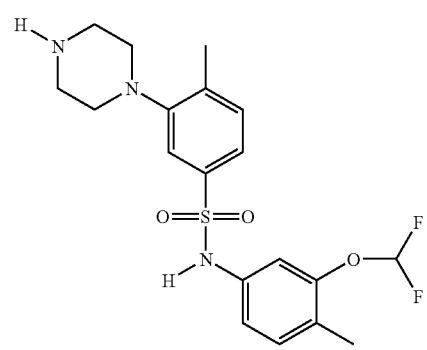

ESI-MS: 412.1 [M+H]+

$^1$H-NMR (DMSO-$d_6$, 400 Hz): δ [ppm] 9.7 (broad, 3H), 7.45 (s, 1H), 7.38 (d, 1H), 7.32 (d, 1H), 7.15 (d, 1H), 7.05 (t, 1H), 6.95 (s, 1H), 6.9 (d, 1H), 3.2 (broad, 4H), 3.0 (broad, 4H), 2.25 (s, 3H), 2.05 (s, 3H).

EXAMPLE 7

N-(4-Difluoromethoxy-phenyl)-4-methyl-3-piperazin-1-yl-benzenesulfonamide hydrochloride

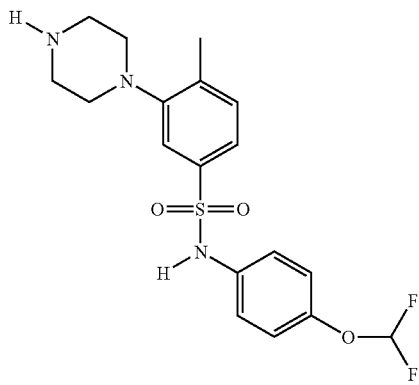

ESI-MS: 398.1 [M+H]$^+$ $^1$H-NMR (DMSO-d$_6$, 400 Hz): δ [ppm] 10.35 (broad, 1H), 9.55 (broad, 2H), 7.25-7.45 (several m, 3H), 7.15 (t, 1H), 7.15 (d, 2H), 7.05 (d, 2H), 3.2 (broad, 4H), 3.05 (broad, 4H), 2.25 (s, 3H).

EXAMPLE 8

N-(2,2-Difluoro-benzo[1,3]dioxol-4-yl)-4-methyl-3-piperazin-1-yl-benzenesulfonamide hydrochloride

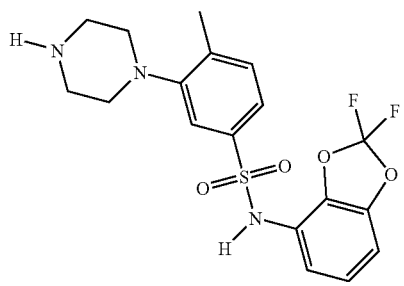

ESI-MS: 412.1 [M+H]$^+$ $^1$H-NMR (DMSO-d$_6$, 400 Hz): δ [ppm] 9.6 (broad, 1H), 7.25-7.45 (several m, 3H), 7.2 (d, 1H), 7.1 (m, 1H), 6.9 (d, 1H), 3.2 (broad, 4H), 3.05 (broad, 4H), 2.3 (broad, 3H).

EXAMPLE 9

N-Cyclopropylmethyl-N-(2-difluoromethoxy-phenyl)-4-methyl-3-piperazin-1-yl-benzenesulfonamide hydrochloride

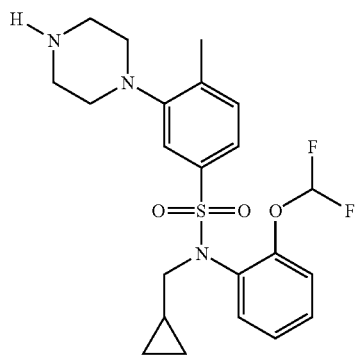

ESI-MS: 452.2 [M+H]$^+$ $^1$H-NMR (DMSO-d$_6$, 400 Hz): δ [ppm] 9.55 (broad, 2H), 7.05-7.5 (several m, 7H), 7.1 (t, 1H), 3.35 (m, 2H), 3.2 (broad, 4H), 3.05 (broad, 4H), 2.3 (broad, 3H), 0.75 (m, 1H), 0.3 (m, 2H), −0.05 (m, 2H).

EXAMPLE 10

N-Cyclopropylmethyl-N-(3-difluoromethoxy-phenyl)-4-methyl-3-piperazin-1-yl-benzenesulfonamide hydrochloride

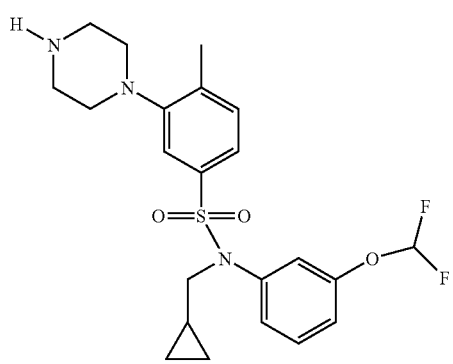

ESI-MS: 452.2 [M+H]$^+$ $^1$H-NMR (DMSO-d$_6$, 400 Hz): δ [ppm] 9.6 (broad, 2H), 6.8-7.55 (several m, 8H), 3.4 (m broad, 2H), 3.2 (broad, 4H), 3.05 (broad, 4H), 2.35 (broad, 3H), 0.75 (m broad, 1H), 0.35 (m broad, 2H), 0.0 (m broad, 2H).

EXAMPLE 11

N-(2-Difluoromethoxy-phenyl)-4-methyl-3-piperazin-1-yl-N-propyl-benzene-sulfonamide hydrochloride

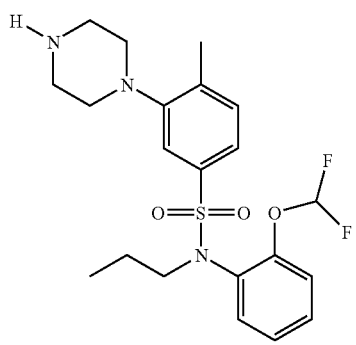

ESI-MS: 440.1 [M+H]$^+$ $^1$H-NMR (DMSO-d$_6$, 400 Hz): δ [ppm] 9.55 (broad, 2H), 7.4 (m, 2H), 7.3 (d, 1H), 7.25 (d, 2H), 7.1 (t, 1H), 7.1 (m, 2H), 3.4 (m, 2H), 3.2 (broad, 4H), 3.05 (broad, 4H), 2.3 (s, 3H), 1.3 (m, 2H), 0.8 (t, 3H).

EXAMPLE 12

N-(3-Difluoromethoxy-phenyl)-4-methyl-3-piperazin-1-yl-N-propyl-benzenesulfonamide hydrochloride

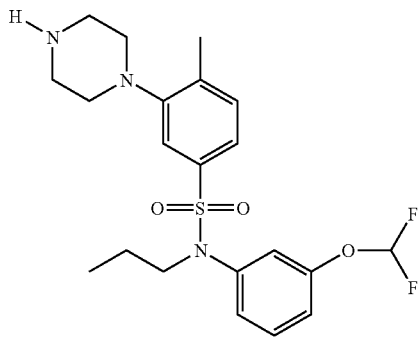

ESI-MS: 440.1 [M+H]+

$^1$H-NMR (DMSO-d$_6$, 400 Hz): δ [ppm] 9.4 (broad, 2H), 7.4 (m, 2H), 7.3 (t, 1H), 7.25 (d, 1H), 7.15 (d, 1H), 6.95 (s, 1H), 6.95 (d, 1H), 6.85 (s, 1H), 3.45 (t, 2H), 3.2 (broad, 4H), 3.0 (broad, 4H), 2.35 (s, 3H), 1.3 (m, 2H), 0.8 (t, 3H).

EXAMPLE 13

N-(3-Difluoromethoxy-phenyl)-N-ethyl-4-methyl-3-piperazin-1-yl-benzene sulfonamide hydrochloride

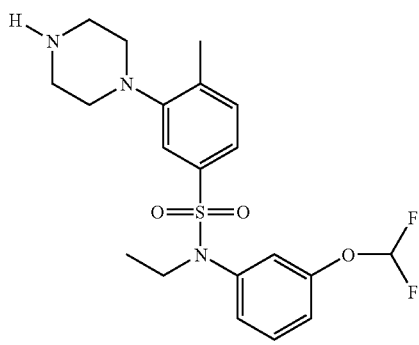

ESI-MS: 426.1 [M+H]+

$^1$H-NMR (DMSO-d$_6$, 400 Hz): δ [ppm] 9.35 (broad, 2H), 7.4 (m, 2H), 7.25 (t, 1H), 7.25 (d, 1H), 7.2 (d, 1H), 7.0 (s, 1H), 6.95 (d, 1H), 6.85 (s, 1H), 3.55 (m, 2H), 3.2 (broad, 4H), 3.0 (broad, 4H), 2.35 (s, 3H), 0.95 (t, 3H).

EXAMPLE 14

N-(3-Difluoromethoxy-phenyl)-4,N-dimethyl-3-piperazin-1-yl-benzenesulfonamide hydrochloride

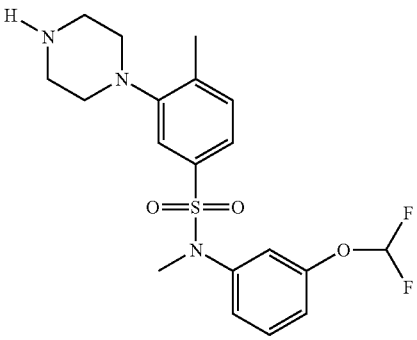

ESI-MS: 412.1 [M+H]+

$^1$H-NMR (DMSO-d$_6$, 400 Hz): δ [ppm] 9.5 (broad, 2H), 7.4 (m, 2H), 7.3 (t, 1H), 7.2 (d, 1H), 7.1 (d, 1H), 7.0 (d, 1H), 6.95 (s, 1H), 6.9 (s, 1H), 3.55 (m, 2H), 3.2 (broad, 4H), 3.1 (s, 3H), 2.95 (broad, 4H), 2.35 (s, 3H).

20

EXAMPLE 15

N-(2-Difluoromethoxy-phenyl)-N-ethyl-4-methyl-3-piperazin-1-yl-benzene sulfonamide hydrochloride

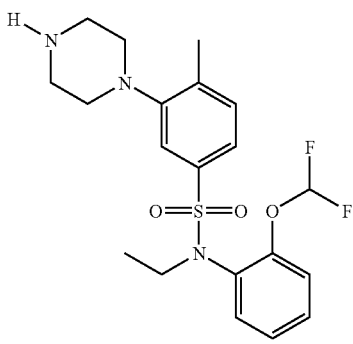

ESI-MS: 426.1 [M+H]+

$^1$H-NMR (DMSO-d$_6$, 400 Hz): δ [ppm] 9.55 (broad, 2H), 7.4 (m, 2H), 7.35 (d, 1H), 7.25 (m, 2H), 7.15 (t, 1H), 7.15 (d, 1H), 7.1 (d, 1H), 3.5 (m, 2H), 3.2 (broad, 4H), 3.05 (broad, 4H), 2.35 (s, 3H), 0.95 (t, 3H).

EXAMPLE 16

N-(2-Difluoromethoxy-phenyl)-N-methyl-4-methyl-3-piperazin-1-yl-benzene sulfonamide hydrochloride

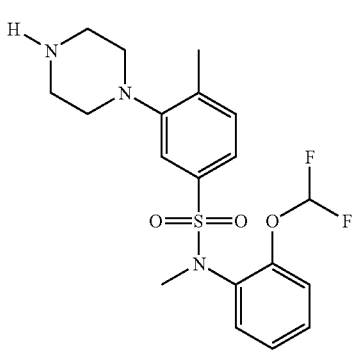

ESI-MS: 412.1 [M+H]+

¹H-NMR (DMSO-d₆, 400 Hz): δ [ppm] 9.7 (broad, 2H), 7.4 (m, 2H), 7.3 (d, 1H), 7.2 (m, 2H), 7.1 (t, 1H), 7.1 (m, 2H), 3.2 (broad, 4H), 3.05 (broad, 4H), 3.05 (s, 3H), 2.3 (s, 3H).

EXAMPLE 17

N-(2-Difluoromethoxy-phenyl)-4-methyl-3-piperazin-1-yl-benzenesulfonamide hydrochloride

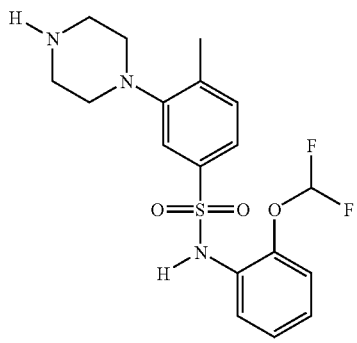

ESI-MS: 398.1 [M+H]+

¹H-NMR (DMSO-d₆, 400 Hz): δ [ppm] 9.85 (s, 1H), 9.1 (broad, 2H), 7.3-7.4 (m, 3H), 7.25 (d, 1H), 7.1-7.2 (m, 3H), 6.9 (t, 1H), 3.25 (broad, 4H), 3.0 (broad, 4H), 2.3 (s, 3H).

EXAMPLE 18

N-(3-Difluoromethoxy-4-methyl-phenyl)-4-methoxy-3-piperazin-1-yl-benzene-sulfonamide hydrochloride

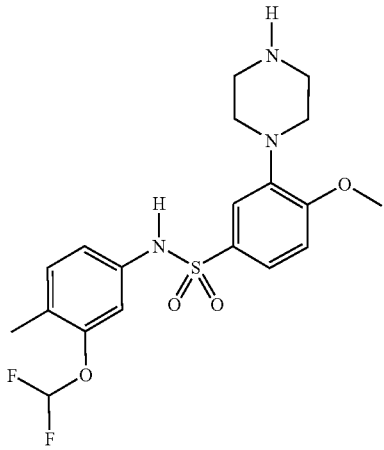

ESI-MS: 428.1 [M+H]+

¹H-NMR (DMSO-d₆, 400 Hz): δ [ppm] 7.3 (d, 1H), 7.2 (s, 1H), 7.1 (d, 1H), 7.0 (d, 1H), 6.8-7.2 (t, 1H), 6.9 (s, 1H), 6.8 (d, 1H), 3.8 (s, 3H), 2.8 (s, 8H), 2.1 (s, 3H).

EXAMPLE 19

N-(4-Difluoromethoxy-phenyl)-4-methoxy-3-piperazin-1-yl-benzenesulfonamide hydrochloride

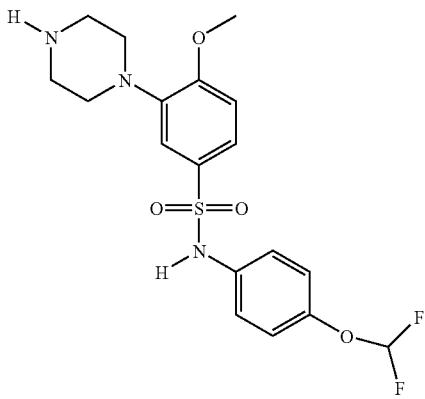

ESI-MS: 414.1 [M+H]+

¹H-NMR (DMSO-d₆, 400 Hz): δ [ppm] 10.25 (s, 1H), 9.5 (broad, 2H), 7.35 (d, 1H), 7.25 (d, 1H), 7.15 (d, 2H), 7.15 (t, 1H), 7.05 (m, 3H), 3.8 (s, 3H), 3.2 (broad, 8H).

EXAMPLE 20

3-[1,4]Diazepan-1-yl-N-(2-difluoromethoxy-phenyl)-4-methyl-benzenesulfonamide hydrochloride

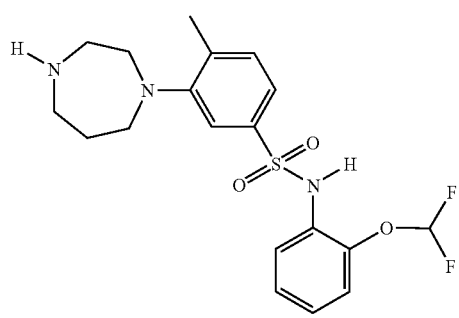

ESI-MS: 412.1 [M+H]+

¹H-NMR (DMSO-d₆, 400 Hz): δ [ppm] 9.8 (s, 1H), 9.4 (s broad, 2H), 7.4 (s, 1H), 7.2-7.3 (m, 3H), 7.1-7.2 (m, 3H), 6.9 (t, 1H), 3.25 (m, 6H), 3.0 (m, 2H), 2.3 (s, 3H), 2.0 (m, 2H).

EXAMPLE 21

3-[1,4]Diazepan-1-yl-N-(3-difluoromethoxy-4-methyl-phenyl)-4-methyl-benzenesulfonamide hydrochloride

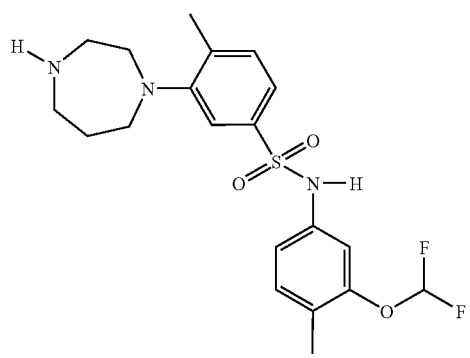

ESI-MS: 426.1 [M+H]$^+$ $^1$H-NMR (DMSO-d$_6$, 400 Hz): δ [ppm] 10.3 (s, 1H), 9.4 (s broad, 2H), 7.4 (s, 1H), 7.3 (m, 2H), 7.15 (d, 1H), 7.05 (t, 1H), 6.95 (m, 1H), 6.85 (m, 1H), 3.2-3.3 (m, 6H), 3.0 (m, 2H), 2.3 (s, 3H), 2.1 (s, 3H), 2.05 (m, 2H).

EXAMPLE 22

N-(2-Difluoromethoxy-4-methyl-phenyl)-4-methyl-3-piperazin-1-yl-benzenesulfonamide hydrochloride

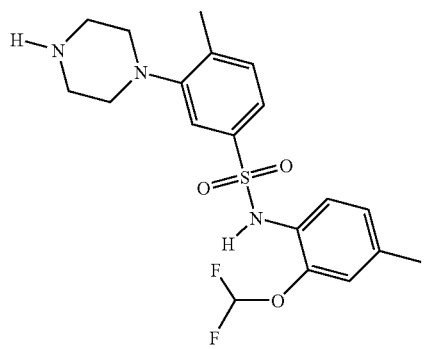

ESI-MS: 412.1 [M+H]$^+$ $^1$H-NMR (DMSO-d$_6$, 400 Hz): δ [ppm] 9.6 (broad, 3H), 7.4 (s, 1H), 7.3 (m, 2H), 7.1 (d, 1H), 6.9-7.0 (m, 2H), 6.9 (t, 1H), 3.2 (broad, 4H), 3.05 (broad, 4H), 2.3 (s, 3H), 2.25 (s, 3H).

EXAMPLE 23

N-(2-Difluoromethoxy-5-methyl-phenyl)-4-methyl-3-piperazin-1-yl-benzenesulfonamide hydrochloride

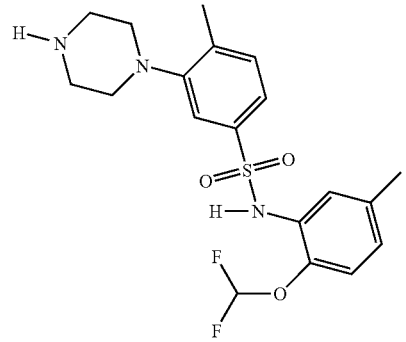

ESI-MS: 412.1 [M+H]$^+$ $^1$H-NMR (DMSO-d$_6$, 400 Hz): δ [ppm] 9.4-9.9 (broad, 3H), 7.4 (s, 1H), 7.3 (m, 2H), 7.1 (s, 1H), 6.9-7.0 (m, 2H), 6.85 (t, 1H), 3.2 (broad, 4H), 3.05 (broad, 4H), 2.3 (s, 3H), 2.2 (s, 3H).

EXAMPLE 24

N-(3-Difluoromethoxy-phenyl)-4-methoxy-3-piperazin-1-yl-benzenesulfonamide hydrochloride

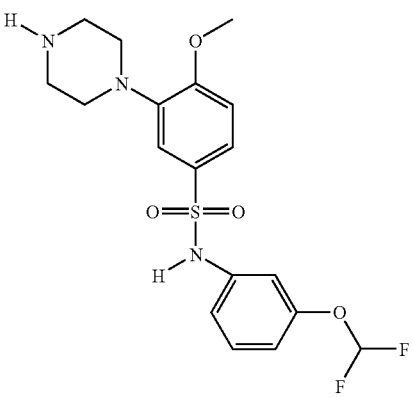

ESI-MS: 414.1 [M+H]$^+$ $^1$H-NMR (DMSO-d$_6$, 400 Hz): δ [ppm] 10.5 (s, 1H), 9.6 (s broad, 2H), 7.4 (d, 1H), 7.3 (s, 1H), 7.25 (m, 1H), 7.15 (t, 1H), 7.1 (d, 1H), 7.0 (m, 1H), 6.95 (s, 1H), 6.8 (d, 1H), 3.8 (s, 3H), 3.1-3.2 (broad, 8H).

EXAMPLE 25

N-(3-Difluoromethoxy-4-methoxy-phenyl)-4-methoxy-3-piperazin-1-yl-benzenesulfonamide hydrochloride

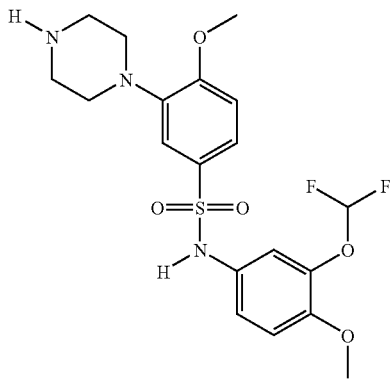

ESI-MS: 444.1 [M+H]$^+$ $^1$H-NMR (DMSO-d$_6$, 400 Hz): δ [ppm] 10.05 (s, 1H), 9.3 (s broad, 2H), 7.35 (d, 1H), 7.25 (s, 1H), 6.8-7.1 (several m, 5H), 3.8 (s, 1H), 3.7 (s, 3H), 3.2 (s broad, 4H), 3.15 (s broad, 4H).

EXAMPLE 26

N-(2-Difluoromethoxy-phenyl)-4-methoxy-3-piperazin-1-yl-benzenesulfonamide hydrochloride

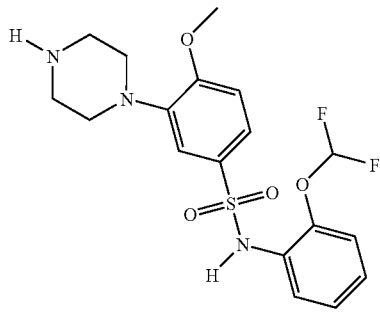

ESI-MS: 414.1 [M+H]$^+$ $^1$H-NMR (DMSO-d$_6$, 400 Hz): δ [ppm] 9.8 (s, 1H), 9.7 (s broad, 2H), 7.35 (d, 1H), 7.3 (s, 1H), 7.25 (d, 1H), 7.1-7.2 (several m, 3H), 7.05 (d, 1H), 7.0 (t, 1H), 3.8 (s, 3H), 3.2 (broad, 8H).

EXAMPLE 27

N-(2-Difluoromethoxy-phenyl)-4-methoxy-N-methyl-3-piperazin-1-yl-benzenesulfonamide hydrochloride

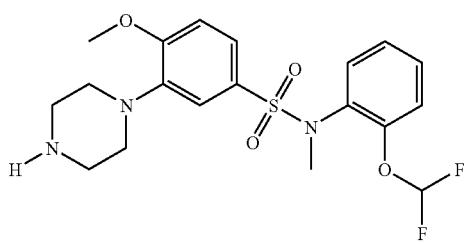

27.1 tert-butyl 4-(5-(N-(2-(difluoromethoxy)phenyl)sulfamoyl)-2-methoxyphenyl)piperazine-1-carboxylate 1 g of N-(2-(difluoromethoxy)phenyl)-4-methoxy-3-(piperazin-1-yl)benzenesulfonamide (2.419 mmol) were dissolved in 15 mL of tetrahydrofuran. 0.674 mL of triethylamine (4.84 mmol) were added, followed by addition of 0.528 g of di-tert-butyl dicarbonate (2.419 mmol) in 2 mL of tetrahydrofurane. The reaction mixture was stirred at room temperature for 16 h. After evaporation of the solvent, the residue was dissolved in dichloromethane, washed with 5% aqueous citric acid. The organic phase was washed with saturated aqueous sodium chloride, dried over sodium sulphate, filtered, and the solvent evaporated. The crude product containing ca. 25% of the bis-boc derivative was used without further purification in the next step (1.2 g).

27.2 tert-butyl 4-(5-(N-(2-(difluoromethoxy)phenyl)methyl-sulfamoyl)-2-methoxyphenyl)piperazine-1-carboxylate 0.15 g of tert-butyl 4-(5-(N-(2-(difluoromethoxy)phenyl)sulfamoyl)-2-methoxyphenyl)piperazine-1-carboxylate (0.219 mmol) were dissolved in 5 mL of dimethylformamide. 11.4 mg of sodium hydride (0.285 mmol, 60%) were added and the reaction stirred at 50° C. for 20 min. At room temperature, 0.018 mL of methyl iodide (0.285 mmol) were added. Stirring was continued for 16 h at room temperature followed by addition of additional 0.018 mL of methyl iodide and stirring for 16 h. The solvent was evaporated, the residue dissolved in dichloromethane and washed with saturated aqueous sodium chloride. The organic layer was dried over sodium sulfate, filtered and the solvent evaporated. Purification via silica gel chromatography (Redisep NP-cartridge) with cyclohexane/ethyl acetate (0-50%) yielded 0.104 g of the title compound.

ESI-MS: 528.2 [M+H]$^+$

27.3 N-(2-Difluoromethoxy-phenyl)-4-methoxy-N-methyl-3-piperazin-1-yl-benzenesulfonamide hydrochloride 0.104 g tert-butyl 4-(5-(N-(2-(difluoromethoxy)phenyl)methyl-sulfamoyl)-2-methoxyphenyl)piperazine-1-carboxylate (0.197 mmol) were dissolved in 5 mL of dichloromethane. At room temperature, 0.296 mL of 2 N aqueous hydrochloric acid (0.591 mmol) were added and the reaction stirred for 16 h and 2 h at 35° C. After addition of methanol, stirring continued for 1 h before the solvents were evaporated and the residue co-destilled several times with diethyl ether to remove residual hydrochloric acid. The remaining solid was dissolved in water (pH 4), extracted several times with dichloromethane, and aqueous layer lyophilized to yield 0.08 g of the title compound.

ESI-MS: 428.1 [M+H]$^+$ $^1$H-NMR (DMSO-d$_6$, 400 Hz): δ [ppm] 9.3 (s broad 2H), 7.45 (m, 1H), 7.4 (m, 1H), 7.25 (m, 2H), 7.2 (d, 1H), 7.1 (d, 1H), 7.1 (t, 1H), 7.0 (s, 1H), 3.9 (s, 3H), 3.2 (s broad, 4H), 3.15 (s broad, 4H), 3.05 (s, 3H).

Examples 9, 10, 11, 12, 13, 14, 15, 16, 28, 29, 30, 31, 32, 33, 34, 36, 39, and 43 were prepared as described for Example 27, using either methyl iodide, ethyl iodide, propyl bromide, isopropyl bromide or cyclopropyl-methylen-bromide as alkylating reagents.

EXAMPLE 28

N-(3-Difluoromethoxy-4-methoxy-phenyl)-4-methoxy-N-methyl-3-piperazin-1-yl-benzenesulfonamide hydrochloride

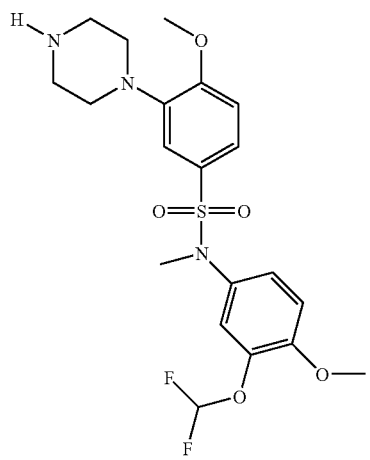

ESI-MS: 458.1 [M+H]$^+$ $^1$H-NMR (DMSO-d$_6$, 400 Hz): δ [ppm] 9.7 (s broad, 2H), 9.05 (s broad, 1H), 7.2 (m, 1H), 7.25 (m, 2H), 7.05 (t, 1H), 6.95 (m, 1H), 6.9 (s, 1H), 6.8 (s, 1H), 3.9 (s, 3H), 3.85 (s, 3H), 3.2 (broad, 8H), 3.05 (s, 3H).

EXAMPLE 29

N-(3-Difluoromethoxy-phenyl)-N-ethyl-4-methoxy-3-piperazin-1-yl-benzenesulfonamide hydrochloride

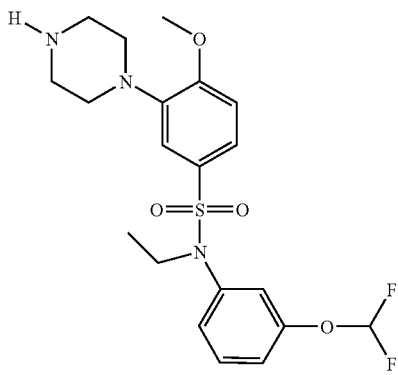

ESI-MS: 442.2 [M+H]$^+$ $^1$H-NMR (DMSO-d$_6$, 400 Hz): δ [ppm] 9.5 (s broad, 2H), 7.4 (m, 1H), 7.25 (t, 1H), 7.25 (m, 1H), 7.1-7.2 (several m, 2H), 6.9 (d, 1H), 6.8 (s, 2H), 3.85 (s, 3H), 3.5 (m, 2H), 3.2 (s broad, 4H), 3.15 (s broad, 4H), 0.9 (t, 3H).

EXAMPLE 30

N-(3-Difluoromethoxy-4-methoxy-phenyl)-N-ethyl-4-methoxy-3-piperazin-1-yl-benzenesulfonamide hydrochloride

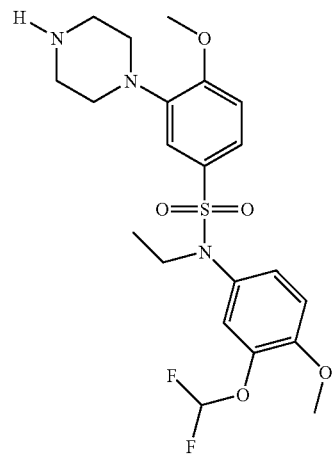

ESI-MS: 472.2 [M+H]$^+$ $^1$H-NMR (DMSO-d$_6$, 400 Hz): δ [ppm] 9.3 (s broad, 2H), 7.25 (d, 1H), 7.1-7.2 (m, 2H), 7.0 (t, 1H), 6.95 (m, 1H), 6.9 (s, 1H), 6.8 (s, 1H), 3.9 (s, 3H), 3.85 (s, 3H), 3.5 (m, 2H), 3.2 (s broad, 4H), 3.15 (s broad, 4H), 0.95 (t, 3H).

EXAMPLE 31

N-(2-Difluoromethoxy-phenyl)-N-ethyl-4-methoxy-3-piperazin-1-yl-benzenesulfonamide hydrochloride

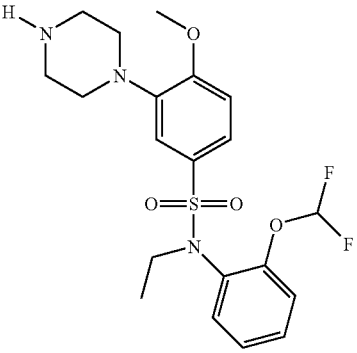

ESI-MS: 442.1 [M+H]$^+$ $^1$H-NMR (DMSO-d$_6$, 400 Hz): δ [ppm] 9.5 (s, broad, 2H), 7.45 (m, 1H), 7.35 (m, 1H), 7.2-7.3 (m, 2H), 7.2 (m, 1H), 7.15

(t, 1H), 7.1 (d, 1H), 7.0 (s, 1H), 3.9 (s, 3H), 3.5 (m, 2H), 3.1-3.25 (s broad, 8H), 0.95 (t, 3H).

EXAMPLE 32

N-(3-Difluoromethoxy-phenyl)-4-methoxy-N-methyl-3-piperazin-1-yl-benzenesulfonamide hydrochloride

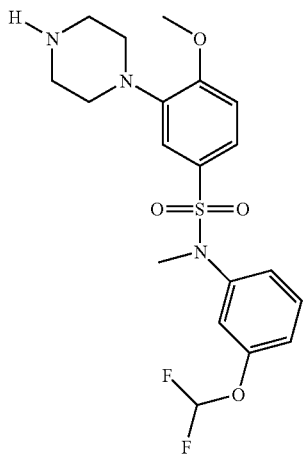

ESI-MS: 428.1 [M+H]+

1H-NMR (DMSO-d6, 400 Hz): δ [ppm] 9.6 (s broad, 2H), 9.0 (s, broad, 1H), 7.4 (m, 1H), 7.3 (t, 1H), 7.25 (m, 1H), 7.1-7.2 (m, 2H), 7.0 (d, 1H), 6.95 (s, 1H), 6.7 (s, 1H), 3.9 (s, 3H), 3.2 (s broad, 4H), 3.1 (s broad, 4H), 2.5 (m, 3H).

EXAMPLE 33

N-(3-Difluoromethoxy-4-methoxy-phenyl)-4-methoxy-3-piperazin-1-yl-N-propyl-benzenesulfonamide hydrochloride

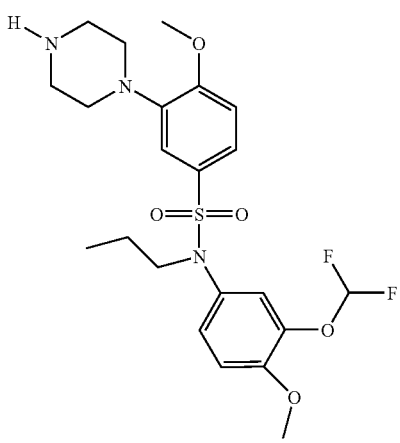

ESI-MS: 486.2 [M+H]+

1H-NMR (DMSO-d6, 400 Hz): δ [ppm] 9.3 (s broad, 2H), 7.25 (d, 1H), 7.15 (m, 2H), 7.0 (t, 1H), 6.95 (d, 1H), 6.85 (d, 1H), 6.75 (s, 1H), 3.9 (s, 3H), 3.8 (s, 3H), 3.4 (t, 2H), 3.2 (broad, 4H), 3.1 (broad, 4H), 1.8 (m, 2H), 0.8 (t, 3H).

EXAMPLE 34

N-(3-Difluoromethoxy-phenyl)-4-methoxy-3-piperazin-1-yl-N-propyl-benzenesulfonamide hydrochloride

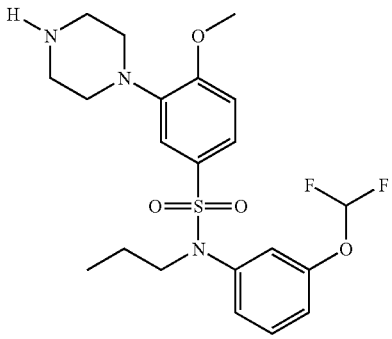

ESI-MS: 456.2 [M+H]+

1H-NMR (DMSO-d6, 400 Hz): δ [ppm] 9.55 (s broad, 2H), 7.4 (m, 1H), 7.25 (d, 2H), 7.15 (m, 2H), 6.95 (d, 1H), 6.85 (s, 1H), 6.8 (s, 1H), 3.85 (s, 3H), 3.45 (t, 2H), 3.2 (broad, 4H), 3.1 (broad, 4H), 1.8 (m, 2H), 0.8 (t, 3H).

EXAMPLE 35

N-(3-Difluoromethoxy-phenyl)-4-methoxy-3-(4-methyl-piperazin-1-yl)-benzenesulfonamide hydrochloride

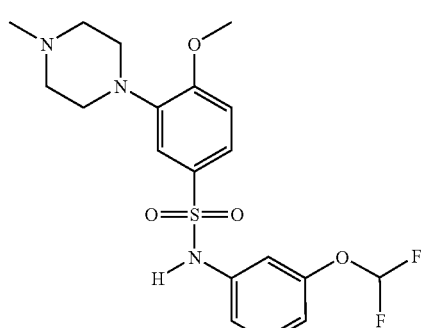

ESI-MS: 428.1 [M+H]+

1H-NMR (CDCl3, 400 Hz): δ [ppm] 7.45 (d, 1H), 7.2 (m, 2H), 6.8-7.0 (several m, 4H), 6.45 (t, 1H), 3.9 (s, 3H), 3.0 (s, 4H), 2.6 (s, 4H), 2.35 (s, 3H).

EXAMPLE 36

N-(2-Difluoromethoxy-phenyl)-4-methoxy-3-piperazin-1-yl-N-propyl-benzenesulfonamide hydrochloride

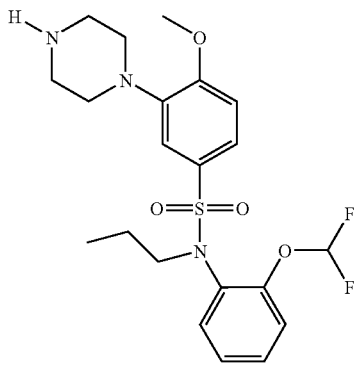

ESI-MS: 456.1 [M+H]$^+$
$^1$H-NMR (DMSO-d$_6$, 400 Hz): δ [ppm] 9.0 (broad, 2H), 7.45 (m, 1H), 7.35 (m, 1H), 6.9-7.3 (several m, 6H), 3.9 (s, 3H), 3.4 (t, 2H), 3.2 (broad, 4H), 3.15 (broad, 4H), 1.3 (m, 2H), 0.8 (t, 3H).

EXAMPLE 37

N-(2-Difluoromethoxy-phenyl)-4-methoxy-3-(4-methyl-piperazin-1-yl)-benzenesulfonamide hydrochloride

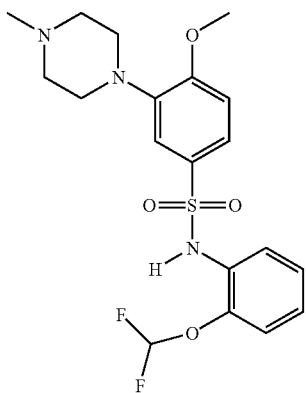

ESI-MS: 428.1 [M+H]$^+$
$^1$H-NMR (DMSO-d$_6$, 400 Hz): δ [ppm] 10.5 (s broad, 1H), 9.7 (s, 1H), 7.4 (d, 1H), 7.3 (m, 2H), 7.05-7.2 (several m, 4H), 6.95 (t, 1H), 3.85 (s, 3H), 3.45 (m, 4H), 3.2 (m, 2H), 2.95 (m, 2H), 2.8 (d, 3H).

EXAMPLE 38

N-(3-Difluoromethoxy-4-methoxy-phenyl)-4-methoxy-3-(4-methyl-piperazin-1-yl)-benzenesulfonamide hydrochloride

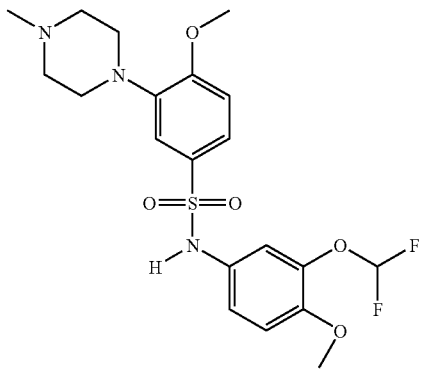

ESI-MS: 458.1 [M+H]$^+$
$^1$H-NMR (CDCl$_3$, 400 Hz): δ [ppm] 7.35 (m, 2H), 7.0 (m, 1H), 6.9 (s, 1H), 6.8 (m, 2H), 6.5 (t, 1H), 3.9 (s, 3H), 3.8 (s, 3H), 3.2 (broad, 4H), 2.8 (broad, 4H), 2.5 (s, broad, 3H).

EXAMPLE 39

N-(2-Difluoromethoxy-phenyl)-N-isopropyl-4-methyl-3-piperazin-1-yl-benzenesulfonamide hydrochloride

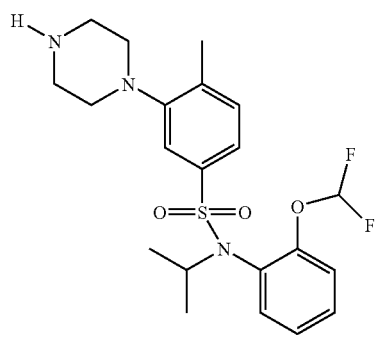

ESI-MS: 440.2 [M+H]$^+$
$^1$H-NMR (DMSO-d$_6$, 400 Hz): δ [ppm] 9.6 (s broad, 2H), 6.95-7.55 (several m, 8H), 4.3 (m, 1H), 3.2 (broad, 4H), 3.1 (broad, 4H), 2.3 (s, 3H), 1.0 (d, 3H), 0.9 (d, 3H).

EXAMPLE 40

N-(2,2-Difluoro-benzo[1,3]dioxol-4-yl)-4-methoxy-3-piperazin-1-yl-benzenesulfonamide hydrochloride

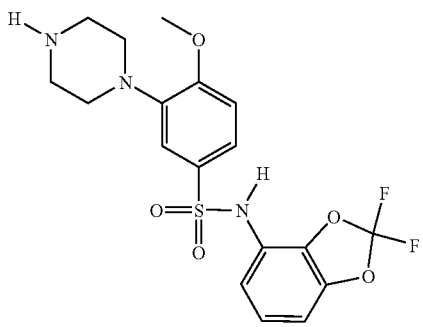

ESI-MS: 428.1 [M+H]+

¹H-NMR (DMSO-d₆, 400 Hz): δ [ppm] 10.4 (s, 1H), 9.6 (s broad, 2H), 7.35 (d, 1H), 7.25 (s, 1H), 7.2 (d, 1H), 7.1 (m, 2H), 6.9 (d, 1H), 3.85 (s, 3H), 3.2 (broad, 8H).

EXAMPLE 41

N-(2-Difluoromethoxy-phenyl)-3-piperazin-1-yl-benzenesulfonamide hydrochloride

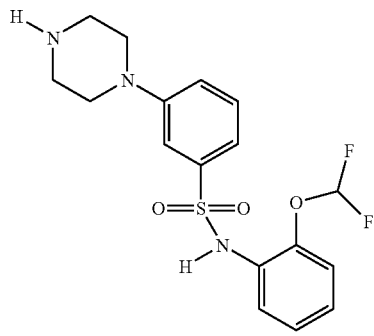

ESI-MS: 384.1 [M+H]+

¹H-NMR (DMSO-d₆, 400 Hz): δ [ppm] 9.9 (s, 1H), 9.75 (s broad, 2H), 7.4 (m, 2H), 7.25 (m, 2H), 7.1-7.2 (m, 4H), 6.95 (t, 1H), 3.4 (broad, 4H), 3.15 (broad, 4H),

EXAMPLE 42

N-(2-Difluoromethoxy-phenyl)-3-(4-methyl-piperazin-1-yl)-benzenesulfonamide hydrochloride

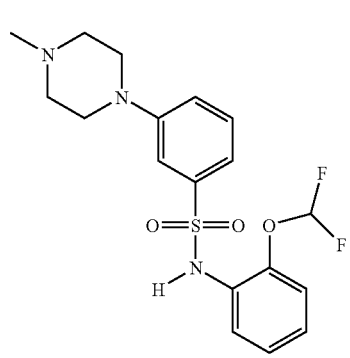

ESI-MS: 398.1 [M+H]+

¹H-NMR (DMSO-d₆, 400 Hz): δ [ppm] 11.45 (s broad, 1H), 9.9 (s broad, 1H), 7.35-7.45 (m, 2H), 7.25 (m, 2H), 7.1-7.2 (m, 4H), 7.0 (t, 1H), 3.0-3.9 (broad, 8H), 2.75 (s, 3H).

EXAMPLE 43

N-(2-Difluoromethoxy-phenyl)-N-methyl-3-piperazin-1-yl-benzenesulfonamide hydrochloride

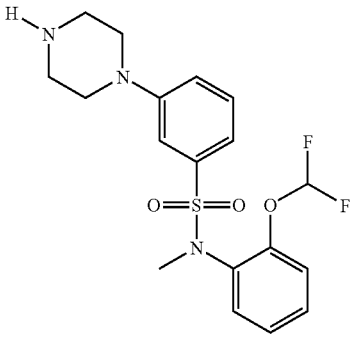

ESI-MS: 398.1 [M+H]+

¹H-NMR (DMSO-d₆, 400 Hz): δ [ppm] 9.5 (s broad, 2H), 7.5 (m, 1H), 7.45 (m, 1H), 7.3 (m, 1H), 7.2 (m, 2H), 7.1 (m, 3H), 7.05 (t, 1H), 3.4 (broad, 4H), 3.2 (broad, 4H), 3.1 (s, 3H).

EXAMPLE 44

N-(2-Difluoromethoxy-phenyl)-N-methyl-3-(4-methyl-piperazin-1-yl)-benzenesulfonamide hydrochloride

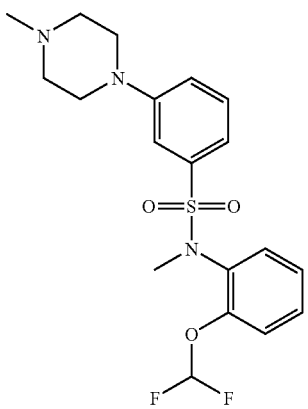

ESI-MS: 412.1 [M+H]+

¹H-NMR (DMSO-d₆, 400 Hz): δ [ppm] 11.5 (broad, 1H), 7.55 (m, 1H), 7.5 (m, 1H), 7.45 (d, 1H), 7.25 (m, 2H), 7.05-7.2 (several m, 4H), 3.4 (broad, 8H), 3.1 (s, 3H), 2.8 (s, 3H).

EXAMPLE 45

1-[3-(3-Difluoromethoxy-benzenesulfonyl)-phenyl]-piperazine hydrochloride

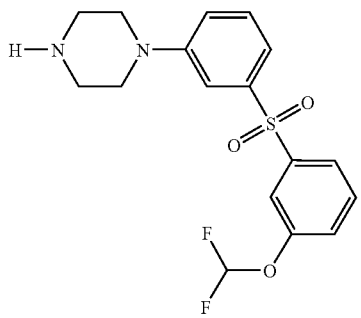

ESI-MS: 369.1 [M+H]+
$^1$H-NMR (DMSO-$d_6$, 400 Hz): δ [ppm] 9.6 (s broad, 2H), 7.85 (d, 1H), 7.75 (s, 1H), 7.7 (m, 1H), 7.45-7.55 (several m, 3H), 7.4 (t, 1H), 7.4 (d, 1H), 7.3 (m, 1H), 3.5 (s broad, 4H), 3.15 (s broad, 4H).

EXAMPLE 46

1-[3-(3-Difluoromethoxy-benzenesulfonyl)-phenyl]-4-methyl-piperazine hydrochloride

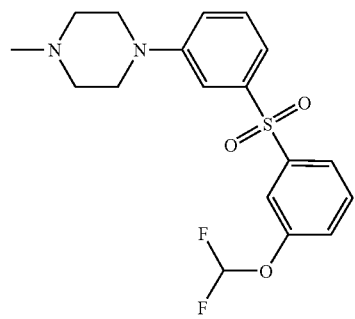

ESI-MS: 383.1 [M+H]+
$^1$H-NMR (DMSO-$d_6$, 400 Hz): δ [ppm] 7.85 (d, 1H), 7.8 (s, 1H), 7.7 (m, 1H), 7.45-7.55 (several m, 3H), 7.4 (d, 1H), 7.4 (t, 1H), 7.3 (d, 1H), 3.95 (d, 2H), 3.65 (d, 2H), 3.25 (m, 2H), 3.15 (m, 2H), 2.8 (d, 3H).

EXAMPLE 47

1-[5-(3-Difluoromethoxy-benzenesulfonyl)-2-methoxy-phenyl]-piperazine hydrochloride

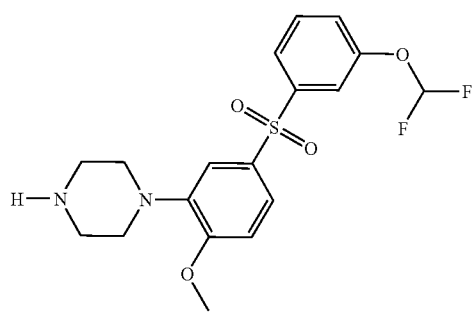

ESI-MS: 399.1 [M+H]+
$^1$H-NMR (DMSO-$d_6$, 400 Hz): δ [ppm] 9.5 (s broad, 2H), 7.8 (d, 1H), 7.7 (s, 1H), 7.65 (m, 2H), 7.45 (d, 1H), 7.4 (t, 1H), 7.4 (m, 1H), 7.2 (d, 1H), 3.85 (s, 3H), 3.25 (s broad, 4H), 3.2 (s broad, 4H).

EXAMPLE 48

1-[5-(3-Difluoromethoxy-benzenesulfonyl)-2-methoxy-phenyl]-4-methyl-piperazine hydrochloride

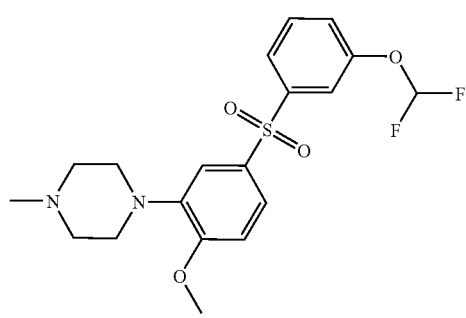

ESI-MS: 413.1 [M+H]+
$^1$H-NMR (DMSO-$d_6$, 400 Hz): δ [ppm] 7.8 (d, 1H), 7.75 (s, 1H), 7.65 (m, 2H), 7.5 (d, 1H), 7.4 (t, 1H), 7.4 (s, 1H), 7.2 (d, 1H), 3.85 (s, 3H), 3.55 (m, 2H), 3.45 (m, 2H), 3.05-3.2 (m, 4H), 2.8 (s, 3H).

EXAMPLE 49

1-[5-(3-Difluoromethoxy-4-methoxy-benzenesulfonyl)-2-methoxy-phenyl]-piperazine hydrochloride

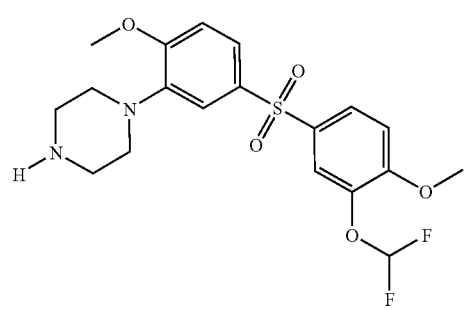

ESI-MS: 429.2 [M+H]+
$^1$H-NMR (DMSO-$d_6$, 400 Hz): δ [ppm] 9.55 (s broad, 2H), 7.85 (d, 1H), 7.7 (s, 1H), 7.6 (d, 1H), 7.3 (m, 2H), 7.2 (t, 1H), 7.17 (d, 1H), 3.9 (s, 3H), 3.85 (s, 3H), 3.25 (s broad, 4H), 3.2 (s broad, 4H).

EXAMPLE 50

N-(2-Difluoromethoxy-5-methyl-phenyl)-4-ethoxy-3-piperazin-1-yl-benzenesulfonamide hydrochloride

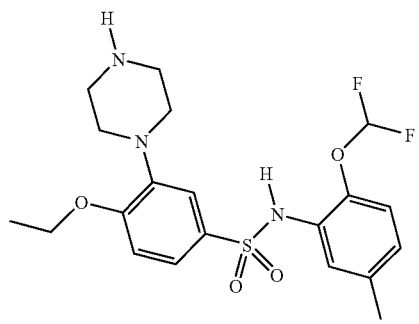

ESI-MS: 442,1 [M+H]+
1H-NMR (DMSO-d6, 400 Hz): δ [ppm] 9.7 (broad, 1H), 9.0 (broad, 2H), 7.35 (d, 1H), 7.27 (s, 1H), 7.1 (s, 1H), 7.05 (d, 1H), 6.95 (m, 2H), 6.85 (t, 1H), 4.1 (q, 2H), 3.2 (broad, 4H), 3.15 (broad, 4H), 2.2 (s, 3H), 1.35 (t, 3H).

EXAMPLE 51

N-(3,4-Bis-difluoromethoxy-phenyl)-4-methoxy-3-(4-methyl-piperazin-1-yl)-benzenesulfonamide hydrochloride

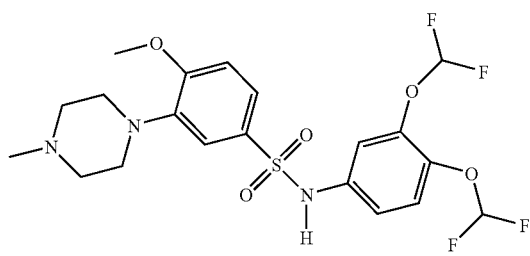

ESI-MS: 494 [M+H]+

EXAMPLE 52

N-(3,4-Bis-difluoromethoxy-phenyl)-4-methyl-3-piperazin-1-yl-benzenesulfonamide hydrochloride

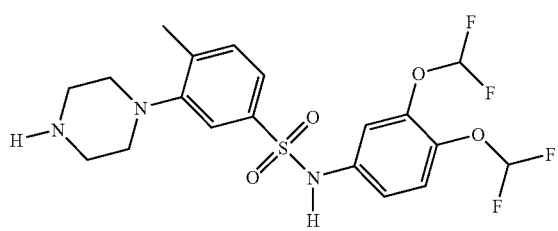

ESI-MS: 464.1 [M+H]+
1H-NMR (DMSO-d6, 400 Hz): δ [ppm] 10.6 (broad, 1H), 9,6 (broad, 2H), 7.3-7.45 (m, 3H), 6.9-7.3 (several m, 5H), 3.2 (broad, 4H), 3.05 (broad, 2H), 2.3.

EXAMPLE 53

N-(5-Chloro-2-difluoromethoxy-phenyl)-4-methoxy-3-(4-methyl-piperazin-1-yl)-benzenesulfonamide hydrochloride

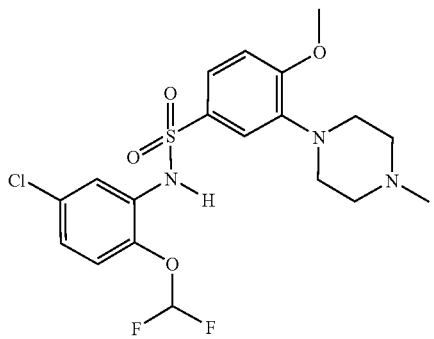

ESI-MS: 462 [M+H]+
1H-NMR (DMSO-d6, 400 Hz): δ [ppm] 10.5 (broad, 1H), 10.05 (broad, 1H), 7.4 (d, 1H), 7.35 (s, 1H), 7.32 (s, 1H), 7.23 (d, 1H), 7.18 (d, 1H), 7.1 (d, 1H), 7.0 (t, 1H), 3.85 (s, 3H), 3.5 (broad, 4H), 3.2 (broad, 2H), 3.0 (broad, 2H), 2.8 (s, 3H).

EXAMPLE 54

N-(2-Difluoromethoxy-5-methyl-phenyl)-4-ethyl-3-(4-methyl-piperazin-1-yl)-benzenesulfonamide

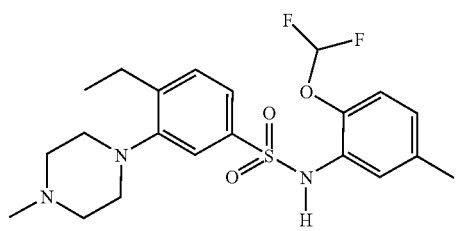

ESI-MS: 440.1 [M+H]+

EXAMPLE 55

N-(5-Difluoromethoxy-2-methyl-phenyl)-4-methoxy-3-(4-methyl-piperazin-1-yl)-benzenesulfonamide hydrochloride

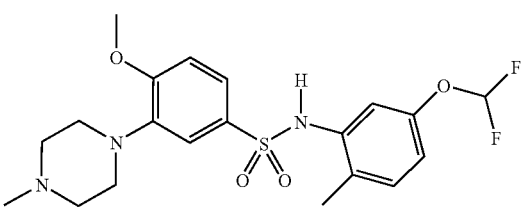

ESI-MS: 442.1 [M+H]+
1H-NMR (DMSO-d6, 400 Hz): δ [ppm] 10.6 (broad, 1H ), 9.6 (broad, 1H ), 7.35 (d, 1H), 7.05-7.25 (several m, 4H), 6.9 (d, 1H ), 6.8 (s, 1H ), 3.85 (s, 3H), 3.1-3.7 (broad, 8H), 3.4 (s, 3H), 2.0 (s, 3H).

EXAMPLE 56

N-(5-Chloro-2-difluoromethoxy-phenyl)-4-methyl-3-(4-methyl-piperazin-1-yl)-benzenesulfonamide hydrochloride

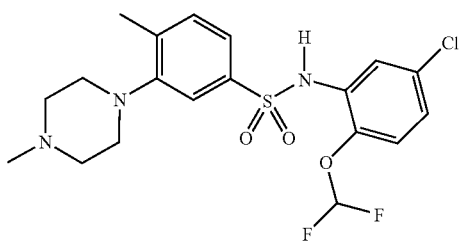

ESI-MS: 446.1 [M+H]+
$^1$H-NMR (DMSO-d$_6$, 400 Hz): δ [ppm] 10.4 (very broad, 2H), 7.48 (s, 1H), 7.4 (m, 2H), 7.33 (s, 1H), 7.23 (d, 1H), 7.18 (d, 1H), 6.98 (t, 1H), 2.95-3.7 (broad, 8H), 2.9 (s, 3H), 2.3 (s, 3H).

EXAMPLE 57

N-(5-Chloro-2-difluoromethoxy-phenyl)-4-methoxy-3-piperazin-1-yl-benzenesulfonamide hydrochloride

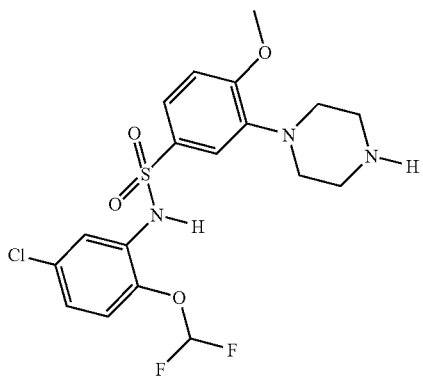

ESI-MS: 448.1 [M+H]+
$^1$H-NMR (DMSO-d$_6$, 400 Hz): δ [ppm] 10.05 (s, 1H), 9.1 (broad, 2H), 7.4 (d, 1H), 7.32 (m, 2H), 7.22 (d, 1H), 7.17 (d, 1H), 7.10 (d, 1H), 7.0 (t, 1H), 3.85 (s, 3H), 3.2 (broad, 4H), 3.15 (broad, 4H).

EXAMPLE 58

N-(5-Difluoromethoxy-2-methyl-phenyl)-4-methyl-3-piperazin-1-yl-benzenesulfonamide hydrochloride

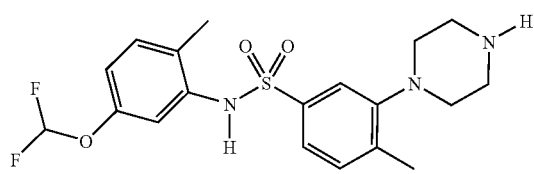

ESI-MS: 412.1 [M+H]+
$^1$H-NMR (DMSO-d$_6$, 400 Hz): δ [ppm] 7.2-7.4 (several m, 3H), 7.15 (d, 1H), 7.1 (t, 1H), 6.88 (d, 1H), 6.82 (s, 1H), 3.1 (broad, 4H), 2.9 (broad, 4H), 2.3 (s, 3H), 1.95 (s, 3H).

EXAMPLE 59

N-(5-Difluoromethoxy-2-methyl-phenyl)-4-methoxy-3-piperazin-1-yl-benzenesulfonamide hydrochloride

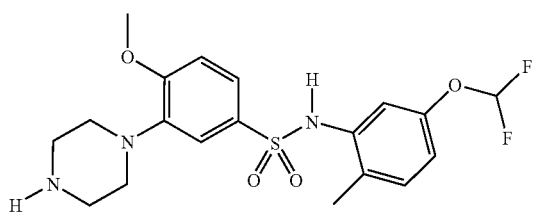

ESI-MS: 428.1 [M+H]+
$^1$H-NMR (DMSO-d$_6$, 400 Hz): δ [ppm] 9.65-9.8 (broad, 3H), 7.3 (d, 1H), 7.2 (s, 1H), 7.18 (d, 1H), 7.12 (t, 1H), 7.1 (d, 1H), 6.9 (d, 1H), 6.75 (s, 1H), 3.8 (s, 3H), 3.15 (broad, 8H), 1.95 (s, 3H).

EXAMPLE 60

N-(3,4-Bis-difluoromethoxy-phenyl)-4-methoxy-3-piperazin-1-yl-benzenesulfonamide hydrochloride

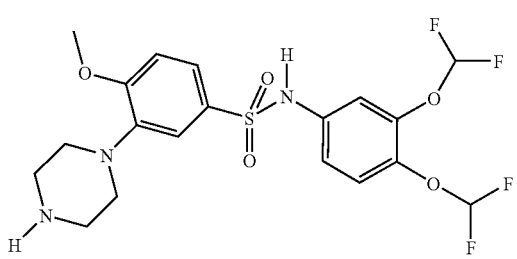

ESI-MS: 480.1 [M+H]+
$^1$H-NMR (DMSO-d$_6$, 400 Hz): δ [ppm] 10.55 (s, 1H), 9.5 (s, 2H), 7.43 (d, 1H), 7.25 (m, 2H), 6.9-7.15 (m, 5H), 3.9 (s, 3H), 3.2 (broad, 8H).

EXAMPLE 61

N-(5-Chloro-2-difluoromethoxy-phenyl)-4-ethyl-3-piperazin-1-yl-benzenesulfonamide hydrochloride

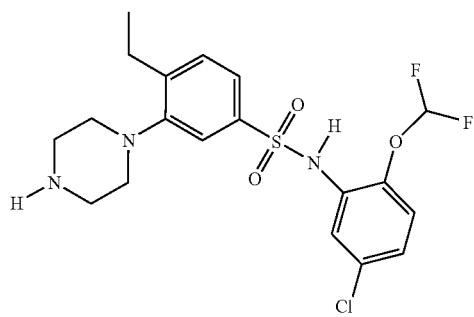

ESI-MS: 446 [M+H]+
$^1$H-NMR (DMSO-d$_6$, 400 Hz): δ [ppm] 10.25 (broad, 1H), 9.55 (broad, 2H), 7.5 (s, 1H), 7.4 (m, 2H), 7.3 (s, 1H), 7.25 (d, 1H), 7.2 (d, 1H), 7.0 (t, 1H), 3.25 (broad, 4H), 3.05 (broad, 4H), 2.7 (q, 2H), 1.2 (t, 3H).

EXAMPLE 62

N-(2-Difluoromethoxy-4-methyl-phenyl)-4-ethyl-3-piperazin-1-yl-benzenesulfonamide hydrochloride

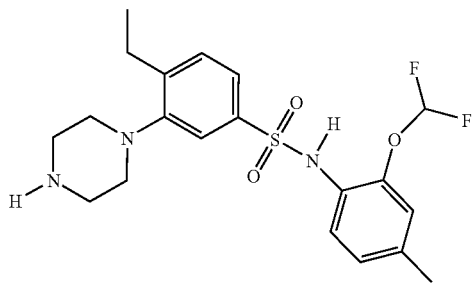

ESI-MS: 426.1 [M+H]+
$^1$H-NMR (DMSO-d$_6$, 400 Hz): δ [ppm] 9.5 (broad, 2H), 7.3-7.4 (m, 3H), 7.1 (d, 1H), 6.97 (d, 1H), 6.93 (s, 1H), 6.9 (t, 1H), 3.2 (broad, 4H), 3.0 (broad, 4H), 2.68 (q, 2H), 2.25 (s, 3H), 1.18 (t, 3H).

EXAMPLE 63

N-(2-Difluoromethoxy-5-methyl-phenyl)-4-methyl-3-((R)-3-methyl-piperazin-1-yl)-benzenesulfonamide hydrochloride

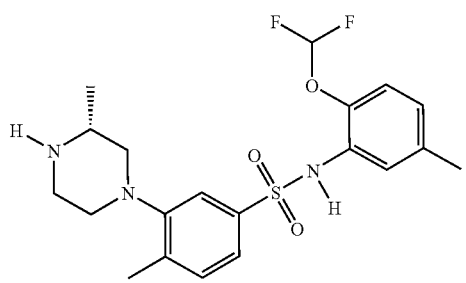

ESI-MS: 426.2 [M+H]+
$^1$H-NMR (methanol-d$_4$, 400 Hz): δ [ppm] 7.3-7.45 (m, 4H), 6.9-7.05 (m, 2H), 6.4 (t, 1H), 2.7-3.7 (several m, 7H), 2.4 (s, 3H), 2.3 (s, 3H), 1.4 (d, 3H).

EXAMPLE 64

N-(2-Difluoromethoxy-5-methyl-phenyl)-4-methyl-3-((S)-3-methyl-piperazin-1-yl)-benzenesulfonamide hydrochloride

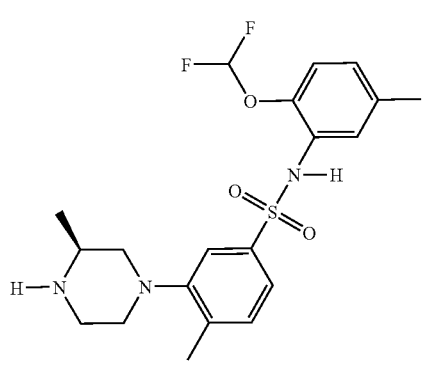

ESI-MS: 426.2 [M+H]+
$^1$H-NMR (DMSO-d$_6$, 400 Hz): δ [ppm] 9.85 (s, 1H), 9.65 (broad, 1H), 9.4 (broad, 1H), 7.4 (s, 1H), 7.35 (s, 2H), 7.1 (s, 1H), 6.95-7.0 (m, 2H), 7.0 (t, 1H), 3.4 (broad, 3H), 3.1 (m, 2H), 2.95 (m, 1H), 2.8 (m, 1H), 2.3 (s, 3H), 2.22 (s, 3H), 1.3 (d, 3H).

EXAMPLE 65

N-(2-Difluoromethoxy-5-methyl-phenyl)-4-ethyl-3-piperazin-1-yl-benzenesulfonamide hydrochloride

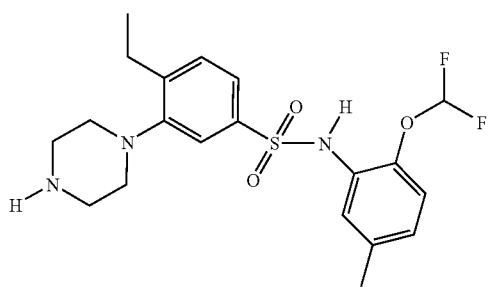

ESI-MS: 426.1 [M+H]+
$^1$H-NMR (DMSO-d$_6$, 400 Hz): δ [ppm] 9.85 (broad, 1H), 9.6 (broad, 2H), 7.45 (s, 1H), 7.4 (m, 2H), 7.1 (s, 1H), 6.95-7.0 (m, 2H), 6.85 (t, 1H), 3.22 (broad, 4H), 3.02 (broad, 4H), 2.68 (q, 2H), 2.2 (s, 3H), 1.15 (t, 3H).

EXAMPLE 66

N-(2,2-Difluoro-benzo[1,3]dioxol-5-yl)-4-methoxy-3-(4-methyl-piperazin-1-yl)-benzenesulfonamide hydrochloride

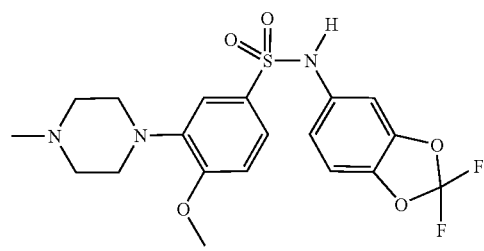

ESI-MS: 442.1 [M+H]+
$^1$H-NMR (DMSO-d$_6$, 400 Hz): δ [ppm] 10.1 (broad, 1H), 7.33 (d, 1H), 7.28 (d, 1H), 7.08-7.15 (m, 2H), 7.05 (d, 1H), 6.8 (d, 1H), 3.8 (s, 3H), 2.9 (broad, 4H), 2.45 (broad, 4H), 2.2 (s, 3H).

EXAMPLE 67

N-(2-Difluoromethoxy-5-methyl-phenyl)-4-methoxy-3-(4-methyl-piperazin-1-yl)-benzenesulfonamide hydrochloride

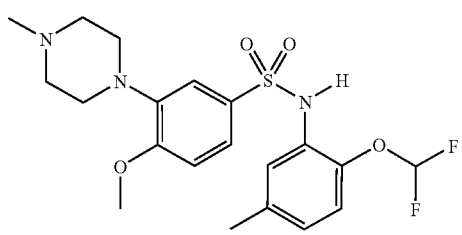

0.429 g N-(2-(difluoromethoxy)-5-methylphenyl)-4-methoxy-3-(piperazin-1-yl)benzenesulfonamide (1.004 mmol) were dissolved in 5 mL of dichloromethane. 0.086 mL of acetic acid (1.505 mmol) and 0.319 g of sodium triacetoxyborohydride (3.01 mmol) were added. After stirring for 10 min, 0.083 mL of aqueous formaldehyde solution (3.01 mmol) were added and the reaction stirred for 72 h at room temperature. The solvents were evaporated and the residue purified via preparative silica gel chromatography (Super Flash cartridge (Interchim)) using a dichloromethane (+0.1% triethylamine) and methanol gradient as eluent. Fractions containing the product were combined, the solvents evaporated, and the product converted to the hydrochloride salt by addition of hydrochloric acid in diethyl ether and subsequent evaporation to dryness (yield 0.169 g of product).

ESI-MS: 442.1 [M+H]$^+$ $^1$H-NMR (DMSO-d$_6$, 400 Hz): δ [ppm] 9.6 (broad, 1H), 7.3 (d, 1H), 7.2 (s, 1H), 7.1 (s, 1H), 6.9-7.05 (several m, 3H), 6.8 (t, 1H), 3.8 (s, 3H), 2.9 (broad, 4H), 2.45 (broad, 4H), 2.2 (two s, 6H).

EXAMPLE 68

N-(3-Difluoromethoxy-phenyl)-3-piperazin-1-yl-benzenesulfonamide hydrochloride

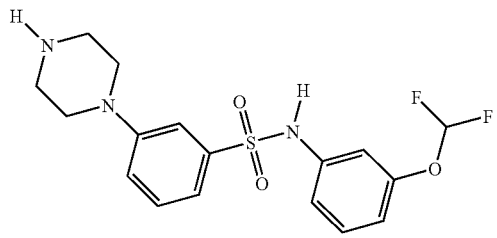

ESI-MS: 384.1 [M+H]$^+$ $^1$H-NMR (DMSO-d$_6$, 400 Hz): δ [ppm] 10.6 (s, 1H), 9.85 (broad, 1H), 9.45 (broad, 2H), 7.4 (m, 2H), 7.2-7.35 (m, 3H), 7.2 (t, 1H), 7.0 (m, 1H), 6.95 (s, 1H), 6.85 (d, 1H), 3.15-3.65 (broad, 8H).

EXAMPLE 69

N-(2-Difluoromethoxy-4-fluoro-phenyl)-4-methoxy-3-(4-methyl-piperazin-1-yl)-benzenesulfonamide hydrochloride

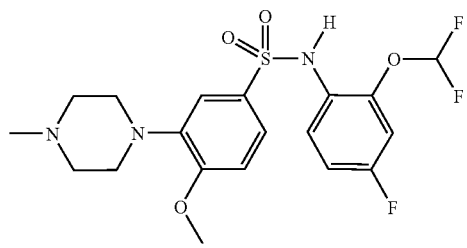

ESI-MS: 446.1 [M+H]$^+$ $^1$H-NMR (DMSO-d$_6$, 400 Hz): δ [ppm] 10.85 (broad, 1H), 9.75 (s, 1H), 7.2-7.35 (m, 3H), 7.0-7.1 (m, 3H), 7.07 (t, 1H), 3.85 (s, 3H), 3.5 (m, 4H), 3.18 (m, 2H), 3.02 (m, 2H), 2.85 (s, 3H).

EXAMPLE 70

N-(2-Difluoromethoxy-4-methyl-phenyl)-4-methoxy-3-(4-methyl-piperazin-1-yl)-benzenesulfonamide hydrochloride

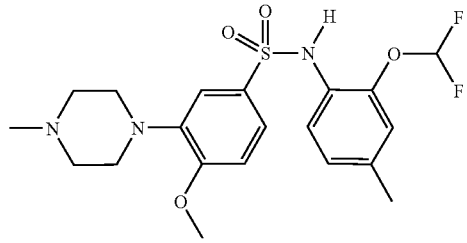

ESI-MS: 442.1 [M+H]$^+$ $^1$H-NMR (DMSO-d$_6$, 400 Hz): δ [ppm] 11.2 (broad, 1H), 9.6 (s, 1H), 7.3 (m, 2H), 7.12 (d, 1H), 7.05 (d, 1H), 6.9-7.0 (several m, 2H), 6.92 (t, 1H), 3.8 (s, 3H), 3.45 (m, 4H), 3.17 (m, 2H), 3.05 (m, 2H), 2.8 (s, 3H), 2.25 (s, 3H).

EXAMPLE 71

N-(5-Chloro-2-difluoromethoxy-phenyl)-4-methyl-3-piperazin-1-yl-benzenesulfonamide hydrochloride

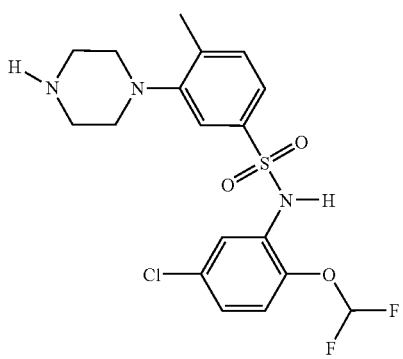

ESI-MS: 432.1 [M+H]+

¹H-NMR (DMSO-d₆, 400 Hz): δ [ppm] 10.3 (s, 1H), 9.75 (broad, 2H), 7.15-7.5 (several m, 6H), 7.05 (t, 1H), 3.2 (broad, 4H), 3.07 (broad, 4H), 2.3 (s, 3H).

EXAMPLE 72

N-(2-Difluoromethoxy-5-methyl-phenyl)-4-methoxy-3-piperazin-1-yl-enzenesulfonamide hydrochloride

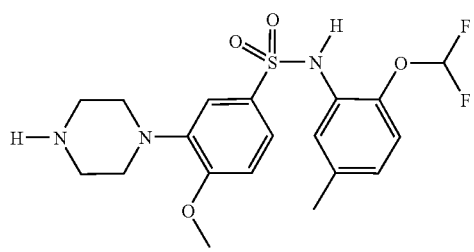

ESI-MS: 428.1 [M+H]+

¹H-NMR (DMSO-d₆, 400 Hz): δ [ppm] 463,9306 1H-NMR (DMSO-d6, 400 Hz): d [ppm] 9.7 (broad, 1H), 9.6 (broad, 2H), 7.35 (d, 1H), 7.3 (s, 1H), 7.1 (s, 1H), 7.05 (d, 1H), 6.9-7.0 (m, 2H), 6.85 (t, 1H), 3.8 (s, 3H), 3.1-3.25 (broad, 8H) 2.2 (s, 3H).

EXAMPLE 73

N-(2-Difluoromethoxy-4-methyl-phenyl)-4-methoxy-3-piperazin-1-yl-benzenesulfonamide hydrochloride

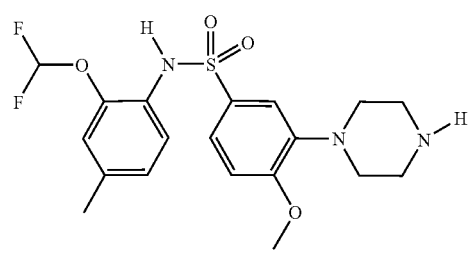

ESI-MS: 428.1 [M+H]+

¹H-NMR (DMSO-d₆, 400 Hz): δ [ppm] 7.3 (d, 1H), 7.2 (s, 1H), 7.15 (d, 1H), 6.95 (d, 1H), 6.9 (d, 1H), 6.85 (t, 1H), 3.8 (s, 3H), 2.8-2.95 (broad, 8H) 2.2 (s, 3H).

EXAMPLE 74

N-(2-Difluoromethoxy-4-fluoro-phenyl)-4-methyl-3-piperazin-1-yl-benzenesulfonamide hydrochloride

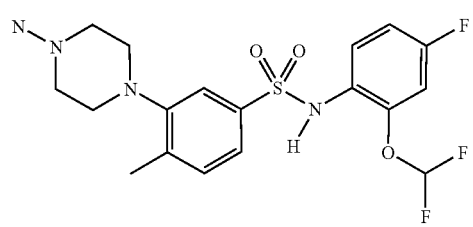

ESI-MS: 416.1 [M+H]+

¹H-NMR (DMSO-d₆, 400 Hz): δ [ppm] 7.15-7.35 (several m, 4H), 7.1 (t, 1H), 6.8-6.95 (m, 2H), 3.0 (broad, 4H), 2.85 (broad, 4H), 2.2 (s, 3H).

EXAMPLE 75

N-(3-Difluoromethoxy-4-methyl-phenyl)-4-methyl-3-(4-methyl-piperazin-1-yl)-benzenesulfonamide hydrochloride

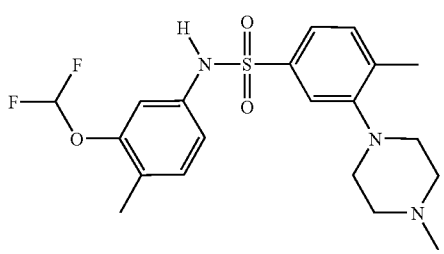

ESI-MS: 426.1 [M+H]+

¹H-NMR (DMSO-d₆, 400 Hz): δ [ppm] 11.35 (broad, 1H), 10.4 (s, 1H), 7.4 (s, 1H), 7.35 (m, 2H), 7.15 (d, 1H), 7.1 (t, 1H), 7.0 (s, 1H), 6.9 (m, 1H), 3.5 (broad, 2H), 3.2 (broad, 2H), 3.1 (broad, 4H), 2.8 (s, 3H), 2.3 (s, 3H), 2.1 (s, 3H).

EXAMPLE 76

N-(4-Difluoromethoxy-3-methoxy-phenyl)-4-methyl-3-piperazin-1-yl-benzenesulfonamide

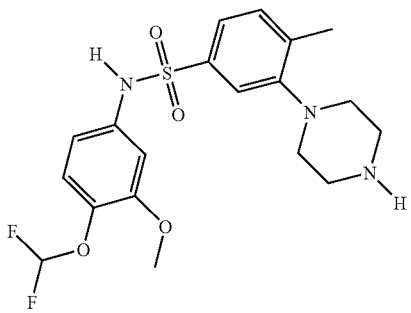

ESI-MS: 428.1 [M+H]+

¹H-NMR (DMSO-d₆, 400 Hz): δ [ppm] 9.4 (broad, 1H), 7.4 (m, 1H), 7.37 (m, 2H), 7.03 (d, 1H), 6.9 (t, 1H), 6.87 (s, 1H), 6.65 (d, 1H), 3.7 (s, 3H), 3.25 (broad, 4H), 3.0 (broad, 4H), 2.25 (s, 3H).

EXAMPLE 77

N-(5-Difluoromethoxy-2-methoxy-phenyl)-4-methyl-3-(4-methyl-piperazin-1-yl)-benzenesulfonamide trifluoroacetate

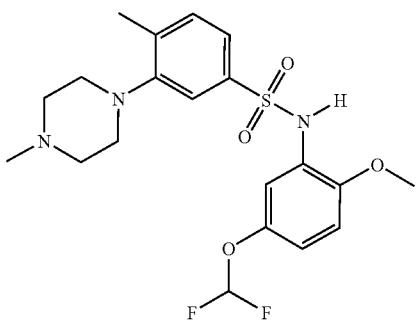

ESI-MS: 442.1 [M+H]+

$^1$H-NMR (DMSO-d$_6$, 400 Hz): δ [ppm] 9.6 (s, 1H), 7.3-7.45 (m, 3H), 7.07 (d, 1H), 7.05 (t, 1H), 6.95 (m, 2H), 3.55 (s, 3H), 3.55 (broad, 2H), 3.2 (broad, 4H), 2.9 (broad, 2H), 2.9 (s, 3H), 2.3 (s, 3H).

EXAMPLE 78

N-(2-Difluoromethoxy-5-methoxy-phenyl)-4-methyl-3-(4-methyl-piperazin-1-yl)-benzenesulfonamide trifluoroacetate

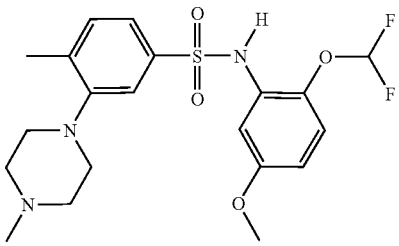

ESI-MS: 442.1 [M+H]+

$^1$H-NMR (CDCl$_3$, 400 Hz): δ [ppm] 7.5 (d, 1H), 7.37 (s, 1H), 7.2 (d, 1H), 6.93 (m, 2H), 6.6 (d, 1H), 6.2 (t, 1H), 3.8 (s, 3H), 3.67 (m, 2H), 3.2 (m, 2H), 3.1 (m, 2H), 3.0 (m, 2H), 2.9 (s, 3H), 2.3 (s, 3H).

EXAMPLE 79

N-(2-Difluoromethoxy-4-fluoro-phenyl)-4-methyl-3-(4-methyl-piperazin-1-yl)-benzenesulfonamide trifluoroacetate

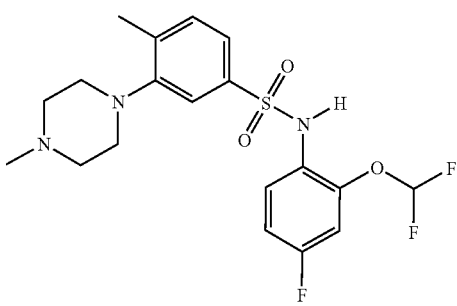

ESI-MS: 430.1 [M+H]+

$^1$H-NMR (CDCl$_3$, 400 Hz): δ [ppm] 7.63 (m, 1H), 7.38 (m, 2H), 6.95 (m, 1H), 6.85 (s, 1H), 6.78 (d, 1H), 6.27 (t, 1H), 3.7 (m, 2H), 3.25 (m, 2H), 2.95-3.2 (broad, 4H), 2.9 (s, 3H), 2.3 (s, 3H).

EXAMPLE 80

N-(5-Difluoromethoxy-2-methoxy-phenyl)-4-methyl-3-piperazin-1-yl-benzenesulfonamide trifluoroacetate

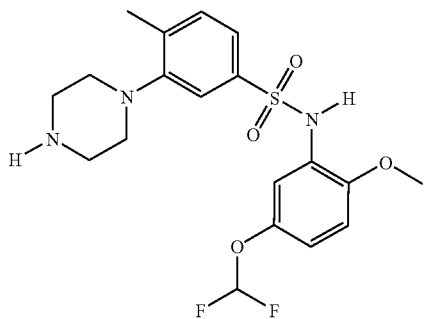

ESI-MS: 428.1 [M+H]+

$^1$H-NMR (CDCl$_3$, 400 Hz): δ [ppm] 9.8 (broad, 2H), 7.52 (d, 1H), 7.38 (s, 2H), 7.1 (s, 1H), 6.8 (m, 1H), 6.7 (m, 1H), 6.45 (t, 1H), 3.7 (s, 3H), 3.35 (broad, 4H), 3.1 (broad, 4H), 2.3 (s, 3H).

EXAMPLE 81

N-(2-Difluoromethoxy-5-methoxy-phenyl)-4-methyl-3-piperazin-1-yl-benzenesulfonamide hydrochloride

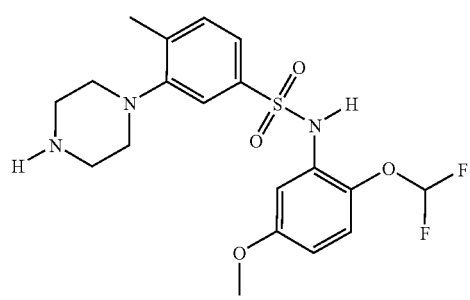

ESI-MS: 428.1 [M+H]+

$^1$H-NMR (DMSO-d$_6$, 400 Hz): δ [ppm] 9.7 (broad, 2H), 7.45 (s, 1H), 7.35 (m, 2H), 7.05 (d, 1H), 6.8 (d, 1H), 6.8 (t, 1H), 6.7 (d, 1H), 3.65 (s, 3H), 3.2 (broad, 4H), 3.05 (broad, 4H), 2.3 (s, 3H).

EXAMPLE 82

N-(2-Difluoromethoxy-4-fluoro-phenyl)-4-methoxy-3-piperazin-1-yl-benzenesulfonamide hydrochloride

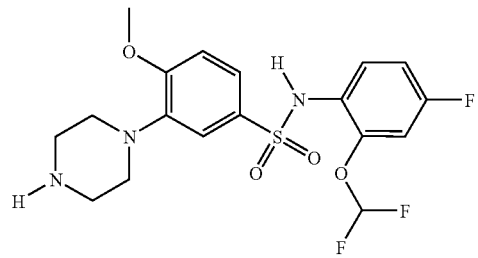

ESI-MS: 432.1 [M+H]+
1H-NMR (DMSO-d6, 400 Hz): δ [ppm] 7.15-7.35 (several m, 3H), 6.9-7.05 (several m, 3H), 6.85-7.15 (t, 1H), 3.8 (s, 3H), 3.05 (m, 4H), 3.0 (m, 4H).

EXAMPLE 83

N-(2,2-Difluoro-benzo[1,3]dioxol-5-yl)-4-methoxy-3-piperazin-1-yl-benzenesulfonamide hydrochloride

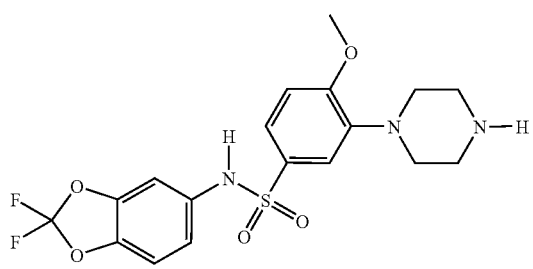

ESI-MS: 428.1 [M+H]+
1H-NMR (DMSO-d6, 400 Hz): δ [ppm] 7.35 (d, 1H), 7.15-7.2 (m, 2H), 7.05 (s, 1H), 7.0 (d, 1H), 6.85 (d, 1H), 3.8 (s, 3H), 2.85-3.0 (broad, 8H).

EXAMPLE 84

N-(2,2-Difluoro-benzo[1,3]dioxol-5-yl)-4-methyl-3-piperazin-1-yl-benzenesulfonamide hydrochloride

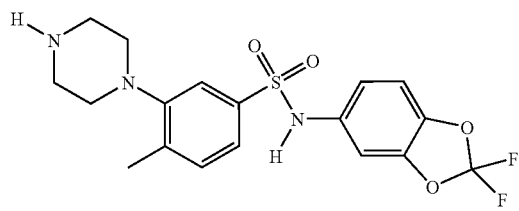

ESI-MS: 412,1 [M+H]+
1H-NMR (DMSO-d6, 400 Hz): δ [ppm] 10.4 (s, 1H), 9.25 (broad, 2H), 7.4 (s, 1H), 7.35 (m, 2H), 7.28 (d, 1H), 7.15 (m, 1H), 6.88 (d, 1H), 3.25 (broad, 4H), 3.05 (broad, 4H), 2.3 (s, 3H).

EXAMPLE 85

N-(3-Difluoromethoxy-4-methoxy-phenyl)-4-methyl-3-piperazin-1-yl-benzenesulfonamide hydrochloride

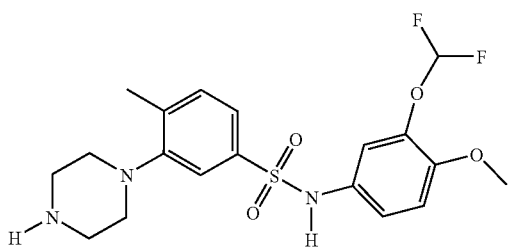

ESI-MS: 428.2 [M+H]+
1H-NMR (DMSO-d6, 400 Hz): δ [ppm] 8.8-10.4 (very broad, 3H), 7.3-7.4 (m, 3H), 7.03 (d, 1H), 6.95 (t, 1H), 6.85-7.0 (m, 2H), 3.75 (s, 3H), 3.2 (broad, 4H), 3.05 (broad, 4H), 2.25 (s, 3H).

EXAMPLE 86

N-(3-Difluoromethoxy-4-methyoxy-phenyl)-4-methyl-3-(4-methyl-piperazin-1-yl)-benzenesulfonamide hydrochloride

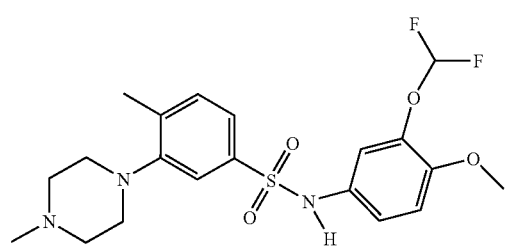

ESI-MS: 443.2 [M+H]+
1H-NMR (DMSO-d6, 400 Hz): δ [ppm] 11.3 (very broad, 1H), 10.15 (s, 1H), 7.4 (s, 1H), 7.3 (m, 2H), 7.05 (d, 1H), 6.95 (m, 2H), 6.95 (t, 1H), 3.7 (s, 3H), 3.05-3.5 (broad, 8H), 2.8 (s, 3H), 2.25 (s, 3H).

EXAMPLE 87

N-(4-Difluoromethoxy-3-methyl-phenyl)-4-methyl-3-(4-methyl-piperazin-1-yl)-benzenesulfonamide hydrochloride

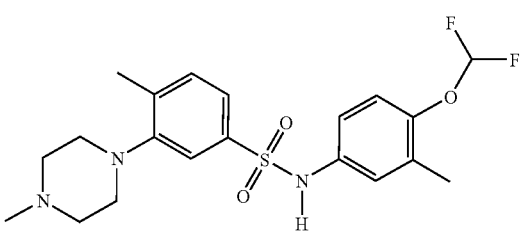

ESI-MS: 427.1 [M+H]+

¹H-NMR (DMSO-d₆, 400 Hz): δ [ppm] 10.3 (s broad, 1H), 7.3-7.4 (m, 3H), 7.15 (d, 1H), 7.0 (t, 1H), 6.95 (s, 1H), 6.88 (m, 1H), 3.4 (broad, 4H), 3.1 (broad, 4H), 2.8 (s, 3H), 2.25 (s, 3H), 2.1 (s, 3H).

EXAMPLE 88

N-(4-Difluoromethoxy-phenyl)-4-methyl-3-(4-methyl-piperazin-1-yl)-benzenesulfonamide hydrochloride

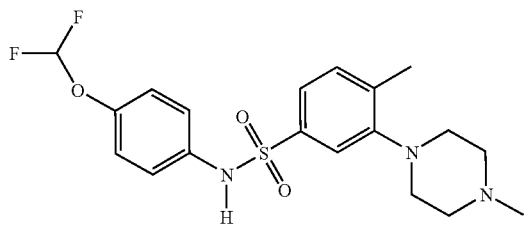

ESI-MS: 413.2 [M+H]+

¹H-NMR (DMSO-d₆, 400 Hz): δ [ppm] 10.25 (s broad, 1H), 7.3-7.4 (m, 3H), 7.1 (dd, 2H), 7.05 (dd, 2H), 7.05 (t, 1H), 3.4 (broad, 4H), 3.1 (broad, 4H), 2.75 (s, 3H), 2.3 (s, 3H).

EXAMPLE 89

N-(3-Difluoromethoxy-4-methyl-phenyl)-4-methoxy-3-(4-methyl-piperazin-1-yl)-benzenesulfonamide hydrochloride

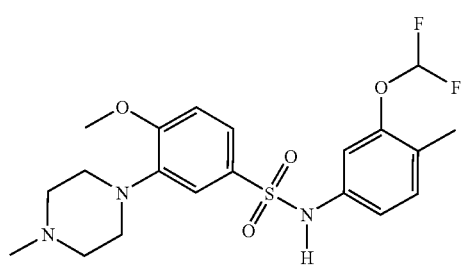

ESI-MS: 442.2 [M+H]+

¹H-NMR (DMSO-d₆, 400 Hz): δ [ppm] 10.2 (s broad, 1H), 7.4 (d, 1H), 7.3 (s, 2H), 7.15 (d, 1H), 7.08 (m, 1H), 7.03 (t, 1H), 6.95 (s, 1H), 6.9 (d, 1H), 3.8 (s, 3H), 3.0-3.6 (broad, 8H), 2.8 (s, 3H), 2.1 (s, 3H).

EXAMPLE 90

N-(4-Difluoromethoxy-3-methoxy-phenyl)-4-methoxy-3-(4-methyl-piperazin-1-yl)-benzenesulfonamide

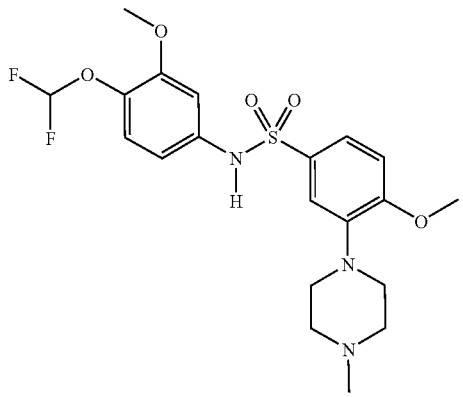

ESI-MS: 458.1 [M+H]+

¹H-NMR (DMSO-d₆, 400 Hz): δ [ppm] 7.42 (d, 1H), 7.27 (s, 1H), 7.05 (m, 2H), 6.9 (d, 1H), 6.9 (t, 1H), 6.7 (d, 1H), 3.8 (s, 3H), 3.7 (s, 3H), 3.1 (broad, 4H), 2.9 (broad, 4H), 2.5 (s, 3H).

EXAMPLE 91

N-(2-Difluoromethoxy-4-methyl-phenyl)-4-methyl-3-(4-methyl-piperazin-1-yl)-benzenesulfonamide hydrochloride

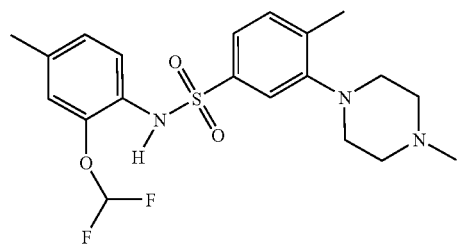

ESI-MS: 427.1 [M+H]+

¹H-NMR (DMSO-d₆, 400 Hz): δ [ppm] 11.3 (broad, 1H), 9.7 (s broad, 1H), 7.4 (s, 1H), 7.25-7.35 (m, 2H), 7.1 (d, 1H), 6.97 (d, 1H), 6.95 (s, 1H), 6.9 (t, 1H), 3.0-3.5 (broad, 8H), 2.8 (s, 3H), 2.3 (s, 3H), 2.25 (s, 3H).

EXAMPLE 92

N-(2-Difluoromethoxy-5-methyl-phenyl)-4-methyl-3-(4-methyl-piperazin-1-yl)-benzenesulfonamide hydrochloride

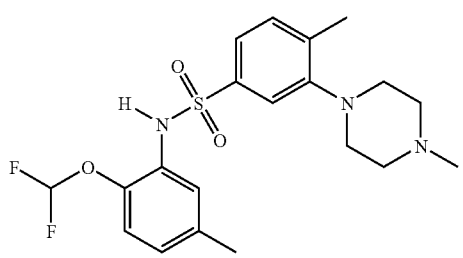

ESI-MS: 427.5 [M+H]+

¹H-NMR (DMSO-d₆, 400 Hz): δ [ppm] 11.3 (broad, 1H), 9.8 (s broad, 1H), 7.4 (s, 1H), 7.32 (s, 2H), 7.1 (s, 1H), 7.0 (m, 2H), 6.85 (t, 1H), 6.9 (t, 1H), 3.0-3.5 (broad, 8H), 2.8 (s, 3H), 2.3 (s, 3H), 2.2 (s, 3H).

EXAMPLE 93

N-(4-Difluoromethoxy-3-methoxy-phenyl)-4-methoxy-3-piperazin-1-yl-benzenesulfonamide hydrochloride

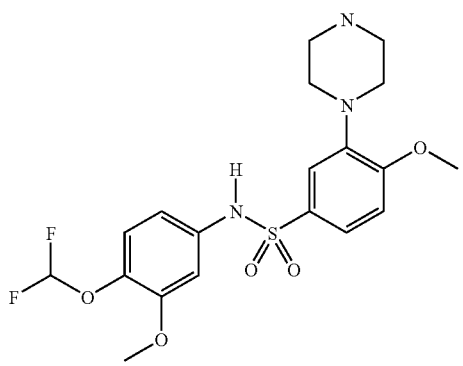

ESI-MS: 444.1 [M+H]+

¹H-NMR (DMSO-d₆, 400 Hz): δ [ppm] 8.4 (broad, 1H), 7.42 (m, 1H), 7.24 (s, 1H), 7.0-7.15 (m, 2H), 6.85-7.0 (m, 2H), 6.7 (m, 1H), 3.8 (s, 3H), 3.7 (s, 3H), 3.0 (broad, 8H).

EXAMPLE 94

N-(3-Difluoromethoxy-phenyl)-4-methyl-3-(4-methyl-piperazin-1-yl)-benzenesulfonamide hydrochloride

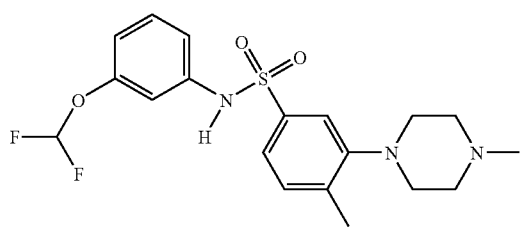

ESI-MS: 412.1 [M+H]+

¹H-NMR (DMSO-d₆, 400 Hz): δ [ppm] 10.5 (s broad, 1H), 7.2-7.4 (several m, 3H), 7.15 (t, 1H), 7.0 (d, 1H), 6.92 (s, 1H), 6.82 (d, 1H), 3.0-3.5 (broad, 8H), 2.8 (s, 3H), 2.25 (s, 3H).

EXAMPLE 95

N-(4-Difluoromethoxy-phenyl)-4-methoxy-3-(4-methyl-piperazin-1-yl)-benzenesulfonamide hydrochloride

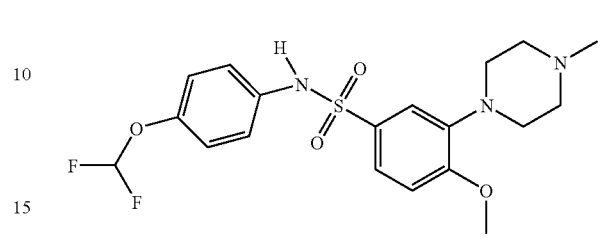

ESI-MS: 428.1 [M+H]+

¹H-NMR (DMSO-d₆, 400 Hz): δ [ppm] 11.3 (broad, 1H), 10.2 (s, 1H), 7.38 (d, 1H), 7.3 (s, 1H), 7.15 (dd, 2H), 7.07 (m, 3H), 7.1 (t, 1H), 3.8 (s, 3H), 3.4 (broad, 4H), 3.1 (broad, 4H), 2.8 (s, 3H).

EXAMPLE 96

3-[1,4]Diazepan-1-yl-N-(3-difluoromethoxy-phenyl)-4-methyl-benzenesulfonamide hydrochloride

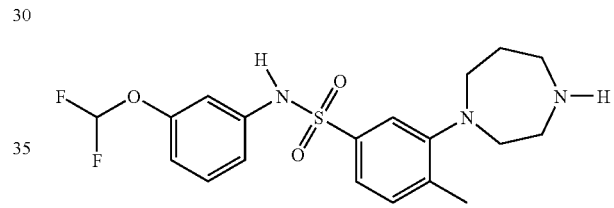

ESI-MS: 412.1 [M+H]+

¹H-NMR (DMSO-d₆, 400 Hz): δ [ppm] 10.53 (s, 1H), 9.55 (s, 2H), 7.45 (s, 1H), 7.2-7.4 (m, 3H), 7.15 (t, 1H), 7.0 (d, 1H), 6.95 (s, 1H), 6.8 (d, 1H), 3.25 (broad, 6H), 3.05 (m, 2H), 2.25 (s, 3H), 2.05 (broad, 2H).

EXAMPLE 97

3-[1,4]Diazepan-1-yl-N-(2-difluoromethoxy-phenyl)-4-methyl-benzenesulfonamide hydrochloride

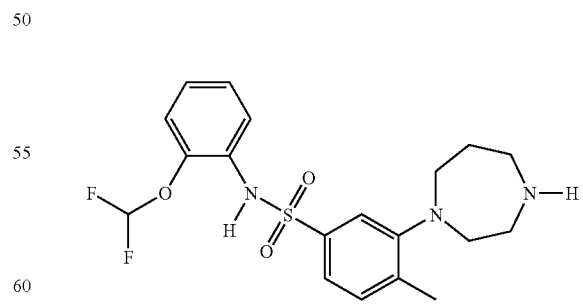

ESI-MS: 412.1 [M+H]+

¹H-NMR (DMSO-d₆, 400 Hz): δ [ppm] 9.8 (s, 1H), 9.4 (s, 2H), 7.4 (s, 1H), 7.2-7.35 (m, 3H), 7.1-7.2 (m, 3H), 6.9 (t, 1H), 3.25 (broad, 6H), 3.05 (m, 2H), 2.3 (s, 3H), 2.05 (broad, 2H).

EXAMPLE 98

3-[1,4]Diazepan-1-yl-N-(3-difluoromethoxy-4-methyl-phenyl)-4-methyl-benzenesulfonamide hydrochloride

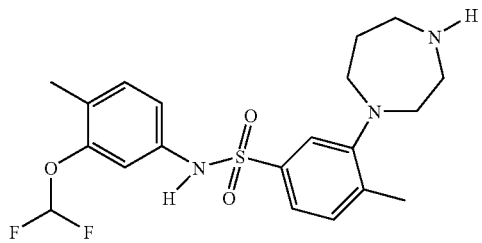

ESI-MS: 426.1 [M+H]+
1H-NMR (DMSO-d6, 400 Hz): δ [ppm] 10.3 (s, 1H), 9.45 (s, 2H), 7.4 (s, 1H), 7.3 (s, 2H), 7.15 (d, 1H), 7.05 (t, 1H), 6.95 (s, 1H), 6.87 (d, 1H), 3.25 (broad, 6H), 3.05 (m, 2H), 2.3 (s, 3H), 2.1 (s, 3H), 2.05 (broad, 2H).

EXAMPLE 99

N-(3-Difluoromethoxy-4-methyl-phenyl)-4-methyl-3-(4-methyl-[1,4]diazepan-1-yl)-benzenesulfonamide hydrochloride

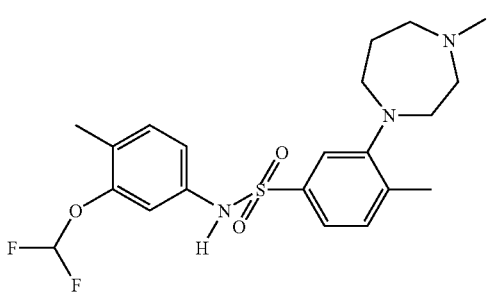

ESI-MS: 440.2 [M+H]+

EXAMPLE 100

N-(2-Difluoromethoxy-phenyl)-4-methyl-3-(4-methyl-[1,4]diazepan-1-yl)-benzenesulfonamide hydrochloride

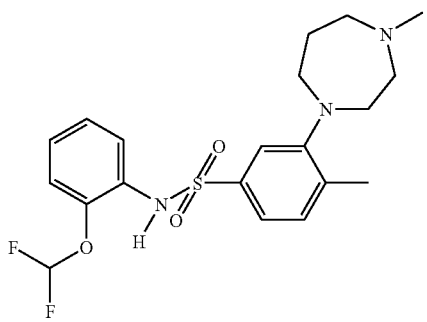

ESI-MS: 426.1 [M+H]+
1H-NMR (DMSO-d6, 400 Hz): δ [ppm] 9.5-11.0 (very broad, 2H), 7.4 (s, 1H), 7.2-7.35 (m, 3H), 7.1-7.2 (m, 3H), 6.93 (t, 1H), 3.4 (broad, 6H), 3.05 (m, 2H), 2.8 (s, 3H), 2.3 (s, 3H), 2.15 (broad, 2H).

EXAMPLE 101

N-(3-Difluoromethoxy-phenyl)-4-methyl-3-(4-methyl-[1,4]diazepan-1-yl)-benzenesulfonamide hydrochloride

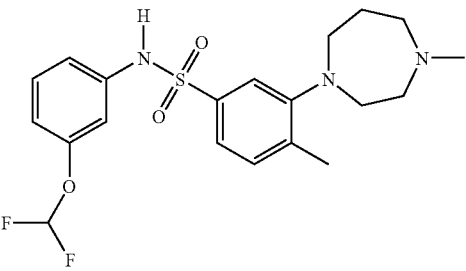

ESI-MS: 426.2 [M+H]+

EXAMPLE 102

N-(5-Difluoromethoxy-2-methylphenyl)-4-difluoromethoxy-3-piperazin-1-yl benzenesulfonamide

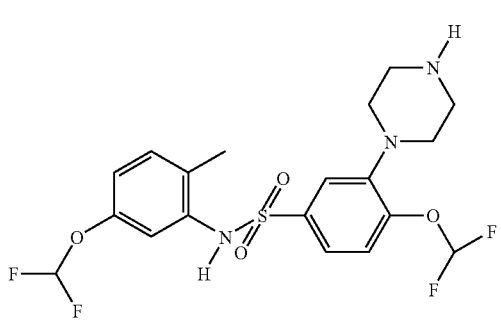

EXAMPLE 103

N-(5-Difluoromethoxy-2-methylphenyl)-4-difluoromethoxy-N-methyl-3-piperazin-1-yl benzenesulfonamide

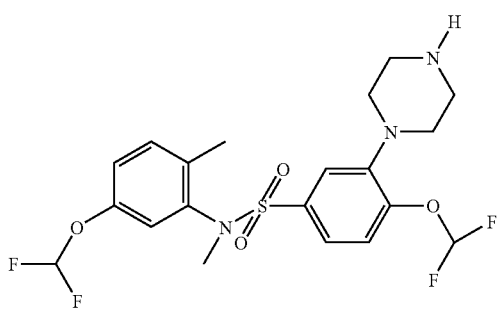

EXAMPLE 104

N-(5-Difluoromethoxy-2-methylphenyl)-4-fluoro-3-piperazin-1-yl benzenesulfonamide

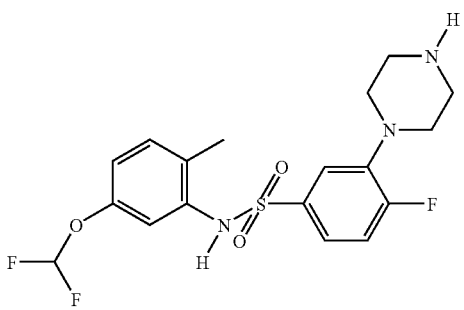

EXAMPLE 105

N-(5-Difluoromethoxy-2-methylphenyl)-4-fluoro-N-methyl-3-piperazin-1-yl benzenesulfonamide

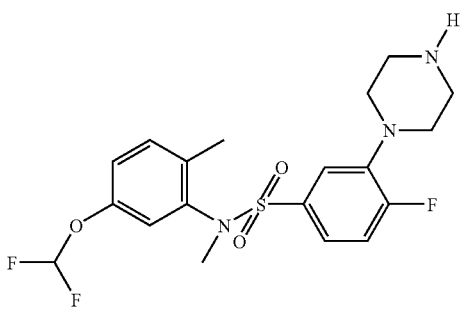

III. Biological Investigations

Displacement of Radioligands Binding to the Following Cloned Human Receptors

1. Preparation of Membranes by Ultrasonic Treatment and Differential Centrifugation Cells from stable clonal cell lines expressing the corresponding receptor (5-$HT_6$, $\alpha_1$-adrenergic, dopamine $D_2$ or histamine $H_1$ receptors) were washed with PBS (w/o $Ca^{++}$, $Mg^{++}$) and harvested in PBS with 0.02% EDTA. The cells were collected by centrifugation at 500 g for 10 min. at 4° C., washed with PBS and centrifuged (500 g, 10 min. 4° C.). The pellets were stored at −80° C. until use. For membrane preparation, the thawed cell pellet was resuspended in ice-cold sucrose buffer (0.25 M sucrose, 10 mM Hepes (pH 7.4), 1 mM Phenylmethylsulfonyl fluoride (PMSF) in DMSO, 5 µg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1.000 g for 10 min. at 4° C. The sucrose buffer supernatant was then centrifuged at 60.000 g for 1 h at 4° C. (Beckman Ultrazentrifuge XL 80). The pellet was resuspended in 30 ml ice-cold Tris buffer (20 mM TRIS (pH 7.4), 5 µg/ml Pepstatin A, 0.1 mM PMSF, 3 mM EDTA) by pipetting through a 10 ml serological pipet and centrifuged for 1 h at 4° C. at 60.000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

2. Receptor Binding Experiments

All receptor binding experiments were carried out in the corresponding assay buffer in a total volume of 200 µl in the presence of various concentrations of test compound ($10^{-5}$ M to $10^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96well-plate harvester. After the plates had been dried for 2 h at 55° C. in a drying chamber scintillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980).

a) 5-$HT_6$ Receptor Binding Assay

HEK293 cells stably expressing the h-5-$HT_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a $K_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM $CaCl_2$, 0.1% ascorbic acid, 10 µM pargyline, pH 7.4) to a concentration of 8 µg protein/assay and homogenized by gentle vortexing For inhibition studies, 1 nM [$^3$H]-Lysergic Acid Diethylamide was incubated in the presence of various concentrations of test compound in assay buffer. Non-specific binding was defined with 1 µM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM $CaCl_2$.

a) Dopamine $D_2$ Receptor Binding Assay

HEK293 cells stably expressing the dopamine $D_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a $K_D$ of 0.22 nM for [$^{125}$I]-iodospiperone (PerkinElmer Life Sciences, NEX284) was determined by means of saturation binding experiments. On the day of the assay, the membranes were thawed, diluted in assay buffer (50 mM Tris-HCl, 120 mM NaCl, 5 mM $MgCl_2$, 5 mM KCl, 1.5 mM $CaCl_2$, pH 7.4) to a concentration of 15 µg protein/assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 µM haloperidol. The binding reaction was carried out for 1 h at room temperature and terminated by filtration on Packard Unifilter GF/B (0.1% PEI) plates, followed by 6 wash cycles with an ice-cold 7% polyethylenglycol solution.

b) α₁-Adrenergic Receptor Binding Assay

CHO—K₁ cells stably expressing the $\alpha_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a $K_D$ of 0.12 nM for [³H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 μg protein/assay and homogenized by gentle vortexing. For inhibition studies, 0.1 nM [³H]-prazosine (PerkinElmer Life Sciences, NET823) was incubated in the presence of various concentrations of test compound in assay buffer. Non-specific binding was defined with 1 μM phentolamine. The binding reaction was carried out for 1 h at room temperature and terminated by filtration on Packard Unifilter GF/C (0.1% PEI) plates, followed by 3 wash cycles with ice-cold assay buffer.

c) H₁ Receptor Binding Assay

CHO—K₁ cells stably expressing the histamine H₁ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a $K_D$ of 0.83 nM for [³H]-pyrilamine (PerkinElmer Life Sciences, NET594) was determined by means of saturation binding experiments. On the day of the assay, the membranes were thawed, diluted in assay buffer (50 mM $Na_2HPO_4$, 50 mM $KH_2PO_4$, pH 7.4) to a concentration of 6 μg protein/assay and homogenized by gentle vortexing. For inhibition studies, 1 nM [³H]-pyrilamine (PerkinElmer Life Sciences, NET594) was incubated in the presence of various concentrations of test compound in assay buffer. Non-specific binding was defined with 1 μM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). $IC_{50}$, nH and $K_i$ values were expressed as geometrical mean. For receptors with a low affinity for the test compound, where the highest tested compound concentration inhibited less than 30% of specific radioligand binding, $K_i$-values were determined according to the equation of Cheng and Prusoff (Biochem. Pharmacol. 1973, 22, 2099-2108) and expressed as greater than (>).

The results of the receptor binding studies are expressed as receptor binding constants $K_i$(5-$HT_6$), $K_i$($D_2$), $K_i$($\alpha_1$-adrenergic) and $K_i$($H_1$), respectively, as described herein before, and given in table I.

In these tests, the compounds according to the invention exhibit very good affinities for the 5-$HT_6$ receptor ($K_i$<500 nM or <100 nM or <50 nM or <20 nM and frequently <10 nM). Furthermore those compounds bind selectively to the 5-$HT_6$ receptor, as compared to the affinity for the $D_2$, the $\alpha_1$-adrenergic or the $H_1$ receptors. These compounds exhibit little affinities for the $D_2$, $\alpha_1$-adrenergic or $H_1$ receptors ($K_i$>500 nM or >1000 nM and frequently >10000 nM).

Example 1: Ki (5HT₆) <10 nM
Example 5: Ki (5HT₆) <50 nM
Example 6: Ki (5HT₆) <50 nM
Example 7: Ki (5HT₆) <50 nM
Example 8: Ki (5HT₆) <500 nM
Example 9: Ki (5HT₆) <500 nM
Example 10: Ki (5HT₆) <50 nM
Example 11: Ki (5HT₆) <500 nM
Example 12: Ki (5HT₆) <50 nM
Example 13: Ki (5HT₆) <50 nM
Example 14: Ki (5HT₆) <100 nM
Example 15: Ki (5HT₆) <500 nM
Example 16: Ki (5HT₆) <500 nM
Example 17: Ki (5HT₆) <10 nM
Example 18: Ki (5HT₆) <10 nM
Example 24: Ki (5HT₆) <10 nM
Example 25: Ki (5HT₆) <10 nM
Example 26: Ki (5HT₆) <10 nM
Example 27: Ki (5HT₆) <50 nM
Example 28: Ki (5HT₆) <50 nM
Example 29: Ki (5HT₆) <10 nM
Example 30: Ki (5HT₆) <10 nM
Example 31: Ki (5HT₆) <50 nM
Example 32: Ki (5HT₆) <10 nM
Example 33: Ki (5HT₆) <10 nM
Example 34: Ki (5HT₆) <10 nM
Example 35: Ki (5HT₆) <10 nM
Example 36: Ki (5HT₆) <10 nM
Example 37: Ki (5HT₆) <10 nM
Example 38: Ki (5HT₆) <10 nM
Example 39: Ki (5HT₆) <500 nM
Example 40: Ki (5HT₆) <50 nM
Example 41: Ki (5HT₆) <10 nM
Example 42: Ki (5HT₆) <10 nM
Example 43: Ki (5HT₆) <500 nM
Example 45: Ki (5HT₆) <10 nM
Example 46: Ki (5HT₆) <10 nM
Example 47: Ki (5HT₆) <10 nM
Example 48: Ki (5HT₆) <10 nM
Example 49: Ki (5HT₆) <10 nM
Example 51: Ki (5HT₆) <10 nM
Example 52: Ki (5HT₆) <50 nM
Example 53: Ki (5HT₆) <10 nM
Example 54: Ki (5HT₆) <10 nM
Example 55: Ki (5HT₆) <10 nM
Example 56: Ki (5HT₆) <50 nM
Example 57: Ki (5HT₆) <10 nM
Example 58: Ki (5HT₆) <10 nM
Example 59: Ki (5HT₆) <10 nM
Example 60: Ki (5HT₆) <10 nM
Example 61: Ki (5HT₆) <10 nM
Example 62: Ki (5HT₆) <10 nM
Example 63: Ki (5HT₆) <10 nM
Example 64: Ki (5HT₆) <10 nM
Example 65: Ki (5HT₆) <10 nM
Example 66: Ki (5HT₆) <10 nM
Example 67: Ki (5HT₆) <10 nM
Example 68: Ki (5HT₆) <10 nM
Example 69: Ki (5HT₆) <10 nM
Example 70: Ki (5HT₆) <10 nM
Example 71: Ki (5HT₆) <10 nM
Example 72: Ki (5HT₆) <10 nM
Example 73: Ki (5HT₆) <10 nM
Example 74: Ki (5HT₆) <50 nM
Example 75: Ki (5HT₆) <50 nM
Example 76: Ki (5HT₆) <50 nM
Example 77: Ki (5HT₆) <50 nM
Example 78: Ki (5HT₆) <50 nM
Example 79: Ki (5HT₆) <50 nM Example 80: Ki (5HT$_6$) <50 nM
Example 81: Ki (5HT$_6$) <50 nM
Example 82: Ki (5HT$_6$) <10 nM
Example 83: Ki (5HT$_6$) <10 nM
Example 84: Ki (5HT$_6$) <50 nM
Example 85: Ki (5HT$_6$) <500 nM
Example 86: Ki (5HT$_6$) <500 nM
Example 87: Ki (5HT$_6$) <50 nM
Example 88: Ki (5HT$_6$) <500 nM
Example 89: Ki (5HT$_6$) <10 nM
Example 90: Ki (5HT$_6$) <50 nM
Example 91: Ki (5HT$_6$) <50 nM
Example 92: Ki (5HT$_6$) <10 nM
Example 93: Ki (5HT$_6$) <10 nM
Example 94: Ki (5HT$_6$) <10 nM
Example 95: Ki (5HT$_6$) <10 nM
Example 96: Ki (5HT$_6$) <50 nM
Example 97: Ki (5HT$_6$) <10 nM
Example 98: Ki (5HT$_6$) <50 nM
Example 99: Ki (5HT$_6$) <500 nM
Example 100: Ki (5HT$_6$) <10 nM
Example 101: Ki (5HT$_6$) <10 nM 3. Determination of the Metabolic Stability The metabolic stability of the compounds of the invention was determined in the following assay by analyzing the microsomal half-life. The test substances are incubated in a concentration of 0.5 μM as follows:

0.5 μM test substance is preincubated together with liver microsomes of various species (0.25 mg of protein/ml) in 0.05M potassium phosphate buffer pH 7.4 in microtiter plates at 37° C. for 5 min. The reaction is started by adding NADPH (1 mg/mL). Aliquots are taken after 0, 5, 10, 15, 20 and 30 min, and the reaction is stopped with the same volume of acetonitrile and cooled down. The remaining test compound concentrations are being determined by liquid chromatography—mass spectrometry analysis. Intrinsic clearance values are calculated using the elimination rate constant of test compound depletion.

We claim:

1. N-Phenyl-(piperazinyl or homopiperazinyl)-benzenesulfonamide or benzenesulfonyl-phenyl-(piperazine or homopiperazine) of formula (I) or (I')

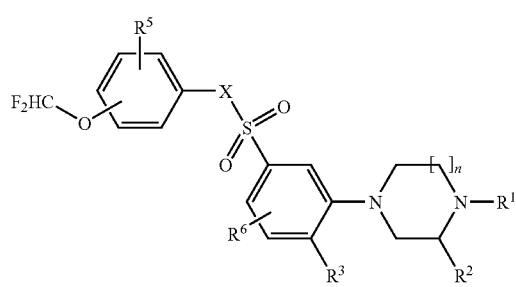

(I)

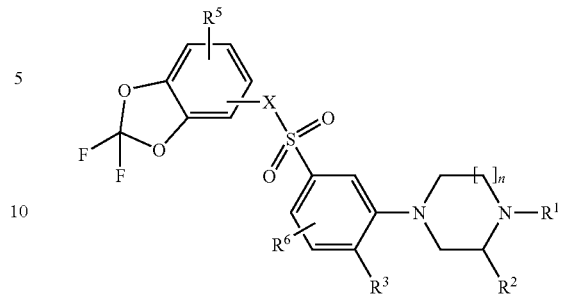

(I')

wherein
X is a bond or a group N-R$^4$;
R$^1$ is hydrogen or methyl;
R$^2$ is hydrogen or methyl;
R$^3$ is hydrogen, C$_1$-C$_3$ alkyl, fluorine, C$_1$-C$_2$ alkoxy or fluorinated C$_1$-C$_2$ alkoxy;
R$^4$ is hydrogen, C$_1$-C$_4$ alkyl, C$_3$-C$_4$ cycloalkyl, or C$_3$-C$_4$ cycloalkyl-CH$_2$-;
R$^5$ is hydrogen, fluorine, chlorine, C$_1$-C$_2$ alkyl, fluorinated C$_1$-C$_2$ alkyl, C$_1$-C$_2$ alkoxy or fluorinated C$_1$-C$_2$ alkoxy;
R$^6$ is hydrogen, fluorine or chlorine; and
n is 1 or 2,
or a physiologically tolerated acid addition salt or an N-oxide thereof.

2. The compound as claimed in claim 1, wherein R$^5$ is hydrogen, fluorine, C$_1$-C$_2$ alkyl, fluorinated C$_1$-C$_2$ alkyl, C$_1$-C$_2$ alkoxy or fluorinated C$_1$-C$_2$ alkoxy.

3. The compound of claim 1, where R$^1$ is hydrogen.

4. The compound of claim 1, wherein R$^2$ is hydrogen.

5. The compound of claim 1, wherein R$^2$ is methyl.

6. The compound of claim 1, wherein X is a group N—R$^4$.

7. The compound of claim 1, wherein n is 1.

8. The compound of claim 1, wherein R$^3$ is methyl or methoxy.

9. The compound of claim 1, wherein R$^3$ is hydrogen or fluorine.

10. The compound of claim 1, wherein R$^4$ is hydrogen, C$_1$-C$_4$ alkyl or cyclopropylmethyl.

11. The compound of claim 1, wherein R$^4$ is hydrogen.

12. The compound of claim 1, wherein R$^5$ is hydrogen.

13. The compound of claim 1, wherein R$^5$ is methyl, methoxy or difluoromethoxy.

14. The compound of claim 1, wherein R$^5$ is chlorine or fluorine.

15. The compound of claim 1, wherein R$^6$ is hydrogen.

16. The compound of claim 1, wherein R$^5$ and R$^6$ are hydrogen, R$^3$ is selected from the group consisting of C$_1$-C$_2$ alkyl and C$_1$-C$_2$ alkoxy, and R$^4$ is selected from the group consisting of hydrogen, C$_1$-C$_4$ alkyl, or cyclopropylmethyl.

17. The compound of claim 1, wherein
X is a bond or a group N—R$^4$;
R$^1$ is hydrogen or methyl;
R$^2$ is hydrogen;
R$^3$ is hydrogen, C$_1$-C$_2$ alkyl, C$_1$-C$_2$ alkoxy ;
R$^4$ is hydrogen, methyl, ethyl, n-propyl, isopropyl or cyclopropylmethyl;
R$^5$ is hydrogen, methyl or methoxy;
R$^6$ is hydrogen; and
n is 1 or 2.

18. The compound of claim 17, wherein R$^3$ is methyl.

19. The compound of claim 18, wherein R$^5$ is hydrogen.

20. The compound of claim 19, wherein R$^4$ is hydrogen.

21. The compound of claim 20, wherein $R^1$ is hydrogen.

22. The compound of claim 21, wherein X is a group N—$R^4$.

23. The compound of claim 22, wherein n is 1.

24. The compound of claim 23, wherein the $OCHF_2$-radical in formula I is located on the benzene ring in the ortho-position with respect to X.

25. The compound of claim 23, wherein the $OCHF_2$-radical in formula I is located on the benzene ring in the meta-position with respect to X.

26. The compound of claim 23, wherein the $OCHF_2$-radical in formula I is located on the benzene ring in the para-position with respect to X.

27. A pharmaceutical composition comprising at least one compound of claim 1, optionally together with at least one physiologically acceptable carrier or auxiliary substance.

28. A non-prophylactic method for treating acute or chronic signs, symptoms and/or malfunctions of a disorder selected from diseases of the central nervous system or obesity, said method comprising administering an effective amount of at least one compound of claim 1 to a subject in need thereof, wherein said disease of the central nervous system is a cognitive dysfunction associated with Alzheimer's Disease or schizophrenia.

* * * * *

UNITED STATES PATENT AND TRADEMARK OFFICE
CERTIFICATE OF CORRECTION

PATENT NO.        : 8,076,326 B2
APPLICATION NO.   : 12/770837
DATED             : December 13, 2011
INVENTOR(S)       : Andreas Haupt et al.

It is certified that error appears in the above-identified patent and that said Letters Patent is hereby corrected as shown below:

Title page, item [54] the title should read as follows:

-- N-PHENYL- (PIPERAZINYL OR HOMOPIPERAZINYL)-BENZENESULFONAMIDE OR BENZENESULFONYL-PHENYL-(PIPERAZINE OR HOMOPIPERAZINE) COMPOUNDS SUITABLE FOR TREATING DISORDERS THAT RESPOND TO MODULATION OF THE SEROTONIN 5-HT6 RECEPTOR --

Signed and Sealed this
Twenty-fourth Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,076,326 B2 | Page 1 of 1 |
| APPLICATION NO. | : 12/770837 | |
| DATED | : December 13, 2011 | |
| INVENTOR(S) | : Andreas Haupt et al. | |

It is certified that error appears in the above-identified patent and that said Letters Patent is hereby corrected as shown below:

Title page, item [54] and at Column 1, lines 1 and 2, the title should read as follows:

-- N-PHENYL-(PIPERAZINYL OR HOMOPIPERAZINYL)-BENZENESULFONAMIDE OR BENZENESULFONYL-PHENYL-(PIPERAZINE OR HOMOPIPERAZINE) COMPOUNDS SUITABLE FOR TREATING DISORDERS THAT RESPOND TO MODULATION OF THE SEROTONIN 5-HT6 RECEPTOR --

This certificate supersedes the Certificate of Correction issued January 24, 2012.

Signed and Sealed this
Fourteenth Day of February, 2012

David J. Kappos
*Director of the United States Patent and Trademark Office*